(12) United States Patent
Jansen et al.

(10) Patent No.: US 9,624,514 B2
(45) Date of Patent: Apr. 18, 2017

(54) PROCESS FOR PREPARING DICARBOXYLIC ACIDS EMPLOYING FUNGAL CELLS

(75) Inventors: Mickel Leonardus August Jansen, Echt (NL); Joseph Johannes Heijen, Echt (NL); René Verwaal, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 156 days.

(21) Appl. No.: 14/130,347

(22) PCT Filed: Jul. 2, 2012

(86) PCT No.: PCT/EP2012/062860
§ 371 (c)(1),
(2), (4) Date: Mar. 20, 2014

(87) PCT Pub. No.: WO2013/004670
PCT Pub. Date: Jan. 10, 2013

(65) Prior Publication Data
US 2014/0342416 A1   Nov. 20, 2014

(30) Foreign Application Priority Data

Jul. 1, 2011 (EP) .................................... 11172444

(51) Int. Cl.
| | | |
|---|---|---|
| *C12P 7/46* | (2006.01) | |
| *C12P 7/40* | (2006.01) | |
| *C07C 55/10* | (2006.01) | |
| *C08G 63/16* | (2006.01) | |
| *C12P 7/44* | (2006.01) | |
| *C12N 1/18* | (2006.01) | |

(52) U.S. Cl.
CPC .................. *C12P 7/44* (2013.01); *C12N 1/18* (2013.01); *C12P 7/46* (2013.01)

(58) Field of Classification Search
CPC ... C12P 7/46; C12P 7/40; C07C 55/10; C08G 63/16; Y02E 50/343; C12R 1/645
See application file for complete search history.

(56) References Cited

U.S. PATENT DOCUMENTS

| | | |
|---|---|---|
| 2,327,191 A | 8/1943 | Kane et al. |
| 2011/0081694 A1 | 4/2011 | Verwaal et al. |
| 2012/0040422 A1 | 2/2012 | Jansen et al. |
| 2012/0135482 A1 | 5/2012 | Jansen et al. |
| 2012/0165569 A1 | 6/2012 | Verwaal et al. |
| 2013/0171704 A1 | 7/2013 | Jansen et al. |

FOREIGN PATENT DOCUMENTS

| | | |
|---|---|---|
| WO | 2007/061590 | 5/2007 |
| WO | 2008/014462 | 1/2008 |
| WO | 2009/065778 | 5/2009 |
| WO | 2010/118932 | 10/2010 |
| WO | 2011/023700 | 3/2011 |
| WO | 2012/038390 | 3/2012 |

OTHER PUBLICATIONS

International Search Report for PCT/EP2012/062860 Mailed Oct. 1, 2012.

*Primary Examiner* — Kagnew H Gebreyesus
(74) *Attorney, Agent, or Firm* — McBee Moore Woodward & Vanik IP, LLC

(57) ABSTRACT

The present invention relates to a process for producing a dicarboxylic acid comprising fermenting a fungal cell in a vessel comprising a suitable fermentation medium, comprising adding a gas flow which comprises 20 to 35 v/v % of oxygen and less than 0.1 v/v % of carbon dioxide to the fermentation medium, and maintaining an average partial carbon dioxide pressure of at least about 0.35 bar in the fermentation medium, and producing the dicarboxylic acid.

19 Claims, 13 Drawing Sheets

SEQUENCE LISTING

<160> NUMBER OF SEQ ID NOS: 8

<210> SEQ ID NO 1
<211> LENGTH: 18320
<212> TYPE: DNA
<213> ORGANISM: Artificial Sequence
<220> FEATURE:
<223> OTHER INFORMATION: Plasmid pSUC044

<400> SEQUENCE: 1

```
atttcgcgca agctaattcc ctattgtgag tcgtattaaa ttcgtaatca tgtcatagct      60
gtttcctgtg tgaaattgtt atccgctcac aattccacac aacatacgag ccggaagcat     120
aaagtgtaaa gcctggggtg cctaatgagt gagctaactc acattaattg cgttgcgctc     180
actgcccgct ttccagtcgg gaaacctgtc gtgccagctg cattaatgaa tcggccaacg     240
cgcggggaga ggcggtttgc gtattgggcg ctcttccgct tcctcgctca ctgactcgct     300
gcgctcggtc gttcggctgc ggcgagcggt atcagctcac tcaaaggcgg taatacggtt     360
atccacagaa tcaggggata acgcaggaaa gaacatgtga gcaaaaggcc agcaaaaggc     420
caggaaccgt aaaaaggccg cgttgctggc gtttttccat aggctccgcc cccctgacga     480
gcatcacaaa aatcgacgct caagtcagag gtggcgaaac ccgacaggac tataaagata     540
ccaggcgttt ccccctggaa gctccctcgt gcgctctcct gttccgaccc tgccgcttac     600
cggatacctg tccgcctttc tcccttcggg aagcgtggcg ctttctcaat gctcacgctg     660
taggtatctc agttcggtgt aggtcgttcg ctccaagctg ggctgtgtgc acgaaccccc     720
cgttcagccc gaccgctgcg ccttatccgg taactatcgt cttgagtcca acccggtaag     780
acacgactta tcgccactgg cagcagccac tggtaacagg attagcagag cgaggtatgt     840
aggcggtgct acagagttct tgaagtggtg gcctaactac ggctacacta gaaggacagt     900
atttggtatc tgcgctctgc tgaagccagt taccttcgga aaagaggtg gtagctcttg      960 atccggcaaa caaaccaccg ctggtagcgg tggttttttt gtttgcaagc agcagattac    1020
gcgcagaaaa aaaggatctc aagaagatcc tttgatcttt tctacggggt ctgacgctca    1080
gtggaacgaa aactcacgtt aagggatttt ggtcatgaga ttatcaaaaa ggatcttcac    1140
ctagatcctt ttaaattaaa aatgaagttt taaatcaatc taaagtatat atgagtaaac    1200
ttggtctgac agttaccaat gcttaatcag tgaggcacct atctcagcga tctgtctatt    1260
```

```
tcgttcatcc atagttgcct gactcccgt  cgtgtagata actacgatac gggagggctt    1320
accatctggc cccagtgctg caatgatacc gcgagaccca cgctcaccgg ctccagattt    1380
atcagcaata aaccagccag ccggaagggc cgagcgcaga agtggtcctg caactttatc    1440
cgcctccatc cagtctatta attgttgccg ggaagctaga ctaagtagtt cgccagttaa    1500
tagtttgcgc aacgttgttg ccattgctac aggcatcgtg gtgtcacgct cgtcgtttgg    1560
tatggcttca ttcagctccg gttcccaacg atcaaggcga gttacatgat cccccatgtt    1620
gtgcaaaaaa gcggttagct ccttcggtcc tccgatcgtt gtcagaagta agttggccgc    1680
agtgttatca ctcatggtta tggcagcact gcataattct cttactgtca tgccatccgt    1740
aagatgcttt tctgtgactg gtgagtactc aaccaagtca ttctgagaat agtgtatgcg    1800
gcgaccgagt tggtcttgcc cggcgtcaat acgggataat accgcgccac atagcagaac    1860
tttaaaagtg ctcatcattg gaaaacgttc ttcggggcga aaactctcaa ggatcttacc    1920
gctgttgaga tccagttcga tgtaacccac tcgtgcaccc aactgatctt cagcatcttt    1980
tactttcacc agcgtttctg ggtgagcaaa acaggaagg  caaaatgccg caaaaaaggg    2040
aataagggcg acacggaaat gttgaatact catactcttc cttttcaat  attattgaag    2100
catttatcag ggttattgtc tcatgagcgg atacatattt gaatgtattt agaaaaataa    2160
acaaataggg gttccgcgca catttccccg aaaagtgcca cctgacgcgc cctgtagcgg    2220
cgcattaagc gcggcgggtg tggtggttac gcgcagcgtg accgctacac ttgccagcgc    2280
cctagcgccc gctcctttcg ctttcttccc ttcctttctc gccacgttcg ccggctttcc    2340
ccgtcaagct ctaaatcggg ggctcccttt agggttccga tttagtgctt tacggcacct    2400
cgacccaaa  aaacttgatt agggtgatgg ttcacgtagt gggccatcgc cctgatagac    2460
ggtttttcgc cctttgacgt tggagtccac gttctttaat agtggactct tgttccaaac    2520
tggaacaaca ctcaacccta tctcggtcta ttcttttgat ttataaggga ttttgccgat    2580
ttcggcctat tggttaaaaa atgagctgat ttaacaaaaa tttaacgcga attttaacaa    2640
aatattaacg tttacaattt cccattcgcc attcaggctg cgcaactgtt gggaagggcg    2700
atcggtgcgg gcctcttcgc tattacgcca gctggcgaaa gggggatgtg ctgcaaggcg    2760
attaagttgg gtaaggccag ggttttccca gtcacgacgt tgtaaaacga cggccagtgc    2820
caagctagct ttgcagtgcg aatggggag  gagagtagat tctttcttca agaaagcaaa    2880
atattgaaat cttaagagaa ctagatgaaa gatttgattt attaacgaac cggaaggtta    2940
tatactattc ccatttttg  aaggtatatg ctaatatgtt tgagcgtttg ttatttcccc    3000
actcgtcttt ttgcctaaat agtgcctcga acctaaagt  ggatttgtca ttagctgtga    3060
cttacatttc cgaacttatc cgctcaacta gaagtcaatg gagaagcaat gcattaaatt    3120
gcctttcgcc ctctctctcg agttcctttg gatcaccctg atgcacgcct tgcatatcga    3180
gaaatctctt cgaaggcatc ttacagaatt tcgtttcct  tttctctatt tttcattctg    3240
agaaatattt gcctgcatac attgtaatgg cgatctggtg atccgcaatt ctagaacaca    3300
caatatgcat gtaatcgctg attttttttg tttttagaagc tctatcttca ggtaaaaatg    3360
agtagagaaa aaaaaacata ctggatcgat gcagaattag ggggttatta tcctgcaggt    3420
acatgatttt cagtgggaac attgcttttt agtagtccgg ttctcaacaa cttgtctaag    3480
tgttgaaaac aaaagaaatg gcgtagaaac aaagtagtgt aagtaaatct gccaatgttc    3540
tatgtataaa aagtaaaggc aagaagaggt tctatgcata tttctgaaaa tatctaatac    3600
```

```
actattataa tgcatcaaga aactgtcgta tgatgaagtg cctatgagtt tttgtgtacg    3660
tgcttctcta gtatgtagcc ggttttctct ttttacctct ttttactact tatactacta    3720
cttttactac ctttcttcca cgtaatctag atctcaagcc acaattcttg ccctatgctc    3780
caacgtatac aacatcgaag aagagtctttt ctttagggag tcattggaaa agatagtatg    3840
atggtattcg atttacctat gtcgcaaaag aaagtccggg gcaacaccac agaatgcttt    3900
ctctgtacta ataacctgtt gtgcgcttaa cggtctaatc gttaatcagc ggtggttaaa    3960
tttttgtaaa tctaatgttc catgattttc tttcttcaaa aggaacatgt agcgaaaatc    4020 tttttttttac tttgatacac tgcaattgtt tctgagcatg ctgaaatttt ctcgatgttt    4080
ttttttttta ttggcatcca agtaattaat ccttatgcta cgaaaaagtt gtaggaatga    4140
atcatgcata atctaacgga tatcatcata tactctgtgc taatattcta acaagttcg    4200 aaaatatttt cttggcccat gtaataggtg gtaagtgtat tgcttttgata ggaacgtcat    4260 tatcgcacaa gacaatcggc actaataacc gtttaaatat tatcatgcat gtatacatca    4320
gtatctcata gaaatatacc tgtaagtaca tacttatcta agtataaatt ctcgacctat    4380
ggagtcacca catttcccag caacttcccc acttcctctg caatcgccaa cgtcctctct    4440
tcactgagtc tccgtccgat aacctgcact gcaaccggtg ccccatggta cgcctccgga    4500
tcatactctt cctgcacgag ggcatcaagc tcactaaccg ccttgaaact ctcattcttc    4560
ttatcgatgt tcttatccgc aaaggtaacc ggaacaacca cgctcgtgaa atccagcagg    4620
ttgatcacag aggcataccc atagtaccgg aactggtcat gccgtaccgc agcggtaggc    4680
gtaatcggcg cgatgatggc gtccagttcc ttcccggcct tttcttcagc ctcccgccat    4740
ttctcaaggt actccatctg gtaattccac ttctggagat gcgtgtccca gagctcgttc    4800
atgttaacag ctttgatgtt cgggttcagt aggtctttga tatttggaat cgccggctcg    4860
ccggatgcac tgatatcgcg cattacgtcg gcgctgccgt cagccgcgta gatatgggag    4920
atgagatcgt ggccgaaatc gtgcttgtat ggcgtccacg gggtcacggt gtgaccggct    4980
ttggcgagtg cggcgacggt ggtttccacg ccgcgcagga taggagggtg tggaaggaca    5040
ttgccgtcga agttgtagta gccgatattg agcccgccgt tcttgatctt ggaggcaata    5100
atgtccgact cggactggcg ccagggcatg gggatgacct tggagtcgta tttccatggc    5160
tcctgaccga ggacggattt ggtgaagagg cggaggtcct caacagagtg cgtaatcggc    5220
ccgacaacgc tgtgcaccgt ctcctgaccc tccatgctgt tcgccatctt tgcatacggc    5280
agccgcccat gactcggcct tagaccgtac aggaagttga acgcggccgg cactcgaatc    5340
gagccaccga tatccgttcc tacaccgatg acgccaccac gaatcccaac gatcgcaccc    5400
tcaccaccag aactgccgcc gcacgaccag ttcttgttgc gtgggttgac ggtgcgcccg    5460
atgatgttgt tgactgtctc gcagaccatc agggtctgcg ggacagaggt cttgacgtag    5520
aagacggcac cggctttgcg gagcatggtt gtcagaaccg agtcccttc gtcgtacttg    5580 tttagccatg agatgtagcc cattgatgtt tcgtagccct tgactcgaag ctggtctttg    5640
agagagatgg ggaggccatg gagtggacca acgggtctct tgtgctttgc gtagtattca    5700
tcgagttccc ttgcctgcgc gagagcggcg tcagggaaga actcgtgggc gcagtttgtt    5760
aactgctggg cgattgctgc ccgtttacag aatgctagcg taacttccac cgaggtcaac    5820
tctccggccg ccagcttgga cacaagatct gcagcggagg cctctgtgat cttcagttcg    5880
gcctctgaaa ggatccccga tttctttggg aaatcaataa cgctgtcttc cgcaggcagc    5940
gtctggactt tccattcatc agggatggtt tttgcgaggc gggcgcgctt atcagcggcc    6000
```

```
agttcttccc aggattgagg cattgtatat gagatagttg attgtatgct tggtatagct    6060
tgaaatattg tgcagaaaaa gaaacaagga agaaagggaa cgagaacaat gacgaggaaa    6120
caaaagatta ataattgcag gtctatttat acttgatagc aaagcggcaa acttttttta    6180
tttcaaattc aagtaactgg aaggaaggcc gtataccgtt gctcattaga gagtagtgtg    6240
cgtgaatgaa ggaaggaaaa agtttcgtgt gttcgaagat acccctcatc agctctggaa    6300
caacgacatc tgttggtgct gtctttgtcg ttaattttt cctttagtgt cttccatcat    6360
tttttttgtc attgcggata tggtgagaca acaacggggg agagagaaaa gaaaaaaaaa    6420
gaaaagaagt tgcatgcgcc tattattact tcaatagatg gcaaatggaa aaagggtagt    6480
gaaacttcga tatgatgatg gctatcaagt ctagggctac agtattagtt cgttatgtac    6540
caccatcaat gaggcagtgt aattggtgta gtcttgttta gcccattatg tcttgtctgg    6600
tatctgttct attgtatatc tcccctccgc cacctacatg ttagggagac caacgaaggt    6660
attataggaa tcccgatgta tgggtttggt tgccagaaaa gaggaagtcc atattgtaca    6720
cccggaaaca acaaaaggat ggtaccctgg atggcggcgt tagtatcgaa tcgacagcag    6780
tatagcgacc agcattcaca tacgattgac gcatgatatt actttctgcg cacttaactt    6840
cgcatctggg cagatgatgt cgaggcgaaa aaaatataa atcacgctaa catttgatta    6900
aaatagaaca actacaatat aaaaaaacta tacaaatgac aagttcttga aaacaagaat    6960 cttttttattg tcagtactga ttagaaaaac tcatcgagca tcaaatgaaa ctgcaattta    7020
ttcatatcag gattatcaat accatatttt tgaaaaagcc gtttctgtaa tgaaggagaa    7080
aactcaccga ggcagttcca taggatggca agatcctggt atcggtctgc gattccgact    7140
cgtccaacat caatacaacc tattaatttc ccctcgtcaa aaataaggtt atcaagtgag    7200
aaatcaccat gagtgacgac tgaatccggt gagaatggca aaagcttatg catttctttc    7260
cagacttgtt caacaggcca gccattacgc tcgtcatcaa aatcactcgc atcaaccaaa    7320
ccgttattca ttcgtgattg cgcctgagcg agacgaaata cgcgatcgct gttaaaagga    7380
caattacaaa caggaatcga atgcaaccgg cgcaggaaca ctgccagcgc atcaacaata    7440
ttttcacctg aatcaggata ttcttctaat acctggaatg ctgttttgcc ggggatcgca    7500
gtggtgagta accatgcatc atcaggagta cggataaaat gcttgatggt cggaagaggc    7560
ataaattccg tcagccagtt tagtctgacc atctcatctg taacatcatt ggcaacgcta    7620
cctttgccat gtttcagaaa caactctggc gcatcgggct tcccatacaa tcgatagatt    7680
gtcgcacctg attgcccgac attatcgcga gcccatttat acccatataa atcagcatcc    7740
atgttggaat ttaatcgcgg cctcgaaacg tgagtctttt ccttacccat ggttgtttat    7800
gttcggatgt gatgtgagaa ctgtatccta gcaagatttt aaaaggaagt atatgaaaga    7860
agaacctcag tggcaaatcc taaccttta tatttctcta caggggcgcg gcgtggggac    7920
aattcaacgc gactgtgagg ggagcgtttc cctgctcgca ggtctgcagc gaggagccgt    7980
ggtaccggtt actcaagcac aaactcccaa cactagagtc cactcagctc caattccctt    8040
acaaactcaa tataacaaaa acagagcaga aaacggtcac cactcctatg gttctcccca    8100
aagttattct ccaagacata cgaaacacc tgtggatcct agatataatg ttatcgcaca    8160
gaaaccagca ggcaggccta tacctccagc gccaacccat tataacaact gaacacttc    8220 cgctcaacgg atagcttcct ctcctcctcc cctaattcac aatcaagcag tgcctgcaca    8280
actcttgaag aaagttgcac ctgcttcgtt cgatagcaga gaagatgtac gagacatgca    8340
```

```
agtggccaca cagctatttc ataaccatga tgtaaagggc aaaaaccgac tgacagctga   8400
ggaactacag aacttactac aaaacgacga caactcccat ttttgtatat catcagtaga   8460
tgcgctgata aatttatttg gtgcttccag gtttggcact gtcaaccagg cagaattcat   8520
cgccctatac aaaagagtga aaagttggag aaaagtttat gtggacaatg atatcaacgg   8580
atcgctcacc atttctgtaa gcgaatttca taactcactt caagaactag gatatctaat   8640
acctttgaa gttagcgaga aaacatttga ccaatatgct gagtttataa acagaaatgg    8700
aacaggaaaa gaactaaagt ttgataaatt cgttgaggcg ttagtttggc taatgagatt   8760
aacaaaatta ttcaggaaat tcgatactaa tcaagaaggc attgcaacca tacagtacaa   8820
agattttatc tatgctacat tatatttagg tcgtttccta cctcattgat gaaaaccatt   8880
cgttctttct ggtcgtaata caaatagaag aggtaaacca atcaatggcc cgttagtttg   8940
ccatttgctg catccttccc atgcaaagtg tcttcgtatt tagtgatgtt ttgttagcga   9000
cacaaaagag acctcgatga cagacatttt tttttcttta cttaatgtat tataagtgtg   9060
tctgacctcg actatcatta taatattaat ttgaagttct attttacatt tatatgagtt   9120
attccattac ataataagga tatcaagagc agattagtgt cttttagatt atacatcttt   9180
ttccccccctt ttttgttgtt ggtagtggaa agaaaaggat caattaacag aaataaataa   9240
ataaataata aaaacctaaa attccttttg cgtcattgaa ttttattat gaagtcaaaa    9300
gggagtcggt tgtcaacaga ctgtcctgtc gaatttccca agatagtctc tggattcgct   9360
gaggaagtga aaatacgtag acaaagttcc caaggacagt acgccgtcga ttcacatcct   9420
ccgaaaagcc ctgaactgaa acacagaaga cacgcgtggc cggccttagt caaaaaatta   9480
gccttttaat tctgctgtaa cccgtacatg cccaaaatag ggggcgggtt acacagaata   9540
tataacatcg taggtgtctg ggtgaacagt ttattcctgg catccactaa atataatgga   9600
gcccgctttt taagctggca tccagaaaaa aaagaatcc cagcaccaaa atattgtttt    9660
cttcaccaac catcagttca taggtccatt ctcttagcgc aactacagag aacaggggca   9720
caaacaggca aaaacgggc acaacctcaa tggagtgatg caacctgcct ggagtaaatg    9780
atgacacaag gcaattgacc cacgcatgta tctatctcat tttcttacac cttctattac   9840
cttctgctct ctctgatttg gaaaaagctg aaaaaaaagg ttgaaaccag ttccctgaaa   9900
ttattcccct acttgactaa taagtatata aagacggtag gtattgattg taattctgta   9960
aatctatttc ttaaacttct taaattctac ttttatagtt agtcttttt ttagttttaa    10020
aacaccaaga acttagtttc gaataaacac acataaacaa acaaaatggt tgatggtaga   10080
tcttctgctt ccattgttgc cgttgaccca gaaagagctg ccagagaaag agatgctgct   10140
gccagagctt tgttgcaaga ctctccattg cacaccacca tgcaatacgc tacctctggt   10200
ttggaattga ctgttccata cgctttgaag gttgttgctt ctgctgacac tttcgacaga   10260
gccaaggaag ttgctgatga agtcttgaga tgtgcctggc aattggctga caccgttttg   10320
aactctttca acccaaactc tgaagtctct ttagtcggta gattaccagt cggtcaaaag   10380
catcaaatgt ctgctccatt gaaacgtgtc atggcttgtt gtcaaagagt ctacaactcc   10440
tctgctggtt gtttcgaccc atccactgct ccagttgcca aggctttgag agaaattgct   10500
ttgggtaagg aaagaaacaa tgcttgtttg gaagctttga ctcaagcttg taccttgcca   10560
aactctttcg tcattgattt cgaagctggt actatctcca gaaagcacga acacgcttct   10620
ttggatttgg gtgatgtttc caagggttac atcgtcgatt acgtcattga caacatcaat   10680
gctgctggtt tccaaaacgt tttctttgac tggggtggtg actgtcgtgc ctccggtatg   10740
```

```
aacgccagaa acactccatg ggttgtcggt atcactagac ctccttcctt ggacatgttg    10800
ccaaaccctc caaaggaagc ttcttacatc tccgtcatct ctttggacaa tgaagctttg    10860
gctacctctg gtgattacga aaacttgatc tacactgctg acgataaacc attgacctgt    10920
acctacgatt ggaaaggtaa ggaattgatg aagccatctc aatccaatat cgctcaagtt    10980
tccgtcaagt gttactctgc catgtacgct gacgctttgg ctaccgcttg tttcatcaag    11040
cgtgacccag ccaaggtcag acaattgttg gatggttgga gatacgttag agacaccgtc    11100
agagattacc gtgtctacgt cagagaaaac gaaagagttg ccaagatgtt cgaaattgcc    11160
actgaagatg ctgaaatgag aaagagaaga atttccaaca ctttaccagc tcgtgtcatt    11220
gttgttggtg gtggtttggc tggtttgtcc gctgccattg aagctgctgg ttgtggtgct    11280
caagttgttt tgatggaaaa ggaagccaag ttgggtggta actctgccaa ggctacctct    11340
ggtatcaacg gttggggtac tagagctcaa gctaaggctt ccattgtcga tggtggtaag    11400
tacttcgaaa gagataccta caagtctggt atcggtggta acaccgatcc agctttggtt    11460
aagactttgt ccatgaaatc tgctgacgct atcggttggt tgacttctct aggtgttcca    11520
ttgactgttt tgtcccaatt aggtggtcac tccagaaaga gaactcacag agctccagac    11580
aagaaggatg gtactccatt gccaattggt ttcaccatca tgaaaacttt agaagatcat    11640
gttagaggta acttgtccgg tagaatcacc atcatggaaa actgttccgt tacctctttg    11700
ttgtctgaaa ccaaggaaag accagacggt accaagcaaa tcagagttac cggtgtcgaa    11760
ttcactcaag ctggttctgg taagaccacc attttggctg atgctgttat cttggccacc    11820
ggtggtttct ccaacgacaa gactgctgat tctttgttga gagaacatgc cccacacttg    11880
gttaacttcc caaccaccaa cggtccatgg gctactggtg atggtgtcaa gttggctcaa    11940
agattaggtg ctcaattggt cgatatggac aaggttcaat gcacccaac tggtttgatc    12000 aacccaaagg acccagccaa cccaaccaaa ttcttgggtc cagaagctct aagaggttct    12060
ggtggtgttt tgttgaacaa acaaggtaag agatttgtca cgaattgga tttgagatct    12120 gttgtttcca aggccatcat ggaacaaggt gctgaatacc caggttctgg tggttccatg    12180
tttgcttact gtgtcttgaa cgctgctgct caaaaattgt ttggtgtttc ctctcacgaa    12240
ttctactgga agaagatggg tttgttcgtc aaggctgaca ccatgagaga cttggctgct    12300
ttgattggtt gtccagttga atccgttcaa caaactttag aagaatacga agattatcc    12360 atctctcaaa gatcttgtcc aattaccaga aaatctgttt acccatgtgt tttgggtacc    12420
aaaggtccat actatgtcgc ctttgtcact ccatctatcc actacaccat gggtggttgt    12480
ttgatttctc catctgctga aatccaaatg aagaacactt cttccagagc tccattgtcc    12540
cactccaacc caatcttggg tttattcggt gctggtgaag tcaccggtgg tgtccacggt    12600
ggtaacagat taggtggtaa ctctttgttg gaatgtgttg ttttcggtag aattgccggt    12660
gacagagctt ctaccatttt gcaaagaaag tcctctgctt tgtctttcaa ggtctggacc    12720
actgttgttt tgagagaagt cagagaaggt ggtgtctacg tgctggttc ccgtgtcttg    12780 agattcaact accaggtgc tctacaaaga tctggtctat ccttgggtca attcattgcc    12840
atcagaggtg actgggacgg tcaacaattg attggttact actctccaat cactttgcca    12900
gacgatttgg gtatgattga cattttggcc agatctgaca agggtacttt acgtgaatgg    12960
atctctgctt tggaaccagg tgacgctgtc gaaatgaagg cttgtggtgg tttggtcatc    13020
gaaagaagat tatctgacaa gcacttcgtt ttcatgggtc acattatcaa caagctatgt    13080
```

```
ttgattgctg gtggtaccgg tgttgctcca atgttgcaaa tcatcaaggc cgctttcatg    13140
aagccattca tcgacacttt ggaatccgtc cacttgatct acgctgctga agatgtcact    13200
gaattgactt acagagaagt tttggaagaa cgtcgtcgtg aatccagagg taaattcaag    13260
aaaactttcg ttttgaacag acctcctcca ttatggactg acggtgtcgg tttcatcgac    13320
cgtggtatct tgaccaacca cgttcaacca ccatctgaca acttattggt tgccatctgt    13380
ggtccaccag ttatgcaaag aattgtcaag gccactttaa agactttagg ttacaacatg    13440
aacttggtca gaaccgttga cgaaactgaa ccatctggaa gttaaggtga atttacttta    13500
aatcttgcat ttaaataaat tttctttta tagctttatg acttagtttc aatttatata    13560
ctattttaat gacattttcg attcattgat tgaaagcttt gtgttttttc ttgatgcgct    13620
attgcattgt tcttgtcttt ttcgccacat gtaatatctg tagtagatac ctgatacatt    13680
gtggatgctg agtgaaattt tagttaataa tggaggcgct cttaataatt ttggggatat    13740
tggctttttt ttttaaagtt tacaaatgaa ttttttccgc caggatgggc ccggcgcgcc    13800
gcggccgcga gacctaacta catagtgttt aaagattacg gatatttaac ttacttagaa    13860
taatgccatt ttttgagtt ataataatcc tacgttagtg tgagcgggat ttaaactgtg    13920
aggaccttaa tacattcaga cacttctgcg gtatcaccct acttattccc ttcgagatta    13980
tatctaggaa cccatcaggt tggtggaaga ttaccgttc taagactttt cagcttcctc    14040
tattgatgtt acacctggac acccctttc tggcatccag ttttaatct tcagtggcat    14100 gtgagattct ccgaaattaa ttaaagcaat cacacaattc tctcggatac cacctcggtt    14160
gaaactgaca ggtggtttgt tacgcatgct aatgcaaagg agcctatata cctttggctc    14220
ggctgctgta acaggaata taaagggcag cataatttag gagtttagtg aacttgcaac    14280
atttactatt ttcccttctt acgtaaatat ttttctttt aattctaaat caatctttt    14340 caattttttg tttgtattct tttcttgctt aaatctataa ctacaaaaaa cacatacata    14400
aacaaaaaat gactgatttg aacaaattgg tcaaggaatt gaatgatttg ggtttgactg    14460
acgtcaagga aattgtctac aacccatctt acgaacaatt attcgaagaa gaaaccaagc    14520 caggttttgga aggtttcgac aagggtactt tgaccacttt aggtgctgtt gctgttgaca    14580
ccggtatttt caccggtcgt tctccaaagg acaaatacat tgtttgtgat gaaaccacca    14640
aggacaccgt ctggtggaac tctgaagctg ccaagaacga taacaagcca atgactcaag    14700
aaacctggaa atctttgaga gaattggttg ccaagcaatt gtctggtaag agattattcg    14760
ttgttgacgc tttctgtggt gcttctgaaa agcacagaat tggtgtcaga atggtcactg    14820
aagttgcttg gcaagctcat ttcgtcaaga acatgttcat cagaccaact gacgaagaat    14880
tgaagaactt caaggctgac ttcaccgttt tgaatggtgc caagtgtacc aacccaaact    14940
ggaaggaaca aggtttgaac tctgaaaact ttgttgcttt caacatcact gaaggtatcc    15000
aattgattgg tggtacctgg tacggtggtg aaatgaagaa gggtatgttc tccatgatga    15060
actatttctt gccattgaaa ggtgttgctt ccatgcactg ttctgccaat gtcggtaagg    15120
atggtgacgt tgccatcttc ttcggtctat ccggtactgg taagaccact ctatccactg    15180
acccaaagag acaattgatt ggtgatgacg aacacgttg ggacgaatct ggtgtctttta    15240 actttgaagg tggttgttac gccaagacca tcaacttatc tcaagaaaac gaaccagata    15300
tctacggtgc catccgtcgt gatgctttgt tgaaaacgt tgttgtcaga gctgacggtt    15360
ctgttgactt cgacgacggt tccaagactg aaaaacaccag agtttcttac ccaatctacc    15420
acattgacaa cattgtcaga cctgtttcca aggctggtca cgctaccaag gttatcttct    15480
```

```
tgactgctga tgctttcggt gtcttgccac ctgtttccaa attgactcca gaacaaaccg   15540
aatactactt cttgtccggt ttcactgcca aattggctgg tactgaaaga ggtgtcactg   15600
aaccaactcc aactttctct gcttgtttcg gtgctgcttt cttatctttg cacccaatcc   15660
aatacgctga tgtcttggtt gaaagaatga aggcttctgg tgctgaagct tacttggtca   15720
acaccggttg gaacggtacc ggtaagagaa tctccatcaa ggataccaga ggtatcattg   15780
atgctatctt ggacggttcc attgaaaagg ctgaaatggg tgaattgcca atcttcaact   15840
tggccattcc aaaggctttg ccaggtgttg acccagccat cttagatcca agagacacct   15900
acgctgacaa ggctcaatgg caagtcaagg ctgaagattt ggctaacaga ttcgtcaaga   15960
actttgtcaa atacactgct aacccagaag ctgccaaatt ggttggtgct ggtccaaagg   16020
cttaagcgta cgcaattccg gggaattgtc attctaatat tttatccaca cacacacctt   16080
aaaattttta gattaaatgg catcaactct tagcttcaca cacacacaca caccgaagct   16140
ggttgtttta tttgatttga tataattggt ttctctggat ggtactttttt ctttcttggt   16200 tatttcctat tttaaaatat gaaacgcaca caagtcataa ttattctaat agagcacaat   16260
tcacaacacg cacatttcaa ctttaatatt tttttagaaa cactttattt agtctaattc   16320
ttaattttta atatatataa tgcacacaca ctaatttatt cattaatttt ttattgagta   16380
ggatttgaaa atatttggta tctttgcaag atgtttgtat agagggacaa agaatcgtct   16440
ttattatggt caaggcttta cgtcataata gttcctgccc agctcttcta taatacttta   16500
aagatctctt ctcgtttgct ccatttggaa gtctcgctta cgtttatgcg cccatacaga   16560
cactcaagat acacacttac atgaacgtat acaaatttac taacactact tgaaaatatg   16620
aaccacagta catcatatta agacgtagta ttcgatgatt gaaggccgcc tccgcgaaat   16680
acctttactg attttgccgg ttaatcgcat cgaaatttct tcatcacaag aaagcaaaca   16740
aatcgccagg ccattctaca agtttccttt tcttatgaag atgtaaaagc tactaaggcg   16800
tcattactct agatgactca gtttagtctg accttctata gtatactacc ctggcgctat   16860
gatgatgagc ggttctttta ttgcggaaac gaaaattccg ggaccggcga aatttgcccg   16920
gttttgtccg taaccggctt catgagtcgg cttcaatagt agttgaatac ttatttaaac   16980
agcagaactt aactcactca tcacgctgtt ccgctgaat tttctcaaaa tatctaagca   17040
gtcaacaaat ataagaata ttgaaattga cagttttttgt cgctatcgat ttttattatt   17100
tgctgtttta aatcatggtt tacactccat ccaagggtcc aagaactctt tacgataagg   17160 ttttttgatgc acatgttgtc catcaagatg aaaatggttc cttttgttg tatatcgaca   17220 gacacttggt tcatgaagtc acctctccac aagcttgtcg acggatcccg ggctgcagtc   17280
tagaaactat attgatgaag aaataagatc gtacattttc caagaagaac aacctgatag   17340
gacaaaaatg gttgataata gagtccattg ttgtttgtac tttctgagac cttcaaataa   17400
gggaattgat actttagacg tcgtaacaat gaaaaaatta gcgaagagag tgaatttaat   17460
cccggttatt gctaaatcag atttgctaac gaaagaggaa ttgaaaaact tcaaaacaca   17520
agttagagaa ataataagag tacaagatat ccctgtatgt ttcttttttcg gcgatgaagt   17580 tttgaatgca acacaagata tttttcaaaa atatccattc agtataattg catctaatga   17640 gtacatttttt aatgaaaagg gcgaaaaagt taaaggaaga caatacaaat ggggcgctgt   17700
tgacattgaa aatgaaaagt actgtgactt caaaatcttg caaagacga ttttgattg   17760 gaatttaatt gatcttgtag aaagtaccga ggattattat gaaaaatgca gatcggccat   17820
```

-continued

| | |
|---|---|
| cttggccgat ctgaaatgct aagaactagg ctattaaagg ccagagattg cttaacaacg | 17880 |
| aaaagtgttg acataacgga agaacaaagg aaattttttgg aggaagaaat gaacttcgat | 17940 |
| gaaatcgagg aaaacaaact caaaaattac aagtgctatg aataattaa taaaacggtc | 18000 |
| atggataagg tggctacaga atgggatcct gaatttataa ctagacaatt agaagctaag | 18060 |
| aaaaaattca acgagctgtc caacagagaa atttcaaaat ttcgagactg gaaaagagc | 18120 |
| ctattcatgg aacaagagaa ttttaaccaa gagattgaac aattgaatca caagttggaa | 18180 |
| aacttacaac tggaatgtca ggacttggaa tacaagctgt taatcggaaa agttccaac | 18240 |
| agccattcca cagatagtgc tactttagta aacgttcaca tcaaaaggta gtattaatta | 18300 |
| aaaaaaaaaa aaagccaata | 18320 |

<210> SEQ ID NO 2
<211> LENGTH: 18127
<212> TYPE: DNA
<213> ORGANISM: Artificial Sequence
<220> FEATURE:
<223> OTHER INFORMATION: Plasmid pSUC047

<400> SEQUENCE: 2

| | |
|---|---|
| catcctggcg gaaaaaattc atttgtaaac tttaaaaaaa aaagccaata tccccaaaat | 60 |
| tattaagagc gcctccatta ttaactaaaa tttcactcag catccacaat gtatcaggta | 120 |
| tctactacag atattacatg tggcgaaaaa gacaagaaca atgcaatagc gcatcaagaa | 180 |
| aaaacacaaa gctttcaatc aatgaatcga aaatgtcatt aaaatagtat ataaattgaa | 240 |
| actaagtcat aaagctataa aagaaaatt tatttaaatg caagatttaa agtaaattca | 300 |
| ccttaactgt ccaagatgaa agacttaccc ttttcaatgt tctttctcaa ttccttgaca | 360 |
| gcagtgttga ccaattgttc ttctcttgga gacaattttt ccaaaacaga agtgtcaatg | 420 |
| gaaacaacgg aaccgtttct caaacaatt ggcaaagaga agtattcaat ggagttgtca | 480 |
| ccgactaatt gttgagcctt cttaccgttc ttcaaacctg gcaagtagac gaaagcagac | 540 |
| aaagattcag tttctggctt tcgttgtgg aaagaacgta agacttcttc agcaaatttg | 600 |
| gcaccagcga aagccatgga caaggtagca gaaccggcac cttgcttggc cttgacaatt | 660 |
| tcgtcaccac cgaattggac tctgtggatg aaatgttcgt attgcttgtc caattggaaa | 720 |
| accaaggatt tgtcagtgat gattggaatg atggtttcac cagagtgacc accgatgacg | 780 |
| gtgaccttc tgtgcatggt ggtcttgtct tgttcttgac cgatctttgg gttcttcaac | 840 |
| atcaagtagt caaccaagaa agtttcagct ctgaccaaat ccaagttggt gacacccata | 900 |
| acgttacctg gcttgaactt acccatcttc ttcaaagttt caacggcaat ggaaccaaa | 960 |
| gagttaacag ggttggagat gactaagata cgagcgtttg gggcaaattt accgacagca | 1020 |
| gtaaccaaag acttaacgat accagcgttc atcttgaaca aatcatctct ggtcaaacct | 1080 |
| ggctttcttg gaacaccagc tggaatcaag acaacttgag cattggacaa gtgttttcg | 1140 |
| atggaatcct tgtcgtaacc aacacaagag gagttggtgt tgatgtggga caaatcctta | 1200 |
| ccaataccctt cagcagctct gatatcgtac aaagccaatt cagaaacgta tggagacaat | 1260 |
| ttcaataata gagataatgg ttgaccgaca ccaccagaag cacctaagat ggcaaccta | 1320 |
| accatttgt ttgtttatgt gtgtttattc gaaactaagt tcttggtgtt ttaaaactaa | 1380 |
| aaaaaagact aactataaaa gtagaattta agaagtttaa gaaatagatt tacagaatta | 1440 |
| caatcaatac ctaccgtctt tatatactta ttagtcaagt aggggaataa tttcaggaa | 1500 |
| ctggtttcaa cctttttttt cagcttttc caaatcagag agagcagaag gtaatagaag | 1560 |

```
gtgtaagaaa atgagataga tacatgcgtg ggtcaattgc cttgtgtcat catttactcc    1620
aggcaggttg catcactcca ttgaggttgt gcccgttttt tgcctgtttg tgccctgtt     1680 ctctgtagtt gcgctaagag aatggaccta tgaactgatg gttggtgaag aaaacaatat    1740
tttggtgctg ggattctttt tttttctgga tgccagctta aaaagcgggc tccattatat    1800
ttagtggatg ccaggaataa actgttcacc cagacaccta cgatgttata tattctgtgt    1860
aacccgcccc ctattttggg catgtacggg ttacagcaga attaaaaggc taatttttg     1920 actaaggccg gccacgcgtg aagatctcgt tatgtacccg aatatgtcag tttacattgg    1980
tcagtctatt ggagaattaa gtttgatcgt aggtatagac cggacaatat gccggaatat    2040
gtaaggcaat tgttccaaga tttggaaggt attgatttaa aaagtaataa agtttcaaat    2100
aaatatgata agcaagataa tagcaacggg agtgaaatca atgggggctt ttttgataat    2160
gaggaagggc aggaactcca catgggtcaa aaagcaagtt attttgcaac gacatacaat    2220
tcaagattat ttgacagtaa atactcccaa ttaaaaaaga aattcatgga ctgggatagt    2280
aattcctgga cagatattcc agatgattta aaaatatacc tacagcaaga tgaatcgctt    2340
tagcattaaa aaaccccctt cggtacgtaa tataaaaaat tttataggta atatacatat    2400
ataaaaatac ttcaatcatt tttacaatct tgtatacttt atacaacatg tgaaatcttc    2460
tgcttctgga catcaatatt caaatacagg ccaatcttag gtaaaacatt tggagaaaag    2520
aaggataagg caggacgagg gaagataaat agtttcgtta attataaata catgcagata    2580
aataaaggaa tatcaaatat tatgaataga aaagaagat ggtgagacaa aaagtagta     2640 ataaataggt ccaaatcttc tttatttccc cttcttttc ttatccttt gttttctcca    2700 tattgtataa gaatatattc ttaggaaaat caacagggaa tacagtatag tgattttcgt    2760 tccttttga gcgtaatccc ttcgagactg tgatgttgat tattttgtt gtgatttcaa     2820 aattcttagg ttagttgtat agttcccgtt cataacataa tggatagtaa atgaaaaatc    2880
aaaataaggg tgaaacaaat agacaataaa gatgtagttt tcgaggacga aaaacaaacc    2940
taaccaacaa tgaccttatc accatcgaat tcataagcag gaatttctaa gtttaagggg    3000
gcaggtccct ttctgattct accggaaata tcataatgtg aaccatggca aggacagaac    3060
caaccaccaa aatcaccggc ttcaccaatt ggaacacaac ctaagtgagt acaaataccc    3120
agcataatta accattgagg gtctttgact ctgtcagcat cggtctgtgg gtccttcaaa    3180
gcggacatat ccacactgtt ggcttcctga atttcatgag gagttctgtg tctaatgaac    3240
acaggcttac cttgccattt gacaaccacg ttttaccca atgggatagc cgctaaatta    3300
acttcaactt tagccatagc caaaacatcg gcagtagcgg tcatagatga ataaaggtt    3360 tctacggttg atttggcacc tgcagatgac aaaagaccca tagcaccgac cataaagtaa    3420
gcataagaac ggccttatc agcatcgtta ttttcctta aacgtcatc aaaatttggg       3480 gtcctgtacg tggatttgct agccagcaaa gattgagaaa tcaggtacca cggctcctcg    3540
ctgcagacct gcgagcaggg aaacgctccc ctcacagtcg cgttgaattg tccccacgcc    3600
gcgcccctgt agagaaatat aaaaggttag gatttgccac tgaggttctt ctttcatata    3660 cttccttta aaatcttgct aggatacagt tctcacatca catccgaaca taacaacca     3720 tgggtaagga aaagactcac gtttcgaggc cgcgattaaa ttccaacatg gatgctgatt    3780
tatatgggta taaatgggct cgcgataatg tcggcaatc aggtgcgaca atctatcgat     3840
tgtatgggaa gcccgatgcg ccagagttgt ttctgaaaca tggcaaaggt agcgttgcca    3900
```

```
atgatgttac agatgagatg gtcagactaa actggctgac ggaatttatg cctcttccga    3960
ccatcaagca ttttatccgt actcctgatg atgcatggtt actcaccact gcgatcccg    4020
gcaaaacagc attccaggta ttagaagaat atcctgattc aggtgaaaat attgttgatg   4080
cgctggcagt gttcctgcgc cggttgcatt cgattcctgt ttgtaattgt ccttttaaca   4140
gcgatcgcgt atttcgtctc gctcaggcgc aatcacgaat gaataacggt ttggttgatg   4200
cgagtgattt tgatgacgag cgtaatggct ggcctgttga acaagtctgg aaagaaatgc   4260
ataagctttt gccattctca ccggattcag tcgtcactca tggtgatttc tcacttgata   4320
accttatttt tgacgagggg aaattaatag gttgtattga tgttggacga gtcggaatcg   4380
cagaccgata ccaggatctt gccatcctat ggaactgcct cggtgagttt tctccttcat   4440
tacagaaacg cttttttcaa aaatatggta ttgataatcc tgatatgaat aaattgcagt   4500
ttcatttgat gctcgatgag ttttttctaat cagtactgac aataaaaaga ttcttgtttt   4560
caagaacttg tcatttgtat agttttttta tattgtagtt gttctatttt aatcaaatgt   4620
tagcgtgatt tatattttt ttcgcctcga catcatctgc ccagatgcga agttaagtgc    4680
gcagaaagta atatcatgcg tcaatcgtat gtgaatgctg gtcgctatac tgctgtcgat   4740
tcgatactaa cgccgccatc cagggtacca tccttttgtt gtttccgggt gtacaatatg   4800
gacttcctct tttctggcaa ccaaacccat acatcgggat tcctataata ccttcgttgg   4860
tctccctaac atgtaggtgg cggaggggag atatacaata gaacagatac cagacaagac   4920
ataatgggct aaacaagact acacaaatta cactgcctca ttgatggtgg tacataacga   4980
actaatactg tagccctaga cttgatagcc atcatcatat cgaagtttca ctaccctttt   5040
tccatttgcc atctattgaa gtaataatag gcgcatgcaa cttcttttct tttttttct    5100
tttctctctc ccccgttgtt gtctcaccat atccgcaatg acaaaaaaaa tgatggaaga   5160
cactaaagga aaaaattaac gacaaagaca gcaccaacag atgtcgttgt tccagagctg   5220
atgaggggta tcttcgaaca cacgaaactt tttccttcct tcattcacgc acactactct   5280
ctaatgagca acggtatacg gccttccttc cagttacttg aatttgaaat aaaaaaagtt   5340
tgccgctttg ctatcaagta taaatagacc tgcaattatt aatcttttgt ttcctcgtca   5400
ttgttctcgt tcccttcctt ccttgtttct ttttctgcac aatatttcaa gctataccaa   5460
gcatacaatc aactatctca tatacaatgc ctcaatcctg ggaagaactg gccgctgata   5520
agcgcgcccg cctcgcaaaa accatccctg atgaatggaa agtccagacg ctgcctgcgg   5580
aagacagcgt tattgatttc ccaaagaaat cggggatcct ttcagaggcc gaactgaaga   5640
tcacagaggc ctccgctgca gatcttgtgt ccaagctggc ggccggagag ttgacctcgg   5700
tggaagttac gctagcattc tgtaaacggg cagcaatcgc ccagcagtta acaaactgcg   5760
cccacgagtt cttccctgac gccgctctcg cgcaggcaag ggaactcgat gaatactacg   5820
caaagcacaa gagacccgtt ggtccactcc atggcctccc catctctctc aaagaccagc   5880
ttcgagtcaa gggctacgaa acatcaatgg gctacatctc atggctaaac aagtacgacg   5940
aaggggactc ggttctgaca accatgctcc gcaaagccgg tgccgtcttc tacgtcaaga   6000
cctctgtccc gcagacccty atggtctgcg agacagtcaa caacatcatc gggcgcaccg   6060
tcaacccacg caacaagaac tggtcgtgcg gcggcagttc tggtggtgag ggtgcgatcg   6120
ttgggattcg tggtggcgtc atcggtgtag gaacggatat cggtggctcg attgagtgc   6180
cggccgcgtt caacttcctg tacgtctaag gccgagtca tgggcggctg ccgtatgcaa    6240
agatggcgaa cagcatggag ggtcaggaga cggtgcacag cgttgtcggg ccgattacgc   6300
```

```
actctgttga ggacctccgc ctcttcacca aatccgtcct cggtcaggag ccatggaaat   6360
acgactccaa ggtcatcccc atgccctggc gccagtccga gtcggacatt attgcctcca   6420
agatcaagaa cggcgggctc aatatcggct actacaactt cgacggcaat gtccttccac   6480
accctcctat cctgcgcggc gtggaaacca ccgtcgccgc actcgccaaa gccggtcaca   6540
ccgtgacccc gtggacgcca tacaagcacg atttcggcca cgatctcatc tcccatatct   6600
acgcggctga cggcagcgcc gacgtaatgc gcgatatcag tgcatccggc gagccggcga   6660
ttccaaatat caaagaccta ctgaacccga acatcaaagc tgttaacatg aacgagctct   6720
gggacacgca tctccagaag tggaattacc agatggagta ccttgagaaa tggcgggagg   6780
ctgaagaaaa ggccgggaag gaactggacg ccatcatcgc gccgattacg cctaccgctg   6840
cggtacggca tgaccagttc cggtactatg ggtatgcctc tgtgatcaac ctgctggatt   6900
tcacgagcgt ggttgttccg gttacctttg cggataagaa catcgataag aagaatgaga   6960
gtttcaaggc ggttagtgag cttgatgccc tcgtgcagga agagtatgat ccggaggcgt   7020
accatggggc accggttgca gtgcaggtta tcggacggag actcagtgaa gagaggacgt   7080
tggcgattgc agaggaagtg gggaagttgc tgggaaatgt ggtgactcca taggtcgaga   7140
atttatactt agataagtat gtacttacag gtatatttct atgagatact gatgtataca   7200
tgcatgataa tatttaaacg gttattagtg ccgattgtct tgtgcgataa tgacgttcct   7260
atcaaagcaa tacacttacc acctattaca tgggccaaga aaatattttc gaacttgttt   7320
agaatattag cacagagtat atgatgatat ccgttagatt atgcatgatt cattcctaca   7380 acttttttcgt agcataagga ttaattactt ggatgccaat aaaaaaaaaa aacatcgaga   7440
aaatttcagc atgctcagaa acaattgcag tgtatcaaag taaaaaaaag attttcgcta   7500
catgttcctt ttgaagaaag aaaatcatgg aacattagat ttacaaaaat ttaaccaccg   7560
ctgattaacg attagaccgt taagcgcaca acaggttatt agtacagaga aagcattctg   7620
tggtgttgcc ccggactttc ttttgcgaca taggtaaatc gaataccatc atactatctt   7680
ttccaatgac tccctaaaga aagactcttc ttcgatgttg tatacgttgg agcatagggc   7740
aagaattgtg gcttgagatc tagattacgt ggaagaaagg tagtaaaagt agtagtataa   7800
gtagtaaaaa gaggtaaaaa gagaaaaccg gctacatact agagaagcac gtacacaaaa   7860
actcataggc acttcatcat acgacagttt cttgatgcat tataatagtg tattagatat   7920
tttcagaaat atgcatagaa cctcttcttg cctttacttt ttatacatag aacattggca   7980
gatttactta cactactttg tttctacgcc atttcttttg ttttcaacac ttagacaagt   8040
tgttgagaac cggactacta aaaagcaatg ttcccactga aaatcatgta cctgcaggat   8100 aataacccc taattctgca tcgatccagt atgttttttt ttctctactc attttttacct   8160 gaagatagag cttctaaaac aaaaaaaatc agcgattaca tgcatattgt gtgttctaga   8220
attgcggatc accagatcgc cattacaatg tatgcaggca atatttctc agaatgaaaa   8280 atagagaaaa ggaaacgaaa attctgtaag atgccttcga agagatttct cgatatgcaa   8340
ggcgtgcatc agggtgatcc aaaggaactc gagagagagg gcgaaaggca atttaatgca   8400
ttgcttctcc attgacttct agttgagcgg ataagttcgg aaatgtaagt cacagctaat   8460
gacaaatcca ctttaggttt cgaggcacta tttaggcaaa aagacgagtg gggaaataac   8520
aaacgctcaa acatattagc atataccttc aaaaaatggg aatagtatat aaccttccgg   8580
ttcgttaata aatcaaatct ttcatctagt tctcttaaga tttcaatatt ttgctttctt   8640
```

```
gaagaaagaa tctactctcc tcccccattc gcactgcaaa gctagcttgg cactggccgt   8700
cgttttacaa cgtcgtgact gggaaaaccc tggccttacc caacttaatc gccttgcagc   8760
acatccccct ttcgccagct ggcgtaatag cgaagaggcc cgcaccgatc gcccttccca   8820
acagttgcgc agcctgaatg gcgaatggga aattgtaaac gttaatattt tgttaaaatt   8880
cgcgttaaat ttttgttaaa tcagctcatt ttttaaccaa taggccgaaa tcggcaaaat   8940
cccttataaa tcaaaagaat agaccgagat agggttgagt gttgttccag tttgaacaa    9000 gagtccacta ttaaagaacg tggactccaa cgtcaaaggg cgaaaaaccg tctatcaggg   9060
cgatggccca ctacgtgaac catcacccta atcaagtttt tggggtcga ggtgccgtaa    9120 agcactaaat cggaaccta aagggagccc ccgatttaga gcttgacggg gaaagccggc    9180
gaacgtggcg agaaaggaag ggaagaaagc gaaaggagcg ggcgctaggg cgctggcaag   9240
tgtagcggtc acgctgcgcg taaccaccac acccgccgcg cttaatgcgc cgctacaggg   9300
cgcgtcaggt ggcactttc ggggaaatgt gcgcggaacc cctatttgtt tattttcta    9360 aatacattca aatatgtatc cgctcatgag acaataaccc tgataaatgc ttcaataata   9420
ttgaaaaagg aagagtatga gtattcaaca tttccgtgtc gcccttattc ccttttttgc   9480
ggcattttgc cttcctgttt ttgctcaccc agaaacgctg gtgaaagtaa agatgctga    9540 agatcagttg ggtgcacgag tgggttacat cgaactggat ctcaacagcg gtaagatcct   9600
tgagagtttt cgccccgaag aacgttttcc aatgatgagc acttttaaag ttctgctatg   9660
tggcgcggta ttatcccgta ttgacgccgg gcaagaccaa ctcggtcgcc gcatacacta   9720
ttctcagaat gacttggttg agtactcacc agtcacagaa aagcatctta cggatggcat   9780
gacagtaaga gaattatgca gtgctgccat aaccatgagt gataacactg cggccaactt   9840
acttctgaca acgatcggag gaccgaagga gctaaccgct tttttgcaca acatggggga   9900
tcatgtaact cgccttgatc gttgggaacc ggagctgaat gaagccatac caaacgacga   9960
gcgtgacacc acgatgcctg tagcaatggc aacaacgttg cgcaaactat taactggcga  10020
actacttagt ctagcttccc ggcaacaatt aatagactgg atggaggcgg ataaagttgc  10080
aggaccactt ctgcgctcgg cccttccggc tggctggttt attgctgata atctggagc   10140 cggtgagcgt gggtctcgcg gtatcattgc agcactgggg ccagatggta agccctcccg  10200
tatcgtagtt atctacacga cggggagtca ggcaactatg gatgaacgaa atagacagat  10260
cgctgagata ggtgcctcac tgattaagca ttggtaactg tcagaccaag tttactcata  10320
tatactttag attgatttaa aacttcattt ttaatttaaa aggatctagg tgaagatcct  10380
ttttgataat ctcatgacca aaatccctta acgtgagttt tcgttccact gagcgtcaga  10440
ccccgtagaa aagatcaaag gatcttcttg agatcctttt tttctgcgcg taatctgctg  10500
cttgcaaaca aaaaaaccac cgctaccagc ggtggtttgt ttgccggatc aagagctacc  10560
aactcttttt ccgaaggtaa ctggcttcag cagagcgcag ataccaaata ctgtccttct  10620
agtgtagccg tagttaggcc accacttcaa gaactctgta gcaccgccta catacctcgc  10680
tctgctaatc ctgttaccag tggctgctgc cagtggcgat aagtcgtgtc ttaccgggtt  10740
ggactcaaga cgatagttac cggataaggc gcagcggtcg ggctgaacgg ggggttcgtg  10800
cacacagccc agcttggagc gaacgaccta caccgaactg agatacctac agcgtgagca  10860
ttgagaaagc gccacgcttc ccgaagggag aaaggcggac aggtatccgg taagcggcag  10920
ggtcggaaca ggagagcgca cgagggagct tccaggggga aacgcctggt atctttatag  10980
tcctgtcggg tttcgccacc tctgacttga gcgtcgattt ttgtgatgct cgtcagggg   11040
```

```
gcggagccta tggaaaaacg ccagcaacgc ggccttttta cggttcctgg ccttttgctg    11100
gccttttgct cacatgttct ttcctgcgtt atcccctgat tctgtggata accgtattac    11160
cgcctttgag tgagctgata ccgctcgccg cagccgaacg accgagcgca gcgagtcagt    11220
gagcgaggaa gcggaagagc gcccaatacg caaaccgcct ctccccgcgc gttggccgat    11280
tcattaatgc agctggcacg acaggttttcc cgactggaaa gcgggcagtg agcgcaacgc    11340
aattaatgtg agttagctca ctcattaggc accccaggct ttacacttta tgcttccggc    11400
tcgtatgttg tgtggaattg tgagcggata caatttcac acaggaaaca gctatgacat    11460
gattacgaat ttaatacgac tcacaatagg gaattagctt gcgcgaaatt attggctttt    11520 ttttttttt aattaaaaga aaacattctc tagggattac gaggtaaaga tacattttca    11580
aggcttattc gattctgtga actcagttgg aatattaagg gacaggttgt ttccttgcac    11640
ccagagaagc aatatcgttg agcatgttcg acattgcgta tccttggatg aaagacgtgg    11700
aaaattcaag cagttatgtt tcactccgat gccgtacatt ccgaaactat tttcattgac    11760
atattgtaat catataactg accagtgttc gccggtgcca acttctaatg cattaatgcg    11820
tgatctaacc ccggaaaatc ctttgataaa atacacttta aaaagtggcg cacattctat    11880
tagtaatcct tctccactca ttcctgataa ccctggaagg ttgttatcga gcaaaagcga    11940
ggaaactaca gagttgctgt tggacctgaa ctcattctta aaggtaatt catacgcgag    12000 agatacagaa tgttcaacaa gaggaattga agccattttc caacttcaat ctatccaagg    12060
cagcggtaca tcaagtagaa tgactatgac acccgacttg attgaaaaat ggtttccagg    12120
tgatcggcca tcttggccga tcattctgac gttggtggag gttgggcgcc tgactgtgag    12180
acagaagaga acttgtcaaa tttaacgctg cgatggattt tagcagaggc aatcaaattt    12240
ggtgttaaat tcaaacctgg tgcaatacat gatttcgcta ccaaacacac ttcgattgga    12300
tctttattcg cagacacaca tgattacctt agtttcaact caccaaagaa atgttcccta    12360
ctaggagtga gtgataatga ggatggagcc cgagaggata aatctggcag aaatgagaga    12420
atggaagatt gtctaaaaaa tataaaaagag actagattga gcttgaaaga tgaaaaagaa    12480
aaagtgaagg atgcttttac tcttaaatgt ggacatgcaa ataaatttat gagattggtg    12540
tggtgggtat tggaactgct cccccattgga atacgaatgg aaaataaaga aggaaagtgg    12600
caaaattttc atacacctaa cctcggaaga tcgtcgacaa gcttgtggag aggtgacttc    12660
atgaaccaag tgtctgtcga tatacaacaa aaaggaacca ttttcatctt gatggacaac    12720
atgtgcatca aaaaccttat cgtaaagagt tcttggaccc ttggatggag tgtaaaccat    12780
gatttaaaac agcaaataat aaaaatcgat agcgacaaaa actgtcaatt tcaatattct    12840
ttatatttgt tgactgctta gatattttga gaaaattcag cggaaacagc gtgatgagtg    12900
agttaagttc tgctgtttaa ataagtattc aactactatt gaagccgact catgaagccg    12960
gttacggaca aaaccgggca aatttcgccg gtcccggaat tttcgtttcc gcaataaaag    13020
aaccgctcat catcatagcg ccagggtagt atactataga aggtcagact aaactgagtc    13080
atctagagta atgacgcctt agtagctttt acatcttcat aagaaaagga aacttgtaga    13140
atggcctggc gatttgtttg ctttcttgtg atgaagaaat ttcgatgcga ttaaccggca    13200
aaatcagtaa aggtatttcg cggaggcggc cttcaatcat cgaatactac gtcttaatat    13260
gatgtactgt ggttcatatt ttcaagtagt gttagtaaat ttgtatacgt tcatgtaagt    13320
gtgtatcttg agtgtctgta tgggcgcata aacgtaagcg agacttccaa atggagcaaa    13380
```

```
cgagaagaga tctttaaagt attatagaag agctgggcag gaactattat gacgtaaagc   13440
cttgaccata ataaagacga ttctttgtcc ctctatacaa acatcttgca aagataccaa   13500
atattttcaa atcctactca ataaaaaatt aatgaataaa ttagtgtgtg tgcattatat   13560
atattaaaaa ttaagaatta gactaaataa agtgtttcta aaaaaatatt aaagttgaaa   13620
tgtgcgtgtt gtgaattgtg ctctattaga ataattatga cttgtgtgcg tttcatattt   13680
taaaatagga aataaccaag aaagaaaaag taccatccag agaaaccaat tatatcaaat   13740
caaataaaac aaccagcttc ggtgtgtgtg tgtgtgtgaa gctaagagtt gatgccattt   13800
aatctaaaaa ttttaaggtg tgtgtgtgga taaaatatta gaatgacaat tccccggaat   13860
tgcgtacgct taatccttgg cagaaatcat gtcctcaggt ctaacccatt ggtcgaattc   13920
ttcagaggtc aagtaaccca agatagagc agcttctttc aaagtggtac cttccttgtg   13980
agccttcttg gcacacttgg cagccttgtc gtaaccaatg tgagggttca aagcagtgac   14040
caacatcaaa gattcgttca tgatggagga gatcttcttt tcgttagctt caataccgac   14100
aacacagttc ttggtgaaag agatggaagc gtcagagatt aatctgatgg attggatcaa   14160
gttcttgatc atgactggtt taaagacatt caattcgaat tgaccgttgg aaccagcaac   14220
agagatggca gtgttgttac ccatgacttg agcacaaacc atggtcatag cttcacattg   14280
agttgggttg accttacctg gcatgatgga agaacctggt tcgttttctg gtagagacaa   14340
ttcacctaaa ccacatcttg gaccagaacc caagtaacgg atatcgttgg caatcttcat   14400
caaagaacaa gcaacggtgt tcaaagcacc gtgagcttca accaaagcgt cgtgagcagc   14460
caaagcttcg aatttgtttg gagcggtctt gaatggtaaa ccagtgatgg aagcaatggc   14520
ttcagcaacc ttggcatcga aacccttcct ggtgttcaaa ccagtaccga cagcagtacc   14580
accttgagcc aagttgtata atcttttccaa agtaccttga acacgagcaa taccgtaggt   14640
caattgttga gtgtaaccgg agaattcttg acctaaagtc aatggggtag catcttgcaa   14700
gtgggttcta ccaatcttga tgatgtgttc gaattcagca gatttggctt gcaaagcatc   14760
tctcaaagtg gtcaaagctg gaatcaatct accgtgaatt tcaacaacgg cagcaacgtg   14820
catggcagtt gggaaagtgt cgttggaaga ttgagacatg ttgacatgat cgtttgggtg   14880
gactggagcc ttgaaccta attcaccacc caacaattca atggctctgt tggagatgac   14940
ttcattgacg ttcatcttgg tttgagtacc agaaccggtt tgccagacaa ccaatggaa    15000 atggtcaatc aaagaaccat cgataacttc gtcagcagcc ttttggatgg cttcaccaac   15060
ctttgggtcc aaaccgtagg tcatgttgac ggtggcagca gccttcttca aaacaccgaa   15120
agctctgatt aatggttctg gcattctttc agttggacca ccaatgtcaa agttttgcaa   15180
agatctttga gtttgagcac cccagtaacg gtcagctgga acttgcaagt caccgaaggt   15240
atctctttca gctctgaatt tttgcaaagc agcagaagca gaggacattt tttgtttatg   15300
tatgtgtttt ttgtagttat agatttaagc aagaaaagaa tacaaacaaa aaattgaaaa   15360
agattgattt agaattaaaa agaaaaatat ttacgtaaga agggaaaata gtaaatgttg   15420
caagttcact aaactcctaa attatgctgc cctttatatt ccctgttaca gcagccgagc   15480
caaaggtata taggctccct tgcattagca tgcgtaacaa accacctgtc agtttcaacc   15540
gaggtggtat ccgagagaat tgtgtgattg ctttaattaa tttcggagaa tctcacatgc   15600
cactgaagat taaaaactgg atgccagaaa aggggtgtcc aggtgtaaca tcaatagagg   15660
aagctgaaaa gtcttagaac gggtaatctt ccaccaacct gatgggttcc tagatataat   15720
ctcgaaggga ataagtaggg tgataccgca gaagtgtctg aatgtattaa ggtcctcaca   15780
```

```
gtttaaatcc cgctcacact aacgtaggat tattataact caaaaaaatg gcattattct    15840
aagtaagtta aatatccgta atctttaaac actatgtagt taggtctcgc ggccgcggag    15900
gaaatgagaa atgagaggta tgtaaataga aatagactag ctccacttt aagaattatt    15960 tatgcaatta aatacatggg tgaccaaaag agcgggcgga tacccgcgtc accacaagca    16020
gaataaaagg taaacctgaa attgttttaa cataaaatga aaaatgcttg tttgcaaccc    16080
tatatagaat cataaaacat tcgtgactat aaaatgaata aactaaacta ttctaagaaa    16140
atgaaataaa tgacaaaaaa acgtgttttt tggactagaa ggcttaatca aaagctctta    16200
aacgctttcg tgttcagaag atggaggatc agattcacca ccagtggaag taacgtgggt    16260
gtcaaccttt tccaaagaag ctggagcctt ttctggtggg aaagttgggt tcaaaacacc    16320
agtgtttggc tttggaggtg ggtgagcatc ttcatcctta cctgggtaac acaaatcgtt    16380
gaccaagaaa gctctgacca tcaagtacat caacaagatc cattggatac ataggatgac    16440
accgatgatg tgaccgaaca tttgaaggc cttggagtca atcatcttac caatttcaat    16500
ggtacagtta acgaaaccga cgtttgggaa gatgaaagca aaccaaccac aagcaaattt    16560
caatggagct ctggtgaaga aaccagccaa gaaagaaacc atggccaaac agtaacacca    16620
agcagccaaa ccccagatga aaatggccat gaaagtggaa acgaaaccca gtattcaga    16680 agaattggca ccgacgaaaa tgtatggtct ggaacccata gcaccacggg caatgttgat    16740
caaagccaaa ccggagaaag ctggtggacc aacaaacatg aacatacctg gtctgtcttg    16800
aggcttggcc aaaccaacgg tgaagaatct caaaacgttg acagcaaaca acaacaagta    16860
aacccagaaa cccaaaacctt ggaataagat accgaagata accatgttct tcaattggtg    16920
agctggttga gtggagttga cagcaccagc aatgacacca cagatcattg gtgggaaaat    16980
tggtaagatc caagctggag aagcagtttc aatggtgtaa acgtggttgt tgaaaatggt    17040
gaagaaagcc atgacacagt agatgaaaga gacagcaacg tagatgtagt ataagattct    17100
gataacccag accatccatt caccagtgtc tgggtaagcg tagatggcca acatgtcaat    17160
gaaagtggag atggatagca aacaggtagc aatgaataat ttttccaagt ggtggttcca    17220
ggagtccttg atggtagatg ggtatttgat gaatctgaac aacatacaag aaccaaacaa    17280
agagaataag aagatttgta agatgtagac aatcttacca atggtgttca aaccgtagaa    17340
tctgaatggg aaagaaccaa tgatcaaacc gacaccacca gtggccatgg tacaagcaaa    17400
ccaggaccag gtgaaatgct tcaatctttg agacaatgga acgtgtggag ccttgacgtt    17460
ccagtccaac aattcatggt aacgttgctt caagatttcc ttcaattcac ccatttgtt    17520 ttagtgtttg tgtgttgata agcagttgct tggtttttta tgaaaatag ctagaaggaa    17580 taagggatta caagagagat gttacaagaa agaagtaaaa taaatttgat taatattgcc    17640
attatcaaaa gctatttata tgttgaaatc gtggagatca tgtgtgccag aaaaggccac    17700
agtttccggg gagaggcata ccttgaggtg gctaggaatc acgagacct cttgacttgc    17760 agggtaggct agctagaatt aagtgaggtg acaaggtttc catacagttt tgaccttgag    17820
acgttgctac ttacgatttg cagtatgcaa gtctcatgct gcaaacaaaa gaggaccgct    17880
caggtaatcg ctcaattagt ggacgttatc aggggcggga gaggcgaaag tggttttgg    17940 tggtgtaagt aaaggtcgtc caaatatgca ggtgtttggg tgctatccta gtggaagctc    18000
ggatcagtag ataacccgcc tagaagcggt attttctttt ttttctttc cttctttc    18060 gtcattattt caaacgcttt tgcgtcaagt aatgaatatc tggcggttcc gcggggcgcg    18120
``` ccgggcc 18127

<210> SEQ ID NO 3
<211> LENGTH: 12279
<212> TYPE: DNA
<213> ORGANISM: Artificial Sequence
<220> FEATURE:
<223> OTHER INFORMATION: Plasmid pSUC091

<400> SEQUENCE: 3

```
aagcttgcat gcctgcaggt cgacggcgcg ccgggcccgt ttaaacggcc ggccaaggtg     60
agacgcgcat aaccgctaga gtactttgaa gaggaaacag caatagggtt gctaccagta    120
taaatagaca ggtacataca acactggaaa tggttgtctg tttgagtacg ctttcaattc    180
atttgggtgt gcactttatt atgttacaat atggaaggga actttacact tctcctatgc    240
acatatatta attaaagtcc aatgctagta gagaaggggg gtaacacccc tccgcgctct    300
tttccgattt ttttctaaac cgtggaatat ttcggatatc cttttgttgt ttccgggtgt    360
acagggtaat aactgatata attaaattga agctctaatt tgtgagttta gtatacatgc    420
atttacttat aatacagttt tttagttttg ctggccgcat cttctcaaat atgcttccca    480
gcctgctttt ctgtaacgtt caccctctac cttagcatcc cttcctttg caaatagtcc     540
tcttccaaca ataataatgt cagatcctgt agagaccaca tcatccacgg ttctatactg    600
ttgacccaat gcgtctccct tgtcatctaa acccacaccg ggtgtcataa tcaaccaatc    660
gtaaccttca tctcttccac ccatgtctct tgagcaata aagccgataa caaaatcttt     720
gtcgctcttc gcaatgtcaa cagtaccctt agtatattct ccagtagata gggagccctt    780
gcatgacaat tctgctaaca tcaaaaggcc tctaggttcc tttgttactt cttctgccgc    840
ctgcttcaaa ccgctaacaa tacctgggcc caccacaccg tgtgcattcg taatgtctgc    900
ccattctgct attctgtata cacccgcaga gtactgcaat ttgactgtat taccaatgtc    960
agcaaatttt ctgtcttcga agagtaaaaa attgtacttg gcggataatg cctttagcgg   1020
cttaactgtg ccctccatgg aaaaatcagt caagatatcc acatgtgttt ttagtaaaca   1080
aattttggga cctaatgctt caactaactc cagtaattcc ttggtggtac gaacatccaa   1140
tgaagcacac aagtttgttt gcttttcgtg catgatatta aatagcttgg cagcaacagg   1200
actaggatga gtagcagcac gttccttata tgtagctttc gacatgattt atcttcgttt   1260
cctgcaggtt tttgttctgt gcagttgggt taagaatact gggcaattc atgtttcttc    1320
aacactacat atgcgtatat ataccaatct aagtctgtgc tccttccttc gttcttcctt   1380
ctgttcggag attaccgaat caaaaaaatt tcaaagaaac cgaaatcaaa aaaagaata    1440
aaaaaaaaat gatgaattga attgaaaagc tgtggtatgg acgcgtgcgg ccgcggatcc   1500
acgctgacat ggtttcttta ggtttgatga ggccgtcttt tgttgatagc agcttttcc    1560
atttttttt ttttgtttc gagtaacgta tggtttagta tctgtcttct ccttctctta    1620
caaaaaaacc ctttgtaaaa tagtgccgag ttggaggaca tcaatctgat gggcaagaaa   1680
acaccaaccc ccctatatg aaaagaaaat gataagcaga tagataaaaa tacttaatta   1740
actaatacat aaaaataaga ggtatataaa aatattatat ggaagcaata attattactc   1800
cttacttctt ttgggatgga ggcaaagttt cttcttccaa gacaaccaac aaatcagaag   1860
catcgacgga ttcaccatct ttgatgaaaa cgtccttgac ttgaccgtca gctggagaag   1920
agacaaccat ttccatcttc atagcggaca aaacagcaat agattcaccc ttcttgacca   1980
aggaacccct gtggaccttg acttcgatga taacaccagc cattggagca ccgatttggt   2040
```

-continued

```
gggtgtcgtg aacatcagcc tttggcttgg caacggattg gatgttttga gatttgtcag    2100
caactctgat ctttctcaat tcaccgttta attcgaagta gacttctctt tgaccggttt    2160
tcttgttcaa gtcaccaaca gcttgtaatt tgatgatcaa agtcttacct tgttcaatgg    2220
tgacttcaat ttcttcatct ggttcagctg gggccaaaaa gttcttggtt ggtaagacgg    2280
acaaatcacc gtaggtttct ctgatctttt ggaaatcttc gtaaactctt gggtacatgt    2340
tgtaagaagc aacatcacat tcgtcaatat caccgaatct gttttgcaaa tcttctctga    2400
tcttttccaa gtcaaatggt tccaattcca aacctggtct acaagtcaac tttcttctct    2460
tgtttcttaa gacgtcagaa cgtaatggtt ctgggaaacc accgtatggt tgaccgatca    2520
aaccttcaaa gaagtccatg acggaatctg ggaagtctag agagttagcc aatcttctga    2580
tgtcatcaga ggttaatttg ttgctgacca tgaattgggc caagtcacca acaaccttgg    2640
aggttggagt aaccttgaca atgtcaccca acaagtagtt ggcttctctg taagctctct    2700
tggtttcagc ccattgttca cctaaaccca attgttgagc ttggaacaat aagttggtca    2760
attgaccacc tggaatttcg tgttggtaga cttctgggtc tggacccttc aagtcagctt    2820
cgaaacaaga gtacaataat ctcatttcag cccagtaagc atctaattct ctaacgtgtt    2880
cgacgttgat accggtgtcg atgttacctt ccaaggaggc caacaaagcg ttaatggatg    2940
gttgagaggt caaaccagac atggagttga tggcaacatc gacgcatca gcaccagcca     3000 aagcacaagc agtcatggaa gcaacggcag taccggcaga atcgtgagag tggacgtgaa    3060
ttggcaaatc tgggtatctg gttctcaaag aaccgatcaa caacttagca gcagctggct    3120
tcatggtacc agccatgtcc ttgataccta agatgtgggt acccatttgg acgatctttt    3180
caacaacttc caagtagtag tccaagttgt acttcttacc aggttgcaac atgtcaccgg    3240
agtaacaaac ggtagcttca acaacaccac cagccttctt gacagcgtta acaccgacct    3300
ttaattgttc caagtcattc aaagcatcga aaactctgaa gatgtcaaca ccgttgtcct    3360
tagcttgctt gacgaagtgg tcaatggcat tgtctggtaa agaagagtaa gcaacaccgt    3420
tagcacctct tagcaacatt tggaatgaaa tgtttggaac caaagatctc aactttctta    3480
gtctttccca tgggtcctcg tgcaagaatc tcatggcgac atcgaaggtg gcaccacccc    3540
aacattccaa ggcgaaagca ccggccaagg catgagcggt ggttggagcg atagtagcca    3600
aatcgtgggt tctaactctg gtagccaata aagattggtg agcatctctc caggtggtgt    3660
ccatcaacaa gtaccgttg aattgtctga cttgcttggc aaattcagat ggacccttt     3720 ccaacaaaac ttgtctccaa ccagatggtg gagcagattt agtaacgttg atgacgttac    3780
cttgagcgtc gtgcaagtgt ggaacggaag ggttagattt caactttggt aaaccaattt    3840
gacccttgat agaagaaccg ttgacagcca aatcagccaa gtagtgcaac aatttttgag    3900
ctctgttttg agaggaaacc atttggaaca attgtggagt gtcgtcaatg aaagtggtcc    3960
agtaagtacc ttcaatgaaa acaggggtgg tcaacaaagt caacaaaaat ggaatgttgg    4020
tcttaacacc tctgattctg aattcgatca aagctctgat catctttctt ctgacaattt    4080
cgtaagtgga accggaacag gaacatttga ccaacatgga gtcgtagtga ggagagatag    4140
tagcaccagc gtaagcgtta ccaccatcca atctgacacc gttaccacca gcagatctgt    4200
aaacttccaa acgaccggtg tctggttgga agttcttgga tgggtcctcg gtagtgatac    4260
gacattggat ggagaaacct ctagtggtga tcttgtcttg caacaaaccc aattgagtca    4320
aagtggcacc agcagcaatt tggatttgag cagagacaat gtcaatacca gtgatttctt    4380
```

```
cagtgatagt gtgttcgact tgaattcttg ggttaatttc gatgaaataa tgtctgtttt    4440
ggttgtcaac caagaattca gcagtaccag cgtttctgta accacaaacc ttagctaatt    4500
tgacagcgtc agtcaagata gcatcacgga cttctcttgg taaagtcttg gctggagcaa    4560
cttcaacaac cttttggtga cgacgttgaa cagaacagtc tctttcgaac aaatggacaa    4620
cgttaccgtg gttgtcagcc aacaattgaa cttcaatgtg ctttggcttg tccaagaatc    4680
tttcgacgaa acaggtaccg ttaccgaaag cagttctggc ttcagaggta gctctttgga    4740
aagcatcagc aacgtcatca ccttctctaa caactctcat accacgacca ccaccaccga    4800
aagcggcctt gatgataact gggtaaccgt attcattgac gaaatccaag gcttcttgaa    4860
cagtttcaat tggacctgga gtacctggaa cagttgggac attggcacga gcagccaaat    4920
gacgagcaga gactttgtca ccgacagagt caatgacttc agctggtgga ccgatccaag    4980
tgataccagc cttgacaacc ttgtcagcaa attcagagtt ttcggacaag aaaccgtaac    5040
ctgggtggat gaaatcgacc ttgtgcttct tggcaatttc aataatttcg tccatggcca    5100
agtaggcacc aactggagtg tattgacctt cttccaccaat aacgtaagcc tcatcagcct    5160
tcaatctgtg catggacaaa cgatcttcat gagagtagat agcaatggtt ctcatggata    5220
gttcatgagc agatctgaaa attctgattg ggatttcacc tctgttagca accaagattt    5280
tgttcttttc acccaacaaa gagaagttgt ctctcaaacc ggccaatttc ttggaagagg    5340
acatgtttag ttaattatag ttcgttgacc gtatattcta aaaacaagta ctccttaaaa    5400
aaaaaccttg aagggaataa acaagtagaa tagatagaga gaaaaataga aaatgcaaga    5460
gaatttatat attagaaaga gagaaagaaa aatggaaaaa aaaaaatagg aaaagccaga    5520
aatagcacta gaaggagcga caccagaaaa gaaggtgatg gaaccaattt agctatatat    5580
agttaactac cggctcgatc atctctgcct ccagcatagt cgaagaagaa ttttttttt     5640 cttgaggctt ctgtcagcaa ctcgtatttt ttctttcttt tttggtgagc ctaaaaagtt    5700
cccacgttct cttgtacgac gccgtcacaa acaaccttat gggtaatttg tcgcggtctg    5760
ggtgtataaa tgtgtgggtg caacatgaat gtacggaggt agtttgctga ttggcggtct    5820
atagatacct tggttatggc gccctcacag ccggcagggg aagcgcctac gcttgacatc    5880
tactatatgt aagtatacgg ccccatatat atatatatat atatacatta aacattattg    5940
gtaagggccc ggccggccaa gctttagagc tcatggcgcg cctaggtaaa aaaataagt     6000 gtatacaaat tttaaagtga ctcttaggtt ttaaaacgaa aattcttatt cttgagtaac    6060
tctttcctgt aggtcaggtt gctttctcag gtatagcatg aggtcgctct tattgaccac    6120
acctctaccg gcatgccgag caaatgcctg caaatcgctc cccatttcac ccaattgtag    6180
atatgctaac tccagcaatg agttgatgaa tctcggtgtg tatttatgt cctcaggaga    6240 caacacctgt tgtaatcgtt cttccacacg gatccacagc ctagccttca gttgggctct    6300
atcttcatcg tcattcattg catctactag ccccttacct gagcttcaag acgttatatc    6360
gcttttatgt atcatgatct tatcttgaga tatgaataca taaatatatt tactcaagtg    6420
tatacgtgca tgcttttttt acggtttaaa catttaaatg ggccgctcta gaggatcccc    6480
gggtaccgag ctcgggccca cgcgctactag ttccggtaat ttgaaaacaa acccggtctc    6540
gaagcggaga tccggcgata attaccgcag aaataaaccc atacacgaga cgtagaacca    6600
gccgcacatg gccggagaaa ctcctgcgag aatttcgtaa actcgcgcgc attgcatctg    6660
tatttcctaa tgcggcactt ccaggcctcg agacctctga catgctttg acaggaatag    6720 acattttcag aatgttatcc atatgccttt cgggtttttt tccttccttt tccatcatga    6780
```

```
aaaatctctc gagaccgttt atccattgct tttttgttgt cttttccct cgttcacaga   6840 aagtctgaag aagctatagt agaactatga gcttttttg tttctgtttt cctttttttt   6900 tttttacct ctgtggaaat tgttactctc acactcttta gttcgtttgt ttgttttgtt   6960
tattccaatt atgaccggtg acgaaacgtg gtcgatggtg ggtaccgctt atgctcccct   7020
ccattagttt cgattatata aaaggccaa atattgtatt attttcaaat gtcctatcat   7080
tatcgtctaa catctaatt ctcttaaatt ttttctcttt ctttcctata acaccaatag    7140
tgaaaatctt ttttcttct atatctacaa aacttttt tttctatcaa cctcgttgat     7200
aaattttttc tttaacaatc gttaataatt aattaattgg aaaataacca ttttttctct   7260
cttttataca cacattcaaa agaaagaaaa aaaatatacc ccagctagtt aaagaaaatc   7320
attgaaaaga ataagaagat aagaaagatt taattatcaa acaatatcaa tatgcctcaa   7380
tcctgggaag aactggccgc tgataagcgc gcccgcctcg caaaaaccat ccctgatgaa   7440
tggaaagtcc agacgctgcc tgcggaagac agcgttattg atttcccaaa gaaatcgggg   7500
atcctttcag aggccgaact gaagatcaca gaggcctccg ctgcagatct tgtgtccaag   7560
ctggcggccg gagagttgac ctcggtggaa gttacgctag cattctgtaa acgggcagca   7620
atcgcccagc agttaacaaa ctgcgcccac gagttcttcc ctgacgccgc tctcgcgcag   7680
gcaagggaac tcgatgaata ctacgcaaag cacaagagac ccgttggtcc actccatggc   7740
ctccccatct ctctcaaaga ccagcttcga gtcaagggct acgaaacatc aatgggctac   7800
atctcatggc taaacaagta cgacgaaggg gactcggttc tgacaaccat gctccgcaaa   7860
gccggtgccg tcttctacgt caagacctct gtcccgcaga ccctgatggt ctgcgagaca   7920
gtcaacaaca tcatcgggcg caccgtcaac ccacgcaaca agaactggtc gtgcggcggc   7980
agttctggtg gtgagggtgc gatcgttggg attcgtggtg gcgtcatcgg tgtaggaacg   8040
gatatcggtg gctcgattcg agtgccggcc gcgttcaact tcctgtacgg tctaaggccg   8100
agtcatgggc ggctgccgta tgcaaagatg gcgaacagca tggagggtca ggagacggtg   8160
cacagcgttg tcgggccgat tacgcactct gttgaggacc tccgcctctt caccaaatcc   8220
gtcctcggtc aggagccatg gaaatacgac tccaaggtca tccccatgcc ctggcgccag   8280
tccgagtcgg acattattgc ctccaagatc aagaacggcg ggctcaatat cggctactac   8340
aacttcgacg gcaatgtcct tccacaccct cctatcctgc gcggcgtgga aaccaccgtc   8400
gccgcactcg ccaaagccgg tcacaccgtg accccgtgga cgccatacaa gcacgatttc   8460
ggccacgatc tcatctccca tatctacgcg gctgacggca gcgccgacgt aatgcgcgat   8520
atcagtgcat ccggcgagcc ggcgattcca aatatcaaag acctactgaa cccgaacatc   8580
aaagctgtta acatgaacga gctctgggac acgcatctcc agaagtggaa ttaccagatg   8640
gagtaccttg agaaatggcg ggaggctgaa gaaaaggccg ggaaggaact ggacgccatc   8700
atcgcgccga ttacgcctac cgctgcggta cggcatgacc agttccggta ctatgggtat   8760
gcctctgtga tcaacctgct ggatttcacg agcgtggttg ttccggttac ctttgcggat   8820
aagaacatcg ataagaagaa tgagagtttc aaggcggtta gtgagcttga tgccctcgtg   8880
caggaagagt atgatccgga ggcgtaccat ggggcaccgg ttgcagtgca ggttatcgga   8940
cggagactca gtgaagagag gacgttggcg attgcagagg aagtggggaa gttgctggga   9000
aatgtggtga ctccataggt cgagaattta tacttagata agtatgtact tacaggtata   9060
tttctatgag atactgatgt atacatgcat gataatattt aaacggttat tagtgccgat   9120
```

```
tgtcttgtgc gataatgacg ttcctatcaa agcaatacac ttaccaccta ttacatgggc    9180
caagaaaata ttttcgaact tgtttagaat attagcacag agtatatgat gatatccgtt    9240
agattatgca tgattcattc ctacaacttt ttcgtagcat aaggattaat tacttggatg    9300
ccaataaaaa aaaaaaacat cgagaaaatt tcagcatgct cagaaacaat tgcagtgtat    9360
caaagtaaaa aaaagatttt cgctacatgt tccttttgaa gaaagaaaat catggaacat    9420
tagatttaca aaaatttaac caccgctgat taacgattag accgttaagc gcacaacagg    9480
ttattagtac agagaaagca ttctgtggtg ttgccccgga ctttcttttg cgacataggt    9540
aaatcgaata ccatcatact atcttttcca atgactccct aaagaaagac tcttcttcga    9600
tgttgtatac gttggagcat agggcaagaa ttgtggcttg agatgaattc actggccgtc    9660
gttttacaac gtcgtgactg ggaaaaccct ggcgttaccc aacttaatcg ccttgcagca    9720
catccccctt tcgccagctg gcgtaatagc gaagaggccc gcaccgatcg cccttcccaa    9780
cagttgcgca gcctgaatgg cgaatggcgc ctgatgcggt attttctcct tacgcatctg    9840
tgcggtattt cacaccgcat atggtgcact ctcagtacaa tctgctctga tgccgcatag    9900
ttaagccagc cccgacaccc gccaacaccc gctgacgcgc cctgacgggc ttgtctgctc    9960
ccggcatccg cttacagaca agctgtgacc gtctccggga gctgcatgtg tcagaggttt    10020
tcaccgtcat caccgaaacg cgcgagacga agggcctcg tgatacgcct atttttatag    10080
gttaatgtca tgataataat ggtttcttag acgtcaggtg gcacttttcg gggaaatgtg    10140
cgcggaaccc ctatttgttt atttttctaa atacattcaa atatgtatcc gctcatgaga    10200
caataaccct gataaatgct tcaataatat tgaaaaagga agagtatgag tattcaacat    10260
ttccgtgtcg cccttattcc cttttttgcg cattttgcc ttcctgtttt tgctcaccca    10320
gaaacgctgg tgaaagtaaa agatgctgaa gatcagttgg gtgcacgagt gggttacatc    10380
gaactggatc tcaacagcgg taagatcctt gagagttttc gccccgaaga acgttttcca    10440
atgatgagca cttttaaagt tctgctatgt ggcgcggtat tatcccgtat tgacgccggg    10500
caagagcaac tcggtcgccg catacactat tctcagaatg acttggttga gtactcacca    10560
gtcacagaaa agcatcttac ggatggcatg acagtaagag aattatgcag tgctgccata    10620
accatgagtg ataacactgc ggccaactta cttctgacaa cgatcggagg accgaaggag    10680
ctaaccgctt ttttgcacaa catgggggat catgtaactc gccttgatcg ttgggaaccg    10740
gagctgaatg aagccatacc aaacgacgag cgtgacacca cgatgcctgt agcaatggca    10800
acaacgttgc gcaaactatt aactggcgaa ctacttactc tagcttcccg gcaacaatta    10860
atagactgga tggaggcgga taaagttgca ggaccacttc tgcgctcggc ccttccggct    10920
ggctggttta ttgctgataa atctggagcc ggtgagcgtg ggtctcgcgg tatcattgca    10980
gcactggggc cagatggtaa gccctcccgt atcgtagtta tctacacgac ggggagtcag    11040
gcaactatgg atgaacgaaa tagacagatc gctgagatag gtgcctcact gattaagcat    11100
tggtaactgt cagaccaagt ttactcatat atactttaga ttgatttaaa acttcatttt    11160
taatttaaaa ggatctaggt gaagatcctt tttgataatc tcatgaccaa aatcccttaa    11220
cgtgagtttt cgttccactg agcgtcagac cccgtagaaa agatcaaagg atcttcttga    11280 gatcctttt ttctgcgcgt aatctgctgc ttgcaaacaa aaaaaccacc gctaccagcg    11340
gtggtttgtt tgccggatca agagctacca actctttttc cgaaggtaac tggcttcagc    11400
agagcgcaga taccaaatac tgtccttcta gtgtagccgt agttaggcca ccacttcaag    11460
aactctgtag caccgcctac atacctcgct ctgctaatcc tgttaccagt ggctgctgcc    11520
```

```
agtggcgata agtcgtgtct taccggggttg gactcaagac gatagttacc ggataaggcg    11580
cagcggtcgg gctgaacggg gggttcgtgc acacagccca gcttggagcg aacgacctac    11640
accgaactga gatacctaca gcgtgagcta tgagaaagcg ccacgcttcc cgaagggaga    11700
aaggcggaca ggtatccggt aagcggcagg gtcggaacag gagagcgcac gagggagctt    11760
ccagggggaa acgcctggta tctttatagt cctgtcgggt ttcgccacct ctgacttgag    11820
cgtcgatttt tgtgatgctc gtcagggggg cggagcctat ggaaaaacgc cagcaacgcg    11880
gcctttttac ggttcctggc cttttgctgg ccttttgctc acatgttctt tcctgcgtta    11940
tcccctgatt ctgtggataa ccgtattacc gcctttgagt gagctgatac cgctcgccgc    12000
agccgaacga ccgagcgcag cgagtcagtg agcgaggaag cggaagagcg cccaatacgc    12060
aaaccgcctc tccccgcgcg ttggccgatt cattaatgca gctggcacga caggtttccc    12120
gactggaaag cgggcagtga gcgcaacgca attaatgtga gttagctcac tcattaggca    12180
ccccaggctt tacactttat gcttccggct cgtatgttgt gtggaattgt gagcggataa    12240
caatttcaca caggaaacag ctatgaccat gattacgcc                           12279
```

<210> SEQ ID NO 4
<211> LENGTH: 14722
<212> TYPE: DNA
<213> ORGANISM: Artificial Sequence
<220> FEATURE:
<223> OTHER INFORMATION: Plasmid pSUC111

<400> SEQUENCE: 4

```
ggccccccct cgaggtcgac ggtatcgata agcttgatat cgaattcctg cagcccgggg      60
gatcccttcc cttttacagt gcttcggaaa agcacagcgt tgtccaaggg aacaatttt     120 cttcaagtta atgcataaga aatatctttt tttatgttta gctaagtaaa agcagcttgg     180
agtaaaaaaa aaaatgagta aatttctcga tggattagtt tctcacaggt aacataacaa     240
aaaccaagaa aagcccgctt ctgaaaacta cagttgactt gtatgctaaa gggccagact     300
aatgggagga gaaaaagaaa cgaatgtata tgctcattta cactctatat caccatatgg     360
aggataagtt gggctgagct tctgatccaa tttattctat ccattagttg ctgatatgtc     420
ccaccagcca acacttgata gtatctactc gccattcact tccagcagcg ccagtagggt     480
tgttgagctt agtaaaaatg tgcgcaccac aagcctacat gactccacgt cacatgaaac     540
cacaccgtgg ggccttgttg cgctaggaat aggatatgcg acgaagacgc ttctgcttag     600
taaccacacc acattttcag ggggtcgatc tgcttgcttc ctttactgtc acgagcggcc     660
cataatcgcg cttttttttt aaaggcgcg agacagcaaa caggaagctc gggtttcaac     720
cttcggagtg gtcgcagatc tggagactgg atctttacaa tacagtaagg caagccacca     780
tctgcttctt aggtgcatgc gacggtatcc acgtgcagaa caacatagtc tgaagaaggg     840
ggggaggagc atgttcattc tctgtagcag taagagcttg gtgataatga ccaaaactgg     900
agtctcgaaa tcatataaat agacaatata ttttcacaca atgagatttg tagtacagtt     960
ctattctctc tcttgcataa ataagaaatt catcaagaac ttggtttgat atttcaccaa    1020
cacacacaaa aacagtact tcactaaatt tacacacaaa acaaaatggt ttccgtcaag    1080
gcttctgctg ctgaaaagaa ggaattcttg caatctcaaa tcgatgaaat tgaaaaatgg    1140
tggtctgaac caagatggaa ggacaccaag agaatctact ctgcttacga aattgccaag    1200
cgtcgtggtt ctgtcaagcc aaacactttc ccatctaccg tcatgtctca aaaattgttc    1260
```

```
aagatcttag gtgaacacgc taagaacggt actgtttcca agactttcgg tgctttggac    1320
cctgttcaag tcactcaaat gtccaagtac ttggacacca tctacgtttc cggttggcaa    1380
tgttcctcta ctgcttccac ttctaacgaa ccaggtccag atttggctga ctacccaatg    1440
gacaccgttc caaacaaggt tgaacatttg ttcaaggctc aacaattcca cgacagaaag    1500
caatgggaaa gaatctgtga tggtaccatt gaagaatctg aaatcattga ctacttgact    1560
ccaattgttg ctgatggtga tgctggtcac ggtggtttga ctgctgtctt caagttgacc    1620
aagatgttca tcgaaagagg tgctgctggt attcacattg aagatcaaac ctctaccaac    1680
aagaaatgtg gtcacatggc tggtagatgt gtcattccag ttcaagaaca catcaacaga    1740
ttaatcacct gtagaatggc tgctgatgtc ttgggttctg acttgatctt agtcgccaga    1800
actgactctg aagctgctac tttgttgtcc tccactgctg actctcgtga ccattatttc    1860
atcttaggtg cttccaaccc agctgtcaag ggtaagcctt tgaatgactt gttgaacaag    1920
gccatcttgg atggtgctac catcgatgac ttgcaaacca ttgaaaagga atggttagcc    1980
aaggctgatg tcaaattatt ccacgaagtt ttcgctgatg ctgccaaggc tgctggtaag    2040
gaccaatctg tcattgacca attcaactcc aaggttaacc cattgtctga aacctccatc    2100
tacgaaatgc aagctttggc caaggaattg ttgggtactg aattgttctt cgactgggac    2160
ttgccaagag gtagagaagg tctatacaga taccaaggtg gtactcaatg ttctgttatg    2220
agagccagag cctttgctcc atacgctgat ctatgttgga tggaatccaa ctacccagac    2280
tacgaacaag ccaaggaatt tgctgaaggt gttaccgcca agttcccagg taaatggatg    2340
gcttacaact tgtctccatc tttcaactgg accaaggcca tgtctgttga cgaacaagaa    2400
actttcatcc aaagattagg tgacttgggt tacatctggc aattcatcac tttggctggt    2460
ttgcacacct ctggtttggc cattgaacaa ttctccaaga actttgccaa attgggtatg    2520
aaggcttacg ctcaagatat ccaaaagaag gaattggaca acggtattga catggttaag    2580
caccaaaaat ggtccggtgc tgaatacatc gatggtttgt tgagattggc tcaaggtggt    2640
ttggctgcta ccgctgccat gggtcaaggt gtcactgaag atcaattcaa gtaatgcccg    2700
ggcataaagc aatcttgatg aggataatga tttttttttg aatatacata aatactaccg    2760
tttttctgct agattttgtg aagacgtaaa taagtacata ttacttttta agccaagaca    2820
agattaagca ttaactttac ccttttctct tctaagtttc aatactagtt atcactgttt    2880
aaaagttatg gcgagaacgt cggcggttaa aatatattac cctgaacgtg gtgaattgaa    2940
gttctaggat ggtttaaaga ttttccttt ttgggaaata agtaaacaat atattgctgc    3000
ctttgcaaaa cgcacatacc cacaatatgt gactattggc aaagaacgca ttatcctttg    3060
aagaggtgga tactgatact aagagagtct ctattccggc tccactttta gtccagagat    3120
tacttgtctt cttacgtatc agaacaagaa agcatttcca agtaattgc atttgccctt    3180
gagcagtata tatatactaa gaaggcgcgc cctatttttcg aggaccttgt cacccttgagc    3240
ccaagagagc caagatttaa attttcctat gacttgatgc aaattcccaa agctaataac    3300
atgcaagaca cgtacggtca agaagacata tttgacctct aacaggttc agacgcgact    3360
gcctcatcag taagacccgt tgaaaagaac ttacctgaaa aaacgaata tatactagcg    3420
ttgaatgtta gcgtcaacaa caagaagttt aatgacgcgg aggccaaggc aaaaagattc    3480
cttgattacg taaggagtt agaatcattt tgaataaaaa acacgctttt tcagttcgag    3540
tttatcatta tcaatactgc catttcaaag aatacgtaaa taattaatag tagtgatttt    3600
cctaacttta tttagtcaaa aaattagcct tttaattctg ctgtaacccg tacatgccca    3660
```

```
aaataggggg cgggttacac agaatatata acatcgtagg tgtctgggtg aacagtttat    3720
tcctggcatc cactaaatat aatggagccc gcttttaag ctggcatcca gaaaaaaaaa     3780
gaatcccagc accaaaatat tgttttcttc accaaccatc agttcatagg tccattctct    3840
tagcgcaact acagagaaca ggggcacaaa caggcaaaaa acgggcacaa cctcaatgga    3900
gtgatgcaac ctgcctggag taaatgatga cacaaggcaa ttgacccacg catgtatcta    3960
tctcattttc ttcacccttc tattccttc tgctctctct gatttggaaa aagctgaaaa     4020
aaaaggttga aaccagttcc ctgaaattat tcccctactt gactaataag tatataaaga    4080
cggtaggtat tgattgtaat tctgtaaatc tatttcttaa acttcttaaa ttctactttt    4140
atagttagtc ttttttttag ttttaaaaca ccaagaactt agtttcgaat aaacacacat    4200
aaacaaacaa aatggtcaag gtttctttgg acaatgtcaa attgttagtc gatgttgaca    4260
aggaaccttt cttcaagcct tcttccacca ccgttggtga catcttgacc aaggatgctt    4320
tggaattcat tgtcttgttg cacagaactt caacaacaa gagaaagcaa ttgttggaaa     4380
acagacaagt tgttcaaaag aaattggact ctggttctta ccatttggac ttcttgccag    4440
aaactgctaa catcagaaac gacccaacct ggcaaggtcc aatttggct ccaggtttga      4500 tcaacagatc cactgaaatc actggtcctc cattgagaaa catgttgatc aatgctttga    4560
atgctccagt taacacctac atgactgact tcgaagattc tgcctctcca acctggaaca    4620
acatggttta cggtcaagtc aacttatacg atgctatcag aaaccaaatt gacttcgaca    4680
ctccaagaaa atcttacaaa ttgaacggta acgttgccaa cttgccaacc attattgtca    4740
gaccaagagg ttggcacatg gttgaaaagc atttatacgt tgacgacgaa ccaatttctg    4800
cctccatttt cgatttcggt ctatatttct accataacgc taaggaattg atcaagttgg    4860
gtaagggtcc atacttctac ttgccaaaga tggaacacca cttggaagct aagttgtgga    4920
acgatgtttt ctgtgttgct caagactaca ttggtattcc aagaggtacc atcagagcta    4980
ctgttttgat tgaaaactta ccagctgctt tccaaatgga agaaatcatc taccaattga    5040
gacaacactc ctctggtttg aactgtggta gatgggacta catcttttcc accatcaaga    5100
gattgagaaa cgacccaaac cacatttttgc caaacagaaa ccaagtcacc atgacttctc    5160
cattcatgga cgcttacgtc aagagattga tcaacacctg tcaccgtcgt ggtgtccacg    5220
ctatgggtgg tatggctgct caaattccaa tcaaggatga cccagctgcc aacgaaaagg    5280
ccatgaccaa ggtcagaaac gacaagatca gagaattaac caacggtcac gatggttcct    5340
gggttgctca cccagctttg gctccaatct gtaacgaagt ctttatcaac atgggtactc    5400
caaaccaaat ctacttcatt ccagaaaacg ttgtcactgc tgctaacttg ttggaaacca    5460
agattccaaa cggtgaaatc accactgaag gtattgtcca aaacttggat atcggtttgc    5520
aatacatgga agcttggtta cgtggttctg gttgtgttcc aatcaacaac ttgatggaag    5580
atgccgctac tgctgaagtt tcccgttgtc aattgtacca atgggttaag cacggtgtca    5640
ctttgaaaga caccggtgaa aaggtcactc cagaattgac tgaaaagatc ttaaaggaac    5700
aagttgaaag attatccaaa gcctctccat taggtgacaa gaacaagttc gctctagccg    5760
ccaaatactt cttgccagaa atcagaggtg aaaagttctc tgaattttg accactttgt      5820 tgtacgatga aattgtctcc accaaggcta ctccaaccga tttgtaatgc ccgggcgtga    5880
atttacttta aatcttgcat ttaaataaat tttcttttta tagctttatg acttagtttc    5940
aatttatata ctatttttaat gacattttcg attcattgat tgaaagcttt gtgttttttc    6000
```

```
ttgatgcgct attgcattgt tcttgtcttt ttcgccacat gtaatatctg tagtagatac    6060
ctgatacatt gtggatgctg agtgaaattt tagttaataa tggaggcgct cttaataatt    6120
ttggggatat tggcttttttt ttttaaagtt tacaaatgaa ttttttccgc caggataacg    6180
attctgaagt tactcttagc gttcctatcg gtacagccat caaatcatgc ctataaatca    6240
tgcctatatt tgcgtgcagt cagtatcatc tacatgaaaa aaactcccgc aatttcttat    6300
agaatacgtt gaaaattaaa tgtacgcgcc aagataagat aacatatatc tagatgcagt    6360
aatatacaca gattccggcc ggccgcggcc cagcgctact agttggccgg ccgtttaaac    6420
ggccaaggag gccgcggccg ccgtatatgt catgctcgtg acaaagagcg taagatggcg    6480
aacataactt cgtatagcat acattatacg aagttatccg gtaatttgaa acaaacccg    6540 gtctcgaagc ggagatccgg cgataattac cgcagaaata aacccataca cgagacgtag    6600
aaccagccgc acatggccgg agaaactcct gcgagaattt cgtaaactcg cgcgcattgc    6660
atctgtattt cctaatgcgg cacttccagg cctcgagacc tctgacatgc ttttgacagg    6720
aatagacatt ttcagaatgt tatccatatg cctttcgggt tttttttcctt cctttctccat    6780 catgaaaaat ctctcgagac cgtttatcca ttgctttttt gttgtctttt tccctcgttc    6840
acagaaagtc tgaagaagct atagtagaac tatgagcttt ttttgtttct gttttccttt    6900
tttttttttt tacctctgtg gaaattgtta ctctcacact ctttagttcg tttgtttgtt    6960
ttgtttattc caattatgac cggtgacgaa acgtggtcga tggtgggtac cgcttatgct    7020
cccctccatt agtttcgatt atataaaaag gccaaatatt gtattatttt caaatgtcct    7080
atcattatcg tctaacatct aatttctctt aaattttttc tctttcttttc ctataacacc    7140 aatagtgaaa atcttttttt cttctatatc tacaaaaact ttttttttct atcaacctcg    7200
ttgataaatt ttttctttaa caatcgttaa taattaatta attggaaaat aaccattttt    7260
tctctctttt atacacacat tcaaagaaaa gaaaaaaaat atccccagc tagttaaaga    7320 aaatcattga aaagaataag aagataagaa agatttaatt atcaaacaat atcaatatgc    7380
ctcaatcctg ggaagaactg gccgctgata agcgcgcccg cctcgcaaaa accatccctg    7440
atgaatggaa agtccagacg ctgcctgcgg aagacagcgt tattgatttc ccaaagaaat    7500
cggggatcct ttcagaggcc gaactgaaga tcacagaggc ctccgctgca gatcttgtgt    7560
ccaagctggc ggccggagag ttgacctcgg tggaagttac gctagcattc tgtaaacggg    7620
cagcaatcgc ccagcagtta acaaactgcg cccacgagtt cttccctgac gccgctctcg    7680
cgcaggcaag ggaactcgat gaatactacg caaagcacaa gagacccgtt ggtccactcc    7740
atggcctccc catctctctc aaagaccagc ttcgagtcaa gggctacgaa acatcaatgg    7800
gctacatctc atggctaaac aagtacgacg aaggggactc ggttctgaca accatgctcc    7860
gcaaagccgg tgccgtcttc tacgtcaaga cctctgtccc gcagaccctg atggtctgcg    7920
agacagtcaa caacatcatc gggcgcaccg tcaacccacg caacaagaac tggtcgtgcg    7980
gcggcagttc tggtggtgag ggtgcgatcg ttgggattcg tggtggcgtc atcggtgtag    8040
gaacggatat cggtggctcg attcgagtgc cggccgcgtt caacttcctg tacggtctaa    8100
ggccgagtca tgggcggctg ccgtatgcaa agatggcgaa cagcatggag ggtcaggaga    8160
cggtgcacag cgttgtcggg ccgattacgc actctgttga ggacctccgc ctcttcacca    8220
aatccgtcct cggtcaggag ccatggaaat acgactccaa ggtcatcccc atgccctggc    8280
gccagtccga gtcggacatt attgccttcca agatcaagaa cggcgggctc aatatccggct    8340 actacaactt cgacggcaat gtccttccac accctcctat cctgcgcggc gtggaaacca    8400
```

```
ccgtcgccgc actcgccaaa gccggtcaca ccgtgacccc gtggacgcca tacaagcacg   8460
atttcggcca cgatctcatc tcccatatct acgcggctga cggcagcgcc gacgtaatgc   8520
gcgatatcag tgcatccggc gagccggcga tcgcatttat caagcttatc gataccgtcg   8580
acctcgagtc atgtaattag ttatgtcacg cttacattca cgccctcccc ccacatccgc   8640
tctaaccgaa aaggaaggag ttagacaacc tgaagtctag gtccctattt attttttat    8700 agttatgtta gtattaagaa cgttatttat atttcaaatt tttctttttt ttctgtacag   8760
acgcgtgtac gcatgtaaca ttatactgaa aaccttgctt gagaaggttt tgggacgctc   8820
gaaggcttta atttgcggcc ggtacccaat tcgccctata gtgagtcgta ttacgcgcgc   8880
tcactggccg tcgttttaca acgtcgtgac tgggaaaacc ctggcgttac ccaacttaat   8940
cgccttgcag cacatccccc tttcgccagc tggcgtaata gcgaagaggc ccgcaccgat   9000
cgcccttccc aacagttgcg cagcctgaat ggcgaatggc gcgacgcgcc ctgtagcggc   9060
gcattaagcg cggcgggtgt ggtggttacg cgcagcgtga ccgctacact tgccagcgcc   9120
ctagcgcccg ctcctttcgc tttcttccct tcctttctcg ccacgttcgc cggctttccc   9180
cgtcaagctc taaatcgggg gctcccttta gggttccgat ttagtgcttt acggcacctc   9240
gaccccaaaa aacttgatta gggtgatggt tcacgtagtg ggccatcgcc ctgatagacg   9300
gtttttcgcc ctttgacgtt ggagtccacg ttctttaata gtggactctt gttccaaact   9360
ggaacaacac tcaaccctat ctcggtctat tcttttgatt tataagggat tttgccgatt   9420
tcggcctatt ggttaaaaaa tgagctgatt taacaaaaat ttaacgcgaa ttttaacaaa   9480
atattaacgt ttacaatttc ctgatgcggt attttctcct tacgcatctg tgcggtattt   9540
cacaccgcct ggatggcggc gttagtatcg aatcgacagc agtatagcga ccagcattca   9600
catacgattg acgcatgata ttactttctg cgcacttaac ttcgcatctg gcagatgat    9660 gtcgaggcga aaaaaatat  aaatcacgct aacatttgat taaaatagaa caactacaat   9720
ataaaaaaac tatacaaatg acaagttctt gaaaacaaga atctttttat tgtcagtact   9780
gattagaaaa actcatcgag catcaaatga aactgcaatt tattcatatc aggattatca   9840
ataccatatt tttgaaaaag ccgtttctgt aatgaaggag aaaactcacc gaggcagttc   9900
cataggatgg caagatcctg gtatcggtct gcgattccga ctcgtccaac atcaatacaa   9960
cctattaatt tccctcgtc  aaaaataagg ttatcaagtg agaaatcacc atgagtgacg  10020
actgaatccg gtgagaatgg caaaagctta tgcatttctt ccagacttg  ttcaacaggc  10080 cagccattac gctcgtcatc aaaatcactc gcatcaacca aaccgttatt cattcgtgat  10140
tgcgcctgag cgagacgaaa tacgcgatcg ctgttaaaag gacaattaca acaggaatc   10200 gaatgcaacc ggcgcaggaa cactgccagc gcatcaacaa tattttcacc tgaatcagga  10260
tattcttcta atacctggaa tgctgttttg ccggggatcg cagtggtgag taaccatgca  10320
tcatcaggag tacggataaa atgcttgatg gtcggaagag gcataaattc cgtcagccag  10380
tttagtctga ccatctcatc tgtaacatca ttggcaacgc tacctttgcc atgtttcaga  10440
aacaactctg gcgcatcggg cttcccatac aatcgataga ttgtcgcacc tgattgcccg  10500
acattatcgc gagcccattt ataccatat  aaatcagcat ccatgttgga atttaatcgc  10560
ggcctcgaaa cgtgagtctt ttccttaccc atggttgttt atgttcggat gtgatgtgag  10620
aactgtatcc tagcaagatt ttaaaggaa  gtatatgaaa gaagaacctc agtggcaaat  10680 cctaacctt  tatatttctc tacaggggcg cggcgtgggg acaattcaac gcgtctgtga  10740
```

```
ggggagcgtt tccctgctcg caggtctgca gcgaggagcc gtaattttg cttcgcgccg    10800
tgcggccatc aaaatgtatg gatgcaaatg attatacatg gggatgtatg ggctaaatgt    10860
acgggcgaca gtcacatcat gccctgagc tgcgcacgtc aagactgtca aggagggtat    10920
tctgggcctt ggtatggtgc actctcagta caatctgctc tgatgccgca tagtaagcca    10980
gccccgacac ccgccaacac ccgctgacgc gccctgacgg gcttgtctgc tcccggcatc    11040
cgcttacaga caagctgtga ccgtctccgg gagctgcatg tgtcagaggt tttcaccgtc    11100
atcaccgaaa cgcgcgagac gaaagggcct cgtgatacgc ctattttat aggttaatgt    11160
catgataata atggtttctt aggacggatc gcttgcctgt aacttacacg cgcctcgtat    11220
cttttaatga tggaataatt tgggaattta ctctgtgttt atttattttt atgttttgta    11280
tttggatttt agaaagtaaa taagaaggt agaagagtta cggaatgaag aaaaaaaat    11340
aaacaaaggt ttaaaaaatt tcaacaaaaa gcgtacttta catatatatt tattagacaa    11400
gaaaagcaga ttaatagat atacattcga ttaacgataa gtaaatgta aaatcacagg    11460
attttcgtgt gtggtcttct acacagacaa gatgaaacaa ttcggcatta atacctgaga    11520
gcaggaagag caagataaaa ggtagtattt gttggcgatc cccctagagt cttttacatc    11580
ttcgaaaaac aaaaactatt ttttctttaa tttcttttt tactttctat ttttaattta    11640
tatatttata ttaaaaaatt taaattataa ttatttttat agcacgtgat gaaaaggacc    11700
caggtggcac ttttcgggga aatgtgcgcg gaaccctat ttgtttattt ttctaaatac    11760
attcaaatat gtatccgctc atgagacaat aaccctgata aatgcttcaa taatattgaa    11820
aaaggaagag tatgagtatt caacatttcc gtgtcgccct tattccctt tttgcggcat    11880
tttgccttcc tgtttttgct cacccagaaa cgctggtgaa agtaaaagat gctgaagatc    11940
agttgggtgc acgagtgggt tacatcgaac tggatctcaa cagcggtaag atccttgaga    12000
gttttcgccc cgaagaacgt tttccaatga tgagcacttt taaagttctg ctatgtggcg    12060
cggtattatc ccgtattgac gccgggcaag agcaactcgg tcgccgcata cactattctc    12120
agaatgactt ggttgagtac tcaccagtca cagaaaagca tcttacggat ggcatgacag    12180
taagagaatt atgcagtgct gccataacca tgagtgataa cactgcggcc aacttacttc    12240
tgacaacgat cggaggaccg aaggagctaa ccgcttttt gcacaacatg ggggatcatg    12300
taactcgcct tgatcgttgg gaaccggagc tgaatgaagc cataccaaac gacgagcgtg    12360
acaccacgat gcctgtagca atggcaacaa cgttgcgcaa actattaact ggcgaactac    12420
ttactctagc ttcccggcaa caattaatag actggatgga ggcggataaa gttgcaggac    12480
cacttctgcg ctcggccctt ccggctggct ggtttattgc tgataaatct ggagccggtg    12540
agcgtgggtc tcgcggtatc attgcagcac tggggccaga tggtaagccc tcccgtatcg    12600
tagttatcta cacgacgggg agtcaggcaa ctatggatga acgaaataga cagatcgctg    12660
agataggtgc ctcactgatt aagcattggt aactgtcaga ccaagtttac tcatatatac    12720
tttagattga tttaaaactt catttttaat ttaaaaggat ctaggtgaag atcctttttg    12780
ataatctcat gaccaaaatc ccttaacgtg agttttcgtt ccactgagcg tcagaccccg    12840
tagaaaagat caaaggatct tcttgagatc ctttttttct gcgcgtaatc tgctgcttgc    12900
aaacaaaaaa accaccgcta ccagcggtgg tttgtttgcc ggatcaagag ctaccaactc    12960
tttttccgaa ggtaactggc ttcagcagag cgcagatacc aaatactgtc cttctagtgt    13020
agccgtagtt aggccaccac ttcaagaact ctgtagcacc gcctacatac ctcgctctgc    13080
taatcctgtt accagtggct gctgccagtg gcgataagtc gtgtcttacc gggttggact    13140
```

```
caagacgata gttaccggat aaggcgcagc ggtcgggctg aacgggggt tcgtgcacac   13200 agcccagctt ggagcgaacg acctacaccg aactgagata cctacagcgt gagctatgag   13260
aaagcgccac gcttcccgaa gggagaaagg cggacaggta tccggtaagc ggcagggtcg   13320
gaacaggaga gcgcacgagg gagcttccag ggggaaacgc ctggtatctt tatagtcctg   13380
tcgggtttcg ccacctctga cttgagcgtc gattttgtg atgctcgtca ggggggcgga   13440
gcctatggaa aaacgccagc aacgcggcct ttttacggtt cctggccttt tgctggcctt   13500
ttgctcacat gttctttcct gcgttatccc ctgattctgt ggataaccgt attaccgcct   13560
ttgagtgagc tgataccgct cgccgcagcc gaacgaccga gcgcagcgag tcagtgagcg   13620
aggaagcgga agagcgccca atacgcaaac cgcctctccc cgcgcgttgg ccgattcatt   13680
aatgcagctg gcacgacagg tttcccgact ggaaagcggg cagtgagcgc aacgcaatta   13740
atgtgagtta cctcactcat taggcacccc aggctttaca ctttatgctt ccggctccta   13800
tgttgtgtgg aattgtgagc ggataacaat ttcacacagg aaacagctat gaccatgatt   13860
acgccaagcg cgcaattaac cctcactaaa gggaacaaaa gctggagctc atttggcgag   13920
cgttggttgg tggatcaagc ccacgcgtag gcaatcctcg agcagatccg ccaggcgtgt   13980
atatatagcg tggatggcca ggcaacttta gtgctgacac atacaggcat atatatgt   14040 gtgcgacgac acatgatcat atggcatgca tgtgctctgt atgtatataa aactcttgtt   14100
ttcttctttt ctctaaatat tctttcctta tacattagga cctttgcagc ataaattact   14160
atacttctat agacacgcaa acacaaatac acactaat ctagacctgc aggcggcatt   14220
attgtgtatg gctcaataat tttataaaaa aaggaactat tggttcttag tattttcttg   14280
ctagaagaca tattcttacc aatcctttca taagctaatt atgccatcca tatagcaaga   14340
gaatccggtg ggggcgccat gcctatccgg cggcaacatt attactctgg tatacgggcg   14400
taactccata atatgccacc acttaccttt aacatgttca tggtaggtac cccacccagc   14460
cataaggaaa ttttcaaagg cgttggatca aaaaataggc ctttatttca tcgcgtgatt   14520
gaggagcata acatgtttag tgaaggtttc ttttggaaaa cttcagtcgc tcattattag   14580
aaccagggag gtccaggctt tgctggtggg agagaaagct tatgaagctg ggggttgcaga   14640 tttgtcgatt ggtcgccagt acacagtttt aaaaagtcag agaatgtaga gaagtatgga   14700
tctttgaaac cctggcgcgc cg                                            14722
```

<210> SEQ ID NO 5
<211> LENGTH: 8091
<212> TYPE: DNA
<213> ORGANISM: Artificial Sequence
<220> FEATURE:
<223> OTHER INFORMATION: Plasmid pBOL268

<400> SEQUENCE: 5

```
aaaagctgga gctcatttgg cgagcgttgg ttggtggatc aagcccacgc gtaggcaatc     60
ctcgagcaga tccgccaggc gtgtatatat agcgtggatg gccaggcaac tttagtgctg    120
acacatacag gcatatatat atgtgtgcga cgacacatga tcatatggca tgcatgtgct    180
ctgtatgtat ataaaactct tgttttcttc ttttctctaa atattctttc cttatacatt    240
aggacctttg cagcataaat tactatactt ctatagacac gcaaacacaa atacacacac    300
taatctagaa ctagtggatc ccccaaatcg ccggtgccgt cttctacgtc aagacctctg    360
tcccgcagac cctgatggtc tgcgagacag tcaacaacat catcgggcgc accgtcaacc    420
```

```
cacgcaacaa gaactggtcg tgcggcggca gttctggtgg tgagggtgcg atcgttggga      480
ttcgtggtgg cgtcatcggt gtaggaacgg atatcggtgg ctcgattcga gtgccggccg      540
cgttcaactt cctgtacggt ctaaggccga gtcatgggcg gctgccgtat gcaaagatgg      600
cgaacagcat ggagggtcag gagacggtgc acagcgttgt cgggccgatt acgcactctg      660
ttgaggacct ccgcctcttc accaaatccg tcctcggtca ggagccatgg aaatacgact      720
ccaaggtcat ccccatgccc tggcgccagt ccgagtcgga cattattgcc tccaagatca      780
agaacggcgg gctcaatatc ggctactaca acttcgacgg caatgtcctt ccacaccctc      840
ctatcctgcg cggcgtggaa accaccgtcg ccgcactcgc caaagccggt cacaccgtga      900
ccccgtggac gccatacaag cacgatttcg gccacgatct catctcccat atctacgcgg      960 ctgacgcag cgccgacgta atgcgcgata tcagtgcatc cggcgagccg gcgattccaa     1020
atatcaaaga cctactgaac ccgaacatca agctgttaa catgaacgag ctctgggaca     1080
cgcatctcca gaagtggaat taccagatgg agtaccttga aaatggcgg gaggctgaag     1140 aaaaggccgg gaaggaactg gacgccatca tcgcgccgat tacgcctacc gctgcggtac     1200
ggcatgacca gttccggtac tatgggtatg cctctgtgat caacctgctg gatttcacga     1260
gcgtggttgt tccggttacc tttgcggata gaacatcga taagaagaat gagagtttca     1320
aggcggttag tgagcttgat gccctcgtgc aggaagagta tgatccggag gcgtaccatg     1380
gggcaccggt tgcagtgcag gttatcggac ggagactcag tgaagagagg acgttggcga     1440
ttgcagagga agtggggaag ttgctgggaa atgtggtgac tccataggtc gagaatttat     1500
acttagataa gtatgtactt acaggtatat ttctatgaga tactgatgta tacatgcatg     1560
ataatattta aacggttatt agtgccgatt gtcttgtgcg ataatgacgt tcctatcaaa     1620
gcaatacact taccacctat tacatgggcc aagaaaatat tttcgaactt gtttagaata     1680
ttagcacaga gtatatgatg atatccgtta gattatgcat gattcattcc tacaactttt     1740
tcgtagcata aggattaatt acttggatgc caataaaaaa aaaaaacatc gagaaaattt     1800
cagcatgctc agaaacaatt gcagtgtatc aaagtaaaaa aagattttc gctacatgtt     1860 ccttttgaag aaagaaaatc atggaacatt agatttacaa aaatttaacc accgctgatt     1920
aacgattaga ccgttaagcg cacaacaggt tattagtaca gagaaagcat tctgtggtgt     1980
tgccccggac tttcttttgc gacataggta aatcgaatac catcatacta tcttttccaa     2040
tgactcccta agaaagact cttcttcgat gttgtatacg ttggagcata gggcaagaat     2100
tgtggcttga gatataactt cgtatagcat acattatacg aagttatcgt atatgtcatg     2160
ctcgtgacaa agagcgtaag atggcgaacg aattcggcgc gccgggccca gcgctactag     2220
ttggccggcc gtttaaacgg ccaaggaggc gcggccgca ttttatttta cttttttag      2280 aatgacctgt tcccgacact atgtaagatc tagcttttaa catattatgg aaacctgaaa     2340
tgtaaaatct gaattttgt atatgtgttt atatttgggt agttcttttg aggaaagcat     2400
gcatagactt gctgtacgaa ctttatgtga cttgtagtga cgctgtttca tgagacttta     2460 gcccttgaa catattatca tatctcagct tgaaatacta tagatttact tttgcagcca     2520
tttcttggtg ctccaaggtt gtgcgtatct attacttaat ttctgtcctt gccaagtttt     2580
gcagcagggc ggtcacaaga ctcctctgcc gtcattcctt agtccttcgg gaacacactt     2640
atttatgtat ttgtattcta caattctacg gtgcacaagg gttgggcact gttgagctca     2700
gcacgcaact attgctggca tgaagataag attgattttt ggaagaataa gcttgtggcc     2760
taggcccggg cgtcgaccte gagtcatgta attagttatg tcacgcttac attcacgccc     2820
```

```
tcccccccaca tccgctctaa ccgaaaagga aggagttaga caacctgaag tctaggtccc    2880
tatttatttt tttatagtta tgttagtatt aagaacgtta tttatatttc aaatttttct    2940 ttttttttctg tacagacgcg tgtacgcatg taacattata ctgaaaacct tgcttgagaa   3000
ggttttggga cgctcgaagg ctttaatttg cggccggtac ccaattcgcc ctatagtgag    3060
tcgtattacg cgcgctcact ggccgtcgtt ttacaacgtc gtgactggga aaaccctggc    3120
gttacccaac ttaatcgcct tgcagcacat ccccctttcg ccagctggcg taatagcgaa    3180
gaggcccgca ccgatcgccc ttcccaacag ttgcgcagcc tgaatggcga atggcgcgac    3240 gcgcccgta gcgcgcatt aagcgcggcg ggtgtggtgg ttacgcgcag cgtgaccgct      3300
acacttgcca gcgccctagc gcccgctcct ttcgctttct tcccttcctt tctcgccacg    3360
ttcgccggct ttccccgtca gctctaaat cggggctcc ctttaggtt ccgatttagt       3420 gctttacggc acctcgaccc caaaaaactt gattagggtg atggttcacg tagtgggcca    3480
tcgccctgat agacggtttt tcgccctttg acgttggagt ccacgttctt taatagtgga    3540
ctcttgttcc aaactggaac aacactcaac cctatctcgg tctattcttt tgatttataa    3600
gggattttgc cgatttcggc ctattggtta aaaaatgagc tgatttaaca aaaatttaac    3660
gcgaatttta acaaaatatt aacgtttaca atttcctgat gcggtatttt ctccttacgc    3720
atctgtgcgg tatttcacac cgcctggatg gcggcgttag tatcgaatcg acagcagtat    3780
agcgaccagc attcacatac gattgacgca tgatattact ttctgcgcac ttaacttcgc    3840
atctgggcag atgatgtcga ggcgaaaaaa aatataaatc acgctaacat ttgattaaaa    3900
tagaacaact acaatataaa aaaactatac aaatgacaag ttcttgaaaa caagaatctt    3960
tttattgtca gtactgatta gaaaaactca tcgagcatca aatgaaactg caatttattc    4020
atatcaggat tatcaatacc atattttttga aaaagccgtt tctgtaatga aggagaaaac    4080
tcaccgaggc agttccatag gatggcaaga tcctggtatc ggtctgcgat tccgactcgt    4140
ccaacatcaa tacaacctat taatttcccc tcgtcaaaaa taaggttatc aagtgagaaa    4200
tcaccatgag tgacgactga atccggtgag aatggcaaaa gcttatgcat ttctttccag    4260
acttgttcaa caggccagcc attacgctcg tcatcaaaat cactcgcatc aaccaaaccg    4320
ttattcattc gtgattgcgc ctgagcgaga cgaaatacgc gatcgctgtt aaaaggacaa    4380
ttacaaacag gaatcgaatg caaccggcgc aggaacactg ccagcgcatc aacaatattt    4440
tcacctgaat caggatattc ttctaatacc tggaatgctg ttttgccggg gatcgcagtg    4500
gtgagtaacc atgcatcatc aggagtacgg ataaaatgct tgatggtcgg aagaggcata    4560
aattccgtca gccagtttag tctgaccatc tcatctgtaa catcattggc aacgctacct    4620
ttgccatgtt tcagaaacaa ctctggcgca tcgggcttcc catacaatcg atagattgtc    4680
gcacctgatt gcccgacatt atcgcgagcc catttatacc catataaatc agcatccatg    4740
ttggaattta atcgcggcct cgaaacgtga gtcttttcct tacccatggt tgtttatgtt    4800
cggatgtgat gtgagaactg tatcctagca agatttttaaa aggaagtata tgaaagaaga    4860
acctcagtgg caaatcctaa ccttttatat ttctctacag gggcgcggcg tggggacaat    4920
tcaacgcgtc tgtgagggga gcgtttccct gctcgcaggt ctgcagcgag gagccgtaat    4980
ttttgcttcg cgccgtgcgg ccatcaaaat gtatggatgc aaatgattat acatggggat    5040
gtatgggcta aatgtacggg cgacagtcac atcatgcccc tgagctgcgc acgtcaagac    5100
tgtcaaggag ggtattctgg gccttggtat ggtgcactct cagtacaatc tgctctgatg    5160
```

```
ccgcatagta agccagcccc gacacccgcc aacacccgct gacgcgccct gacgggcttg    5220
tctgctcccg gcatccgctt acagacaagc tgtgaccgtc tccgggagct gcatgtgtca    5280
gaggttttca ccgtcatcac cgaaacgcgc gagacgaaag ggcctcgtga tacgcctatt    5340
tttataggtt aatgtcatga taataatggt ttcttaggac ggatcgcttg cctgtaactt    5400
acacgcgcct cgtatctttt aatgatggaa taatttggga atttactctg tgtttattta    5460
tttttatgtt ttgtatttgg attttagaaa gtaaataaag aaggtagaag agttacggaa    5520
tgaagaaaaa aaaataaaca aaggtttaaa aaatttcaac aaaaagcgta ctttacatat    5580
atatttatta gacaagaaaa gcagattaaa tagatataca ttcgattaac gataagtaaa    5640
atgtaaaatc acaggatttt cgtgtgtggt cttctacaca gacaagatga aacaattcgg    5700
cattaatacc tgagagcagg aagagcaaga taaaaggtag tatttgttgg cgatcccccct   5760 agagtctttt acatcttcgg aaaacaaaaa ctattttttc tttaatttct ttttttactt    5820 tctatttta atttatatat ttatattaaa aaatttaaat tataattatt tttatagcac     5880
gtgatgaaaa ggacccaggt ggcactttc ggggaaatgt gcgcggaacc cctatttgtt     5940 tattttcta aatacattca aatatgtatc cgctcatgag acaataaccc tgataaatgc     6000
ttcaataata ttgaaaaagg aagagtatga gtattcaaca tttccgtgtc gcccttattc    6060
ccttttttgc ggcatttgc cttcctgttt ttgctcaccc agaaacgctg gtgaaagtaa      6120
aagatgctga agatcagttg ggtgcacgag tgggttacat cgaactggat ctcaacagcg    6180
gtaagatcct tgagagtttt cgccccgaag aacgttttcc aatgatgagc acttttaaag    6240
ttctgctatg tggcgcggta ttatcccgta ttgacgccgg gcaagagcaa ctcggtcgcc    6300
gcatacacta ttctcagaat gacttggttg agtactcacc agtcacagaa aagcatctta    6360
cggatggcat gacagtaaga gaattatgca gtgctgccat aaccatgagt gataacactg    6420
cggccaactt acttctgaca acgatcggag gaccgaagga gctaaccgct tttttgcaca    6480
acatggggga tcatgtaact cgccttgatc gttgggaacc ggagctgaat gaagccatac    6540
caaacgacga gcgtgacacc acgatgcctg tagcaatggc aacaacgttg cgcaaactat    6600
taactggcga actacttact ctagcttccc ggcaacaatt aatagactgg atggaggcgg    6660
ataaagttgc aggaccactt ctgcgctcgg cccttccggc tggctggttt attgctgata    6720
aatctggagc cggtgagcgt gggtctcgcg gtatcattgc agcactgggg ccagatggta    6780
agccctcccg tatcgtagtt atctacacga cggggagtca ggcaactatg gatgaacgaa    6840
atagacagat cgctgagata ggtgcctcac tgattaagca ttggtaactg tcagaccaag    6900
tttactcata tatactttag attgatttaa aacttcattt ttaatttaaa aggatctagg    6960
tgaagatcct ttttgataat ctcatgacca aaatccctta acgtgagttt cgttccact    7020 gagcgtcaga ccccgtagaa aagatcaaag gatcttcttg agatcctttt tttctgcgcg   7080
taatctgctg cttgcaaaca aaaaaaccac cgctaccagc ggtggtttgt ttgccggatc    7140
aagagctacc aactctttt ccgaaggtaa ctggcttcag cagagcgcag ataccaaata    7200
ctgtccttct agtgtagccg tagttaggcc accacttcaa gaactctgta gcaccgccta    7260
catacctcgc tctgctaatc ctgttaccag tggctgctgc cagtggcgat aagtcgtgtc    7320
ttaccgggtt ggactcaaga cgatagttac cggataaggc gcagcggtcg ggctgaacgg    7380
ggggttcgtg cacacagccc agcttggagc gaacgaccta caccgaactg agatacctac    7440
agcgtgagct atgagaaagc gccacgcttc ccgaagggag aaaggcggac aggtatccgg    7500
taagcggcag ggtcggaaca ggagagcgca cgagggagct tccaggggga aacgcctggt    7560
```

-continued

```
atctttatag tcctgtcggg tttcgccacc tctgacttga gcgtcgattt ttgtgatgct      7620
cgtcaggggg gcggagccta tggaaaaacg ccagcaacgc ggccttttta cggttcctgg      7680
ccttttgctg gccttttgct cacatgttct ttcctgcgtt atcccctgat tctgtggata      7740
accgtattac cgcctttgag tgagctgata ccgctcgccg cagccgaacg accgagcgca      7800
gcgagtcagt gagcgaggaa gcggaagagc gcccaatacg caaaccgcct ctccccgcgc      7860
gttggccgat tcattaatgc agctggcacg acaggtttcc cgactggaaa gcgggcagtg      7920
agcgcaacgc aattaatgtg agttaccctca ctcattaggc accccaggct ttacacttta      7980
tgcttccggc tcctatgttg tgtggaattg tgagcggata caatttcac acaggaaaca      8040 gctatgacca tgattacgcc aagcgcgcaa ttaaccctca ctaaagggaa c               8091
```

<210> SEQ ID NO 6
<211> LENGTH: 416
<212> TYPE: PRT
<213> ORGANISM: Aspergillus niger

<400> SEQUENCE: 6

```
Met Asn Val Glu Thr Ser Leu Pro Gly Ser Ser Gly Ser Asp Leu Glu
1               5                   10                  15

Thr Phe His His Glu Thr Lys Lys His Ala Asn His Asp Ser Gly Ile
            20                  25                  30

Ser Val Asn His Glu Ala Glu Ile Gly Val Asn His Thr Phe Glu Lys
        35                  40                  45

Pro Gly Pro Val Gly Ile Arg Glu Arg Leu Arg His Phe Thr Trp Ala
    50                  55                  60

Trp Tyr Thr Leu Thr Met Ser Cys Gly Gly Leu Ala Leu Leu Ile Val
65                  70                  75                  80

Asn Gln Pro His Asp Phe Lys Gly Leu Lys Asp Ile Ala Arg Val Val
                85                  90                  95

Tyr Cys Leu Asn Leu Ala Phe Phe Val Ile Val Thr Ser Leu Met Ala
            100                 105                 110

Ile Arg Phe Ile Leu His Lys Asn Met Trp Glu Ser Leu Gly His Asp
        115                 120                 125

Arg Glu Gly Leu Phe Phe Pro Thr Phe Trp Leu Ser Ile Ala Thr Met
    130                 135                 140

Ile Thr Gly Leu Tyr Lys Cys Phe Gly Asp Asp Ala Asn Glu Lys Phe
145                 150                 155                 160

Thr Lys Cys Leu Gln Val Leu Phe Trp Ile Tyr Cys Gly Cys Thr Met
                165                 170                 175

Ile Thr Ala Val Gly Gln Tyr Ser Phe Val Phe Ala Thr His Lys Tyr
            180                 185                 190

Glu Leu His Thr Met Met Pro Ser Trp Ile Leu Pro Ala Phe Pro Val
        195                 200                 205

Met Leu Ser Gly Thr Ile Ala Ser Val Ile Gly Ser Gly Gln Pro Ala
    210                 215                 220

Ser Asp Gly Ile Pro Ile Ile Ala Gly Ile Thr Phe Gln Gly Leu
225                 230                 235                 240

Gly Phe Ser Ile Ser Phe Met Met Tyr Ala His Tyr Ile Gly Arg Leu
                245                 250                 255

Met Glu Val Gly Leu Pro Ser Pro Glu His Arg Pro Gly Met Phe Ile
            260                 265                 270

Cys Val Gly Pro Pro Ala Phe Thr Ala Leu Ala Leu Val Gly Met Ala
```

```
            275                 280                 285
Lys Ala Leu Pro Asp Asp Phe Gln Ile Val Gly Asp Pro His Ala Val
    290                 295                 300

Ile Asp Gly Arg Val Met Leu Phe Leu Ala Val Ser Ala Ala Ile Phe
305                 310                 315                 320

Leu Trp Ala Leu Ser Phe Trp Phe Phe Cys Ile Ala Val Val Ala Val
                325                 330                 335

Val Arg Ser Pro Pro Lys Gly Phe His Leu Asn Trp Phe Ala Met Val
            340                 345                 350

Phe Pro Asn Thr Gly Phe Thr Leu Ala Thr Ile Thr Leu Ala Asn Met
        355                 360                 365

Phe Glu Ser Pro Gly Val Lys Gly Val Ala Thr Ala Met Ser Leu Cys
    370                 375                 380

Val Ile Ile Met Phe Ile Phe Val Leu Val Ser Ala Ile Arg Ala Val
385                 390                 395                 400

Ile Arg Lys Asp Ile Met Trp Pro Gly Gln Asp Glu Asp Val Ser Glu
                405                 410                 415
```

<210> SEQ ID NO 7
<211> LENGTH: 2188
<212> TYPE: DNA
<213> ORGANISM: Artificial Sequence
<220> FEATURE:
<223> OTHER INFORMATION: DCT_02 synthetic construct

<400> SEQUENCE: 7

```
gggcccggat ccggcgcgcc ccgcggaacc gccagatatt cattacttga cgcaaaagcg      60
tttgaaataa tgacgaaaaa gaaggaagaa aaaaaagaa aaataccgct tctaggcggg      120
ttatctactg atccgagctt ccactaggat agcacccaaa cacctgcata tttggacgac      180
ctttacttac accaccaaaa accactttcg cctctcccgc ccctgataac gtccactaat      240
tgagcgatta cctgagcggt cctcttttgt ttgcagcatg agacttgcat actgcaaatc      300
gtaagtagca acgtctcaag gtcaaaactg tatggaaacc ttgtcacctc acttaattct      360
agctagccta ccctgcaagt caagaggtct ccgtgattcc tagccacctc aaggtatgcc      420
tctccccgga aactgtggcc ttttctggca cacatgatct ccacgatttc aacatataaa      480
tagcttttga taatgcaat attaatcaaa tttattttac ttctttcttg taacatctct      540
cttgtaatcc cttattcctt ctagctattt ttcataaaaa accaagcaac tgcttatcaa      600
cacacaaaca ctaaaacaaa atgaacgttg aaacttcttt gccaggttct tctggttctg      660
acttggaaac tttccaccac gaaaccaaga agcatgccaa ccacgactct ggtatttccg      720
tcaaccatga agctgaaatt ggtgttaacc acactttcga aaagccaggt ccagttggta      780
tcagagaaag attacgtcac ttcacctggg cttggtacac tttgaccatg tcctgtggtg      840
gtttggcttt gttgattgtc aaccaaccac acgacttcaa gggtttgaaa gatattgcca      900
gagttgtcta ctgtttgaac ttggctttct ttgttatcgt tacctctttg atggccatca      960
gattcatctt gcaagagaac atgtgggaat ccttgggtca cgacagagaa ggtttgtttt     1020
tcccaacttt ctggttatcc attgctacca tgatcactgg tttgtacaag tgtttcggtg     1080
atgatgctaa cgaaaagttc accaagtgtt tgcaagtttt gttctggatc tactgtggtt     1140
gtaccatgat cactgctgtc ggtcaatact ctttcgtctt tgctacccac aaatacgaat     1200
tgcacaccat gatgccatcc tggatcttgc cagctttccc agttatgttg tctggtacta     1260
tcgcctccgt catcggttct ggtcaaccag cttccgatgg tattccaatt attattgctg     1320
```

```
gtatcactttt ccaaggttta ggttctcca tctccttcat gatgtacgct cactacattg    1380
gtagattgat ggaagttggt ttaccatctc cagaacacag accaggtatg ttcatctgtg    1440
ttggtcctcc agctttcacc gctttggctt tggtcggtat ggccaaggct ttaccagacg    1500
acttccaaat tgtcggtgac cctcacgctg tcattgacgg tcgtgttatg ttgttcttgg    1560
ctgtctctgc tgccatcttc ttatgggctt tgtctttctg gttcttctgt atcgctgttg    1620
ttgctgttgt cagatctcca ccaaagggtt tccatttgaa ctggtttgcc atggttttcc    1680
caaacactgg tttcaccttg gctaccatca ctttggctaa catgttcgaa tctccaggtg    1740
tcaagggtgt tgccactgct atgtccctat gtgtcatcat catgtttatt ttcgtcttgg    1800
tttctgccat cagagctgtc atcagaaagg acatcatgtg gccaggtcaa gatgaagatg    1860
tttctgaata agagcttttg attaagcctt ctagtccaaa aaacacgttt ttttgtcatt    1920
tatttcattt tcttagaata gtttagtta ttcatttat agtcacgaat gttttatgat    1980
tctatatagg gttgcaaaca agcattttc attttatgtt aaaacaattt caggtttacc    2040
ttttattctg cttgtggtga cgcgggtatc cgcccgctct tttggtcacc catgtattta    2100
attgcataaa taattcttaa aagtggagct agtctatttc tatttacata cctctcattt    2160
ctcatttcct ccatttaaat gcggccgc                                      2188
```

<210> SEQ ID NO 8
<211> LENGTH: 19666
<212> TYPE: DNA
<213> ORGANISM: Artificial Sequence
<220> FEATURE:
<223> OTHER INFORMATION: Plasmid pSUC174

<400> SEQUENCE: 8

```
catcctggcg gaaaaaattc atttgtaaac tttaaaaaaa aaagccaata tccccaaaat     60
tattaagagc gcctccatta ttaactaaaa tttcactcag catccacaat gtatcaggta    120
tctactacag atattacatg tggcgaaaaa gacaagaaca atgcaatagc gcatcaagaa    180
aaaacacaaa gctttcaatc aatgaatcga aaatgtcatt aaaatagtat ataaattgaa    240
actaagtcat aaagctataa aaagaaaatt tatttaaatg caagatttaa agtaaattca    300
ccttaactgt ccaagatgaa agacttaccc ttttcaatgt tctttctcaa ttccttgaca    360
gcagtgttga ccaattgttc ttctcttgga gacaattttt ccaaaacaga agtgtcaatg    420
gaaacaacgg aaccgtttct caaaacaatt ggcaaagaga gtattcaat ggagttgtca    480 ccgactaatt gttgagcctt cttaccgttc tcaaacctg gcaagtagac gaaagcagac    540
aaagattcag tttctggctt ttcgttgtgg aaagaacgta agacttcttc agcaaatttg    600
gcaccagcga aagccatgga caaggtagca gaaccggcac cttgcttggc cttgacaatt    660
tcgtcaccac cgaattggac tctgtggatg aaatgttcgt attgcttgtc caattggaaa    720
accaaggatt tgtcagtgat gattggaatg atggtttcac cagagtgacc accgatgacg    780
gtgacctttc tgtgcatggt ggtcttgtct tgttcttgac cgatctttgg gttcttcaac    840
atcaagtagt caaccaagaa agtttcagct ctgaccaaat ccaagttggt gacacccata    900
acgttacctg gcttgaactt acccatcttc ttcaaagttt caacggcaat tggaaccaaa    960
gagttaacag ggttggagat gactaagata cgagcgtttg gggcaaattt accgacagca   1020
gtaaccaaag acttaacgat accagcgttc atcttgaaca aatcatctct ggtcaaacct   1080
ggctttcttg gaacaccagc tggaatcaag acaacttgag cattggacaa agtgttttcg   1140
```

```
atggaatcct tgtcgtaacc aacacaagag gagttggtgt tgatgtggga caaatcctta    1200
ccaatacctt cagcagctct gatatcgtac aaagccaatt cagaaacgta tggagacaat    1260
ttcaataata gagataatgg ttgaccgaca ccaccagaag cacctaagat ggcaacctta    1320
accattttgt ttgtttatgt gtgtttattc gaaactaagt tcttggtgtt ttaaaactaa    1380
aaaaaagact aactataaaa gtagaattta agaagtttaa gaaatagatt tacagaatta    1440
caatcaatac ctaccgtctt tatatactta ttagtcaagt aggggaataa tttcagggaa    1500
ctggtttcaa cctttttttt cagctttttc caaatcagag agagcagaag gtaatagaag    1560
gtgtaagaaa atgagataga tacatgcgtg ggtcaattgc cttgtgtcat catttactcc    1620
aggcaggttg catcactcca ttgaggttgt gcccgttttt tgcctgtttg tgcccctgtt    1680
ctctgtagtt gcgctaagag aatggaccta tgaactgatg gttggtgaag aaaacaatat    1740
tttggtgctg ggattctttt tttttctgga tgccagctta aaaagcgggc tccattatat    1800
ttagtggatg ccaggaataa actgttcacc cagacaccta cgatgttata tattctgtgt    1860
aacccgcccc ctattttggg catgtacggg ttacagcaga attaaaaggc taattttttg    1920
actaaggccg gccacgcgtg aagatctcgt tatgtacccg aatatgtcag tttacattgg    1980
tcagtctatt ggagaattaa gtttgatcgt aggtatagac cggacaatat gccggaatat    2040
gtaaggcaat tgttccaaga tttggaaggt attgatttaa aaagtaataa agtttcaaat    2100
aaatatgata agcaagataa tagcaacggg agtgaaatca atgggggctt ttttgataat    2160
gaggaagggc aggaactcca catgggtcaa aaagcaagtt attttgcaac gacatacaat    2220
tcaagattat ttgacagtaa atactcccaa ttaaaaaaga aattcatgga ctgggatagt    2280
aattcctgga cagatattcc agatgattta aaaatatacc tacagcaaga tgaatcgctt    2340
tagcattaaa aaaacccctt cggtacgtaa tataaaaaat tttataggta atatacatat    2400
ataaaaatac ttcaatcatt tttacaatct tgtatacttt atacaacatg tgaaatcttc    2460
tgcttctgga catcaatatt caaatacagg ccaatcttag gtaaaacatt tggagaaaag    2520
aaggataagg caggacgagg gaagataaat agtttcgtta attataaata catgcagata    2580
aataaaggaa tatcaaatat tatgaataga aaaagaagat ggtgagacaa aaaagtagta    2640
ataaataggt ccaaatcttc tttatttccc cttttctttc ttatccttt tgttttctcca    2700 tattgtataa gaatatattc ttaggaaaat caacagggaa tacagtatag tgattttcgt    2760 tccttttttga gcgtaatccc ttcgagactg tgatgttgat tattttttgtt gtgatttcaa    2820 aattcttagg ttagttgtat agttcccgtt cataacataa tggatagtaa atgaaaaatc    2880
aaaataaggg tgaaacaaat agacaataaa gatgtagttt tcgaggacga aaaacaaacc    2940
taaccaacaa tgaccttatc accatcgaat tcataagcag gaatttctaa gtttaagggg    3000
gcaggtccct ttctgattct accggaaata tcataatgtg aaccatggca aggacagaac    3060
caaccaccaa aatcaccggc ttcaccaatt ggaacacaac ctaagtgagt acaaataccc    3120
agcataatta accattgagg gtctttgact ctgtcagcat cggtctgtgg gtccttcaaa    3180
gcggacatat ccacactgtt ggcttcctga atttcatgag gagttctgtg tctaatgaac    3240
acaggcttac cttgccattt gacaaccacg ttttacccca atgggatagc cgctaaatta    3300
acttcaactt tagccatagc caaaacatcg gcagtagcgg tcatagatga aataaaggtt    3360
tctacggttg atttggcacc tgcagatgac aaaagaccca tagcaccgac cataaagtaa    3420
gcataagaac ggcctttatc agcatcgtta ttttcctta aaacgtcatc aaaatttggg    3480
gtcctgtacg tggatttgct agccagcaaa gattgagaaa tcaggtacca cggctcctcg    3540
```

```
ctgcagacct gcgagcaggg aaacgctccc ctcacagtcg cgttgaattg tccccacgcc    3600
gcgcccctgt agagaaatat aaaaggttag gatttgccac tgaggttctt ctttcatata    3660 cttccttta  aaatcttgct aggatacagt tctcacatca catccgaaca taaacaacca    3720
tgggtaagga aaagactcac gtttcgaggc cgcgattaaa ttccaacatg gatgctgatt    3780
tatatgggta taaatgggct cgcgataatg tcgggcaatc aggtgcgaca atctatcgat    3840
tgtatgggaa gcccgatgcg ccagagttgt ttctgaaaca tggcaaaggt agcgttgcca    3900
atgatgttac agatgagatg gtcagactaa actggctgac ggaatttatg cctcttccga    3960
ccatcaagca ttttatccgt actcctgatg atgcatggtt actcaccact gcgatccccg    4020
gcaaaacagc attccaggta ttagaagaat atcctgattc aggtgaaaat attgttgatg    4080
cgctggcagt gttcctgcgc cggttgcatt cgattcctgt ttgtaattgt ccttttaaca    4140
gcgatcgcgt atttcgtctc gctcaggcgc aatcacgaat gaataacggt ttggttgatg    4200
cgagtgattt tgatgacgag cgtaatggct ggcctgttga acaagtctgg aaagaaatgc    4260
ataagctttt gccattctca ccggattcag tcgtcactca tggtgatttc tcacttgata    4320
accttatttt tgacgagggg aaattaatag gttgtattga tgttggacga gtcggaatcg    4380
cagaccgata ccaggatctt gccatcctat ggaactgcct cggtgagttt ctccttcat    4440 tacagaaacg cttttttcaa aaatatggta ttgataatcc tgatatgaat aaattgcagt    4500
ttcatttgat gctcgatgag ttttctaat cagtactgac aataaaaaga ttcttgtttt    4560
caagaacttg tcatttgtat agttttttta tattgtagtt gttctatttt aatcaaatgt    4620
tagcgtgatt tatatttttt ttcgcctcga catcatctgc ccagatgcga agttaagtgc    4680
gcagaaagta atatcatgcg tcaatcgtat gtgaatgctg gtcgctatac tgctgtcgat    4740
tcgatactaa cgccgccatc cagggtacca tccttttgtt gtttccgggt gtacaatatg    4800
gacttcctct tttctggcaa ccaaacccat acatcgggat tcctataata ccttcgttgg    4860
tctccctaac atgtaggtgg cggaggggag atatacaata gaacagatac cagacaagac    4920
ataatgggct aaacaagact acacaaatta cactgcctca ttgatggtgg tacataacga    4980
actaatactg tagccctaga cttgatagcc atcatcatat cgaagtttca ctacccttt    5040 tccatttgcc atctattgaa gtaataatag gcgcatgcaa cttcttttct ttttttttct    5100
tttctctctc ccccgttgtt gtctcaccat atccgcaatg acaaaaaaaa tgatggaaga    5160
cactaaagga aaaaattaac gacaaagaca gcaccaacag atgtcgttgt tccagagctg    5220
atgaggggta tcttcgaaca cacgaaactt tttccttcct tcattcacgc acactactct    5280
ctaatgagca acggtatacg gccttccttc cagttacttg aatttgaaat aaaaaaagtt    5340
tgccgctttg ctatcaagta taaatagacc tgcaattatt aatcttttgt ttcctcgtca    5400
ttgttctcgt tccctttctt ccttgtttct ttttctgcac aatatttcaa gctataccaa    5460
gcatacaatc aactatctca tatacaatgc ctcaatcctg ggaagaactg gccgctgata    5520
agcgcgcccg cctcgcaaaa accatccctg atgaatggaa agtccagacg ctgcctgcgg    5580
aagacagcgt tattgatttc ccaaagaaat cggggatcct ttcagaggcc gaactgaaga    5640
tcacagaggc ctccgctgca gatcttgtgt ccaagctggc ggccggagag ttgacctcgg    5700
tggaagttac gctagcattc tgtaaacggg cagcaatcgc ccagcagtta acaaactgcg    5760
cccacgagtt cttccctgac gccgctctcg cgcaggcaag ggaactcgat gaatactacg    5820
caaagcacaa gagacccgtt ggtccactcc atggcctccc catctctctc aaagaccagc    5880
```

```
ttcgagtcaa gggctacgaa acatcaatgg gctacatctc atggctaaac aagtacgacg    5940
aaggggactc ggttctgaca accatgctcc gcaaagccgg tgccgtcttc tacgtcaaga    6000
cctctgtccc gcagaccctg atggtctgcg agacagtcaa caacatcatc gggcgcaccg    6060
tcaacccacg caacaagaac tggtcgtgcg gcggcagttc tggtggtgag ggtgcgatcg    6120
ttgggattcg tggtggcgtc atcggtgtag gaacggatat cggtggctcg attcgagtgc    6180
cggccgcgtt caacttcctg tacggtctaa ggccgagtca tgggcggctg ccgtatgcaa    6240
agatggcgaa cagcatggag ggtcaggaga cggtgcacag cgttgtcggg ccgattacgc    6300
actctgttga ggacctccgc ctcttcacca aatccgtcct cggtcaggag ccatggaaat    6360
acgactccaa ggtcatcccc atgccctggc gccagtccga gtcggacatt attgcctcca    6420
agatcaagaa cggcgggctc aatatcggct actacaactt cgacggcaat gtccttccac    6480
accctcctat cctgcgcggc gtggaaacca ccgtcgccgc actcgccaaa gccggtcaca    6540
ccgtgacccc gtggacgcca tacaagcacg atttcggcca cgatctcatc tcccatatct    6600
acgcggctga cggcagcgcc gacgtaatgc gcgatatcag tgcatccggc gagccggcga    6660
ttccaaatat caaagaccta ctgaacccga acatcaaagc tgttaacatg aacgagctct    6720
gggacacgca tctccagaag tggaattacc agatggagta ccttgagaaa tggcgggagg    6780
ctgaagaaaa ggccgggaag gaactggacg ccatcatcgc gccgattacg cctaccgctg    6840
cggtacggca tgaccagttc cggtactatg ggtatgcctc tgtgatcaac ctgctggatt    6900
tcacgagcgt ggttgttccg gttacctttg cggataagaa catcgataag aagaatgaga    6960
gtttcaaggc ggttagtgag cttgatgccc tcgtgcagga agagtatgat ccggaggcgt    7020
accatggggc accggttgca gtgcaggtta tcggacggag actcagtgaa gagaggacgt    7080
tggcgattgc agaggaagtg gggaagttgc tgggaaatgt ggtgactcca taggtcgaga    7140
atttatactt agataagtat gtacttacag gtatatttct atgagatact gatgtataca    7200
tgcatgataa tatttaaacg gttattagtg ccgattgtct tgtgcgataa tgacgttcct    7260
atcaaagcaa tacacttacc acctattaca tgggccaaga aaatattttc gaacttgttt    7320
agaatattag cacagagtat atgatgatat ccgttagatt atgcatgatt cattcctaca    7380
acttttttcgt agcataagga ttaattactt ggatgccaat aaaaaaaaaa aacatcgaga    7440
aaatttcagc atgctcagaa acaattgcag tgtatcaaag taaaaaaaag attttcgcta    7500
catgttcctt ttgaagaaag aaaatcatgg aacattagat ttacaaaaat ttaaccaccg    7560
ctgattaacg attagaccgt taagcgcaca acaggttatt agtacagaga aagcattctg    7620
tggtgttgcc ccggactttc ttttgcgaca taggtaaatc gaataccatc atactatctt    7680
ttccaatgac tccctaaaga aagactcttc ttcgatgttg tatacgttgg agcatagggc    7740
aagaattgtg gcttgagatc tagattacgt ggaagaaagg tagtaaaagt agtagtataa    7800
gtagtaaaaa gaggtaaaaa gagaaaaccg gctacatact agagaagcac gtacacaaaa    7860
actcataggc acttcatcat acgacagttt cttgatgcat tataatagtg tattagatat    7920
tttcagaaat atgcatagaa cctcttcttg cctttacttt ttatacatag aacattggca    7980
gatttactta cactactttg tttctacgcc atttctttttg ttttcaacac ttagacaagt    8040
tgttgagaac cggactacta aaaagcaatg ttcccactga aaatcatgta cctgcaggat    8100
aataaccccc taattctgca tcgatccagt atgttttttt ttctctactc attttttacct    8160
gaagatagag cttctaaaac aaaaaaaatc agcgattaca tgcatattgt gtgttctaga    8220
attgcggatc accagatcgc cattacaatg tatgcaggca aatatttctc agaatgaaaa    8280
```

```
atagagaaaa ggaaacgaaa attctgtaag atgccttcga agagatttct cgatatgcaa    8340
ggcgtgcatc agggtgatcc aaaggaactc gagagagagg gcgaaaggca atttaatgca    8400
ttgcttctcc attgacttct agttgagcgg ataagttcgg aaatgtaagt cacagctaat    8460
gacaaatcca ctttaggttt cgaggcacta tttaggcaaa aagacgagtg gggaaataac    8520
aaacgctcaa acatattagc atataccttc aaaaaatggg aatagtatat aaccttccgg    8580
ttcgttaata aatcaaatct ttcatctagt tctcttaaga tttcaatatt ttgctttctt    8640
gaagaaagaa tctactctcc tcccccattc gcactgcaaa gctagcttgg cactggccgt    8700
cgttttacaa cgtcgtgact gggaaaaccc tggccttacc caacttaatc gccttgcagc    8760
acatcccccT TTcgccagct ggcgtaatag cgaagaggcc cgcaccgatc gcccttccca    8820
acagttgcgc agcctgaatg gcgaatggga aattgtaaac gttaatattt tgttaaaatt    8880
cgcgttaaat ttttgttaaa tcagctcatt ttttaaccaa taggccgaaa tcggcaaaat    8940
cccttataaa tcaaaagaat agaccgagat agggttgagt gttgttccag tttggaacaa    9000
gagtccacta ttaaagaacg tggactccaa cgtcaaaggg cgaaaaaccg tctatcaggg    9060
cgatggccca ctacgtgaac catcaccctA atcaagtttt tggggtcga ggtgccgtaa     9120 agcactaaat cggaaccCTA aagggagccc ccgatttaga gcttgacggg gaaagccggc    9180
gaacgtggcg agaaaggaag ggaagaaagc gaaaggagcg ggcgctaggg cgctggcaag    9240
tgtagcggtc acgctgcgcg taaccaccac acccgccgcg cttaatgcgc cgctacaggg    9300
cgcgtcaggt ggcactttTC ggggaaatgt gcgcggaacc cctatttgtt tattttTCTa    9360
aatacattca aatatgtatc cgctcatgag acaataaccc tgataaatgc ttcaataata    9420
ttgaaaaagg aagagtatga gtattcaaca tttccgtgtc gcccttattc ccttttttgc    9480
ggcatttTgc cttcctgtTT ttgctcaccc agaaacgctg gtgaaagtaa aagatgctga    9540
agatcagttg ggtgcacgag tgggttacat cgaactggat ctcaacagcg gtaagatcct    9600
tgagagtttt cgccccgaag aacgttttcc aatgatgagc acttttaaag ttctgctatg    9660
tggcgcggta ttatcccgta ttgacgccgg gcaagaccaa ctcggtcgcc gcatacacta    9720
ttctcagaat gacttggttg agtactcacc agtcacagaa aagcatctta cggatggcat    9780
gacagtaaga gaattatgca gtgctgccat aaccatgagt gataacactg cggccaactt    9840
acttctgaca acgatcggag gaccgaagga gctaaccgct tttttgcaca acatggggga    9900
tcatgtaact cgccttgatc gttgggaacc ggagctgaat gaagccatac caaacgacga    9960
gcgtgacacc acgatgcctg tagcaatggc aacaacgttg cgcaaactat taactggcga   10020
actacttagt ctagcttccc ggcaacaatt aatagactgg atggaggcgg ataaagttgc   10080
aggaccactt ctgcgctcgg cccttccggc tggctggttt attgctgata aatctggagc   10140
cggtgagcgt gggtctcgcg gtatcattgc agcactgggg ccagatggta agccctcccg   10200
tatcgtagtt atctacacga cggggagtca ggcaactatg gatgaacgaa atagacagat   10260
cgctgagata ggtgcctcac tgattaagca ttggtaactg tcagaccaag tttactcata   10320
tatactttag attgatttaa aacttcattt ttaatttaaa aggatctagg tgaagatcct   10380
ttttgataat ctcatgacca aaatccctta acgtgagttt cgttccact gagcgtcaga    10440 ccccgtagaa aagatcaaag gatcttcttg agatcctttt tttctgcgcg taatctgctg   10500
cttgcaaaca aaaaaaccac cgctaccagc ggtggtttgt ttgccggatc aagagctacc   10560
acctcttttt ccgaaggtaa ctggcttcag cagagcgcag ataccaaata ctgtccttct   10620
```

```
agtgtagccg tagttaggcc accacttcaa gaactctgta gcaccgccta catacctcgc  10680
tctgctaatc ctgttaccag tggctgctgc cagtggcgat aagtcgtgtc ttaccgggtt  10740
ggactcaaga cgatagttac cggataaggc gcagcggtcg ggctgaacgg ggggttcgtg  10800
cacacagccc agcttggagc gaacgaccta caccgaactg agatacctac agcgtgagca  10860
ttgagaaagc gccacgcttc ccgaagggag aaaggcggac aggtatccgg taagcggcag  10920
ggtcggaaca ggagagcgca cgagggagct tccaggggga aacgcctggt atctttatag  10980
tcctgtcggg tttcgccacc tctgacttga gcgtcgattt ttgtgatgct cgtcaggggg  11040
gcggagccta tggaaaaacg ccagcaacgc ggccttttta cggttcctgg cctttttgctg  11100
gcctttttgct cacatgttct ttcctgcgtt atcccctgat tctgtggata accgtattac  11160
cgcctttgag tgagctgata ccgctcgccg cagccgaacg accgagcgca gcgagtcagt  11220
gagcgaggaa gcggaagagc gcccaatacg caaaccgcct ctccccgcgc gttggccgat  11280
tcattaatgc agctgcacg acaggtttcc cgactggaaa gcgggcagtg agcgcaacgc  11340
aattaatgtg agttagctca ctcattaggc accccaggct ttacacttta tgcttccggc  11400
tcgtatgttg tgtggaattg tgagcggata acaatttcac acaggaaaca gctatgacat  11460
gattacgaat ttaatacgac tcacaatagg gaattagctt gcgcgaaatt attggctttt  11520
ttttttttttt aattaaaaga aaacattctc tagggattac gaggtaaaga tacatttttca  11580
aggcttattc gattctgtga actcagttgg aatattaagg gacaggttgt ttccttgcac  11640
ccagagaagc aatatcgttg agcatgttcg acattgcgta tccttggatg aaagacgtgg  11700
aaaattcaag cagttatgtt tcactccgat gccgtacatt ccgaaactat tttcattgac  11760
atattgtaat catataactg accagtgttc gccggtgcca acttctaatg cattaatgcg  11820
tgatctaacc ccgaaaatc ctttgataaa atacactttta aaagtggcg cacattctat  11880
tagtaatcct tctccactca ttcctgataa ccctggaagg ttgttatcga gcaaaagcga  11940
ggaaactaca gagttgctgt tggacctgaa ctcattctta aaggtaatt catacgcgag  12000
agatacagaa tgttcaacaa gaggaattga agccattttc caacttcaat ctatccaagg  12060
cagcggtaca tcaagtagaa tgactatgac acccgacttg attgaaaaat ggtttccagg  12120
tgatcggcca tcttggccga tcattctgac gttggtggag gttgggcgcc tgactgtgag  12180
acagaagaga acttgtcaaa tttaacgctg cgatggattt tagcagaggc aatcaaattt  12240
ggtgttaaat tcaaacctgg tgcaatacat gatttcgcta ccaaacacac ttcgattgga  12300
tctttattcg cagacacaca tgattacctt agtttcaact caccaaagaa atgttcccta  12360
ctaggagtga gtgataatga ggatggagcc cgagaggata aatctggcag aaatgagaga  12420
atggaagatt gtctaaaaaa tataaaagag actagattga gcttgaaaga tgaaaaagaa  12480
aaagtgaagg atgcttttac tcttaaatgt ggacatgcaa ataaatttat gagattggtg  12540
tggtgggtat tggaactgct ccccattgga atacgaatgg aaaataaaga aggaaagtgg  12600
caaaattttc atacacctaa cctcggaaga tcgtcgacaa gcttgtggag aggtgacttc  12660
atgaaccaag tgtctgtcga tatacaacaa aaaggaacca ttttcatctt gatggacaac  12720
atgtgcatca aaaccttat cgtaaagagt tcttggaccc ttggatggag tgtaaaccat  12780
gatttaaaac agcaaataat aaaaatcgat agcgacaaaa actgtcaatt tcaatattct  12840
ttatatttgt tgactgctta gatattttga gaaaattcag cggaaacagc gtgatgagtg  12900
agttaagttc tgctgtttaa ataagtattc aactactatt gaagccgact catgaagccg  12960
gttacggaca aaaccgggca aatttcgccg gtcccggaat tttcgtttcc gcaataaaag  13020
```

```
aaccgctcat catcatagcg ccagggtagt atactataga aggtcagact aaactgagtc    13080
atctagagta atgacgcctt agtagctttt acatcttcat aagaaaagga aacttgtaga    13140
atggcctggc gatttgtttg ctttcttgtg atgaagaaat ttcgatgcga ttaaccggca    13200
aaatcagtaa aggtatttcg cggaggcggc cttcaatcat cgaatactac gtcttaatat    13260
gatgtactgt ggttcatatt ttcaagtagt gttagtaaat ttgtatacgt tcatgtaagt    13320
gtgtatcttg agtgtctgta tgggcgcata aacgtaagcg agacttccaa atggagcaaa    13380
cgagaagaga tctttaaagt attatagaag agctgggcag gaactattat gacgtaaagc    13440
cttgaccata ataaagacga ttctttgtcc ctctatacaa acatcttgca aagataccaa    13500
atattttcaa atcctactca ataaaaaatt aatgaataaa ttagtgtgtg tgcattatat    13560
atattaaaaa ttaagaatta gactaaataa agtgtttcta aaaaaatatt aaagttgaaa    13620
tgtgcgtgtt gtgaattgtg ctctattaga ataattatga cttgtgtgcg tttcatattt    13680
taaaatagga aataaccaag aaagaaaaag taccatccag agaaaccaat tatatcaaat    13740
caaataaaac aaccagcttc ggtgtgtgtg tgtgtgtgaa gctaagagtt gatgccattt    13800
aatctaaaaa ttttaaggtg tgtgtgtgga taaaatatta gaatgacaat tccccggaat    13860
tgcgtacgct taatccttgg cagaaatcat gtcctcaggt ctaacccatt ggtcgaattc    13920
ttcagaggtc aagtaaccca aagatagagc agcttctttc aaagtggtac cttccttgtg    13980
agccttcttg gcacacttgg cagccttgtc gtaaccaatg tgagggttca aagcagtgac    14040
caacatcaaa gattcgttca tgatggagga gatcttcttt tcgttagctt caataccgac    14100
aacacagttc ttggtgaaag agatggaagc gtcagagatt aatctgatgg attggatcaa    14160
gttcttgatc atgactggtt taaagacatt caattcgaat tgaccgttgg aaccagcaac    14220
agagatggca gtgttgttac ccatgacttg agcacaaacc atggtcatag cttcacattg    14280
agttgggttg accttacctg gcatgatgga agaacctggt tcgttttctg gtagagacaa    14340
ttcacctaaa ccacatcttg gaccagaacc caagtaacgg atatcgttgg caatcttcat    14400
caaagaacaa gcaacggtgt tcaaagcacc gtgagcttca accaaagcgt cgtgagcagc    14460
caaagcttcg aatttgtttg gagcggtctt gaatggtaaa ccagtgatgg aagcaatggc    14520
ttcagcaacc ttggcatcga aacccttcct ggtgttcaaa ccagtaccga cagcagtacc    14580
accttgagcc aagttgtata atcttttccaa agtaccttga acacgagcaa taccgtaggt    14640
caattgttga gtgtaaccgg agaattcttg acctaaagtc aatggggtag catcttgcaa    14700
gtgggttcta ccaatcttga tgatgtgttc gaattcagca gatttggctt gcaaagcatc    14760
tctcaaagtg gtcaaagctg gaatcaatct accgtgaatt tcaacaacgg cagcaacgtg    14820
catggcagtt gggaaagtgt cgttggaaga ttgagacatg ttgacatgat cgtttgggtg    14880
gactggagcc ttgaaccta attcaccacc caacaattca atggctctgt tggagatgac    14940
ttcattgacg ttcatcttgg tttgagtacc agaaccggtt tgccagacaa ccaatggaa     15000 atggtcaatc aaagaaccat cgataacttc gtcagcagcc ttttggatgg cttcaccaac    15060
ctttgggtcc aaaccgtagg tcatgttgac ggtggcagca gccttcttca aaacaccgaa    15120
agctctgatt aatggttctg gcattctttc agttggacca ccaatgtcaa agttttgcaa    15180
agatctttga gtttgagcac cccagtaacg gtcagctgga acttgcaagt caccgaaggt    15240
atctctttca gctctgaatt tttgcaaagc agcagaagca gaggcacttt tttgtttatg    15300
tatgtgtttt ttgtagttat agatttaagc aagaaaagaa tacaaacaaa aaattgaaaa    15360
```

```
agattgattt agaattaaaa agaaaaatat ttacgtaaga agggaaaata gtaaatgttg   15420
caagttcact aaactcctaa attatgctgc cctttatatt ccctgttaca gcagccgagc   15480
caaaggtata taggctcctt tgcattagca tgcgtaacaa accacctgtc agtttcaacc   15540
gaggtggtat ccgagagaat tgtgtgattg ctttaattaa tttcggagaa tctcacatgc   15600
cactgaagat taaaaactgg atgccagaaa aggggtgtcc aggtgtaaca tcaatagagg   15660
aagctgaaaa gtcttagaac gggtaatctt ccaccaacct gatgggttcc tagatataat   15720
ctcgaaggga ataagtaggg tgataccgca gaagtgtctg aatgtattaa ggtcctcaca   15780
gtttaaatcc cgctcacact aacgtaggat tattataact caaaaaaatg gcattattct   15840
aagtaagtta aatatccgta atctttaaac actatgtagt taggtctcgc ggccgcattt   15900
aaatggagga aatgagaaat gagaggtatg taaatagaaa tagactagct ccacttttaa   15960
gaattattta tgcaattaaa tacatgggtg accaaaagag cgggcggata cccgcgtcac   16020
cacaagcaga ataaaaggta aacctgaaat tgttttaaca taaaatgaaa aatgcttgtt   16080
tgcaacccta tatagaatca taaaacattc gtgactataa aatgaataaa ctaaactatt   16140
ctaagaaaat gaaataaatg acaaaaaaac gtgttttttg gactagaagg cttaatcaaa   16200
agctcttatt cagaaacatc ttcatcttga cctggccaca tgatgtcctt tctgatgaca   16260
gctctgatgg cagaaaccaa gacgaaaata aacatgatga tgacacatag ggacatagca   16320
gtggcaacac ccttgacacc tggagattcg aacatgttag ccaaagtgat ggtagccaag   16380
gtgaaaccag tgtttgggaa accatggca aaccagttca aatggaaacc ctttggtgga   16440
gatctgacaa cagcaacaac agcgatacag aagaaccaga aagacaaagc cataagaag   16500 atggcagcag agacagccaa gaacaacata acacgaccgt caatgacagc gtgagggtca   16560
ccgacaattt ggaagtcgtc tggtaaagcc ttggccatac cgaccaaagc caaagcggtg   16620
aaagctggag gaccaacaca gatgaacata cctggtctgt gttctggaga tggtaaacca   16680
acttccatca atctaccaat gtagtgagcg tacatcatga aggagatgga gaaacctaaa   16740
ccttggaaag tgataccagc aataataatt ggaataccat cggaagctgg ttgaccagaa   16800
ccgatgacgg aggcgatagt accagacaac ataactggga aagctggcaa gatccaggat   16860
ggcatcatgg tgtgcaattc gtatttgtgg gtagcaaaga cgaaagagta ttgaccgaca   16920
gcagtgatca tggtacaacc acagtagatc cagaacaaaa cttgcaaaca cttggtgaac   16980
ttttcgttag catcatcacc gaaacacttg tacaaaccag tgatcatggt agcaatggat   17040
aaccagaaag ttgggaaaaa caaaccttct ctgtcgtgac ccaaggattc ccacatgttc   17100
ttgtgcaaga tgaatctgat ggccatcaaa gaggtaacga taacaaagaa agccaagttc   17160
aaacagtaga caactctggc aatatctttc aaaccttga agtcgtgtgg ttggttgaca   17220
atcaacaaag ccaaccacc acaggacatg gtcaaagtgt accagcccca ggtgaagtga   17280
cgtaatcttt ctctgatacc aactggacct ggcttttcga aagtgtggtt aacaccaatt   17340
tcagcttcat ggttgacgga ataccagag tcgtggttgg catgcttctt ggtttcgtgg   17400
tggaaagttt ccaagtcaga accagaagaa cctggcaaag aagtttcaac gttcattttg   17460
ttttagtgtt tgtgtgttga taagcagttg cttggttttt tatgaaaaat agctagaagg   17520
aataagggat tacaagagag atgttacaag aaagaagtaa aataaatttg attaatattg   17580
ccattatcaa aagctatta tatgttgaaa tcgtggagat catgtgtgcc agaaaaggcc   17640
acagtttccg gggagaggca taccttgagg tggctaggaa tcacgagac ctcttgactt   17700 gcagggtagg ctagctagaa ttaagtgagg tgacaaggtt tccatacagt tttgaccttg   17760
```

```
agacgttgct acttacgatt tgcagtatgc aagtctcatg ctgcaaacaa aagaggaccg  17820
ctcaggtaat cgctcaatta gtggacgtta tcaggggcgg gagaggcgaa agtggttttt  17880
ggtggtgtaa gtaaaggtcg tccaaatatg caggtgtttg ggtgctatcc tagtggaagc  17940
tcggatcagt agataacccg cctagaagcg gtattttct ttttttttct tccttcttt  18000
tcgtcattat ttcaaacgct tttgcgtcaa gtaatgaata tctggcggtt ccgcggggcg  18060
cgccggatcc gggccgcata ggccactagt ggatctgatt cgaattctac cgttcgtata  18120
gcatacatta tacgaagtta tgagctcgtt ttcgacactg gatggcggcg ttagtatcga  18180
atcgacagca gtatagcgac cagcattcac atacgattga cgcatgatat tactttctgc  18240
gcacttaact tcgcatctgg gcagatgatg tcgaggcgaa aaaaaatata aatcacgcta  18300
acatttgatt aaaatagaac aactacaata taaaaaaact atacaaatga caagttcttg  18360
aaaacaagaa tcttttatt gtcagtactg attagaaaaa ctcatcgagc atcaaatgaa  18420
actgcaattt attcatatca ggattatcaa taccatattt ttgaaaaagc cgtttctgta  18480
atgaaggaga aaactcaccg aggcagttcc ataggatggc aagatcctgg tatcggtctg  18540
cgattccgac tcgtccaaca tcaatacaac ctattaattt cccctcgtca aaaataaggt  18600
tatcaagtga gaaatcacca tgagtgacga ctgaatccgg tgagaatggc aaaagcttat  18660
gcatttcttt ccagacttgt tcaacaggcc agccattacg ctcgtcatca aaatcactcg  18720
catcaaccaa accgttattc attcgtgatt gcgcctgagc gagacgaaat acgcgatcgc  18780
tgttaaaagg acaattacaa acaggaatcg aatgcaaccg gcgcaggaac actgccagcg  18840
catcaacaat attttcacct gaatcaggat attcttctaa tacctggaat gctgttttgc  18900
cggggatcgc agtggtgagt aaccatgcat catcaggagt acggataaaa tgcttgatgg  18960
tcggaagagg cataaattcc gtcagccagt ttagtctgac catctcatct gtaacatcat  19020
tggcaacgct acctttgcca tgtttcagaa acaactctgg cgcatcgggc ttcccataca  19080
atcgatagat tgtcgcacct gattgcccga cattatcgcg agcccattta tacccatata  19140
aatcagcatc catgttggaa tttaatcgcg gcctcgaaac gtgagtcttt tccttaccca  19200
tggttgttta tgttcggatg tgatgtgaga actgtatcct agcaagattt taaaaggaag  19260
tatatgaaag aagaacctca gtggcaaatc ctaacctttt atatttctct acagggcgc  19320
ggcgtgggga caattcaacg cgtctgtgag gggagcgttt ccctgctcgc aggtctgcag  19380
cgaggagccg taattttgc ttcgcgccgt gcggccatca aaatgtatgg atgcaaatga  19440
ttatacatgg ggatgtatgg gctaaatgta cgggcgacag tcacatcatg cccctgagct  19500
gcgcacgtca agactgtcaa ggagggtatt ctgggcctcc atgtcgctgg ccgggtgacc  19560
cggcggggac gaggcaagct aaacagatct ataacttcgt atagcataca ttatacgaac  19620
ggtagaattc gtcgacctgc agcgtacgaa gcttcagctg gcggcc              19666
```

PROCESS FOR PREPARING DICARBOXYLIC ACIDS EMPLOYING FUNGAL CELLS

CROSS REFERENCE TO RELATED APPLICATIONS

This application is a §371 National Stage Application of PCT/EP2012/062860, filed Jul. 2, 2012, which claims priority to European Application No. 111724444.9, filed Jul. 1, 2011.

BACKGROUND OF THE INVENTION

Field of the Invention

The present invention relates to a process for the production of a dicarboxylic acid.

Description of Related Art

Several processes for the production of a dicarboxylic acid are known. WO2007/061590 discloses a process for the production of malate and succinate in the presence of 21% of oxygen and up to 15% of carbon dioxide. It was shown that in the presence of 10% carbon dioxide a higher amount of malate and succinate was produced compared to 0% added carbon dioxide.

WO2008/144626 shows that the addition of carbon dioxide of up to 10 v/v % increased production levels of malic acid and succinic acid by a recombinant yeast cell, but higher concentrations of carbon dioxide did not increase these levels further.

WO2011/023700 discloses an increase in the production of malic acid and succinic acid by a recombinant yeast by fermenting the recombinant yeast in the presence of a carbon dioxide concentration ranging between 25% and 75 v/v %.

A disadvantage of the processes as disclosed in WO2007/061590, WO2008/14462 and WO2011/023700 is that a separate carbon dioxide gas stream needs to be added to the fermentation in addition to air.

WO2010/118932 discloses an anaerobic process for the production of dicarboxylic acid and ethanol. The production of ethanol allowed the production of energy for maintenance of the cell, and the simultaneous production of carbon dioxide would positively influence the production of dicarboxylic acid. A disadvantage of a process as disclosed in WO2010/118932 is that anaerobic conditions limit the ways for cell maintenance and reduces the yield of dicarboxylic acid.

The present disclosure aims to provide an improved method for the fermentative production of a dicarboxylic acid which overcomes the disadvantages outlined above.

SUMMARY

The present invention relates to a process for producing a dicarboxylic acid comprising fermenting a yeast strain in a vessel comprising a suitable fermentation medium, comprising adding a gas comprising about 20 to about 35 v/v % of oxygen and less than about 0.1 v/v % carbon dioxide to the fermentation medium, and maintaining an average partial carbon dioxide pressure of at least about 0.35 bar in the fermentation medium, and producing the dicarboxylic acid.

A suitable gas may be air, for instance oxygen enriched air. Oxygen enriched air is air with an increased concentration of oxygen as compared to air.

A combination of oxygen enrichment and overpressure may thus be used to achieve the invention.

We have found that an optimal dicarboxylic acid yield can be obtained at a partial pressure of carbon dioxide of at least about 0.35 bar.

An advantage of a process according to the present invention is that there is no need for a separate carbon dioxide gas stream for sufficiently high carbon dioxide partial pressure.

The terms "dicarboxylic acid" and "dicarboxylate", such as "succinic acid, or malic acid" and "succinate and malate" have the same meaning herein and are used interchangeably, the first being the hydrogenated form of the latter.

The term fermenting or fermentation as used herein refers to the microbial production of compounds such as alcohols or acids from carbohydrates.

A genetically modified or recombinant yeast, or genetically modified or recombinant yeast cell according to the present disclosure is defined herein as a cell which contains a disruption of a gene or contains, or is transformed or genetically modified with a nucleotide sequence that does not naturally occur in the yeast cell, or it contains additional copy or copies of an endogenous nucleic acid sequence. A wild-type yeast cell is herein defined as the parent cell of the recombinant cell.

The term "homologous" when used to indicate the relation between a given (recombinant) nucleic acid (DNA or RNA), gene or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid, gene or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "enzyme" as used herein is defined as a protein which catalyses a (bio)chemical reaction in a cell.

There are known methods in the art for overexpression of genes encoding enzymes. A gene encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of one or more gene(s). Preferably, overexpression of a gene encoding an enzyme according to the invention is achieved with a (strong) constitutive promoter.

Suitable promoters in fungal cells are known to the skilled man in the art. Suitable promotors may be, but are not limited to, TDH1, TDH3, GAL7, GAL10, GAL1, CYC1, HIS3, ADH1, PH05, ADC1, ACT1, TRP1, URA3, LEU2, ENO1, TPI1, AOX1, PGL, GPDA and GAPDH. Other suitable promoters include PDC1, GPD1, PGK1, and TEF1.

A gene encoding an enzyme may be ligated into a nucleic acid construct, for instance a plasmid, such as a low copy plasmid or a high copy plasmid. The fungal cell according to the present invention may comprise a single copy, but preferably comprises multiple copies of a gene, for instance by multiple copies of a nucleotide construct.

A nucleic acid construct may be maintained episomally and thus comprises a sequence for autonomous replication, such as an autonomously replicating sequence and a centromere (Sikorski and Hieter, 1989, Genetics 122, 19-27). A suitable episomal nucleic acid construct may e.g. be based on the yeast 2µ or pKD1 plasmids (Gleer et al., 1991, Biotechnology 9: 968-975), or the AMA plasmids (Fierro et al., 1995, Curr. Genet. 29:482-489). Alternatively, each nucleic acid construct may be integrated in one or more copies into the genome of the fungal cell. Integration into the cell's genome may occur at random by non-homologous recombination but preferably, the nucleic acid construct may be integrated into the cell's genome by homologous recombination as is well known in the art.

DETAILED DESCRIPTION OF A PREFERRED EMBODIMENT

Figure 1:
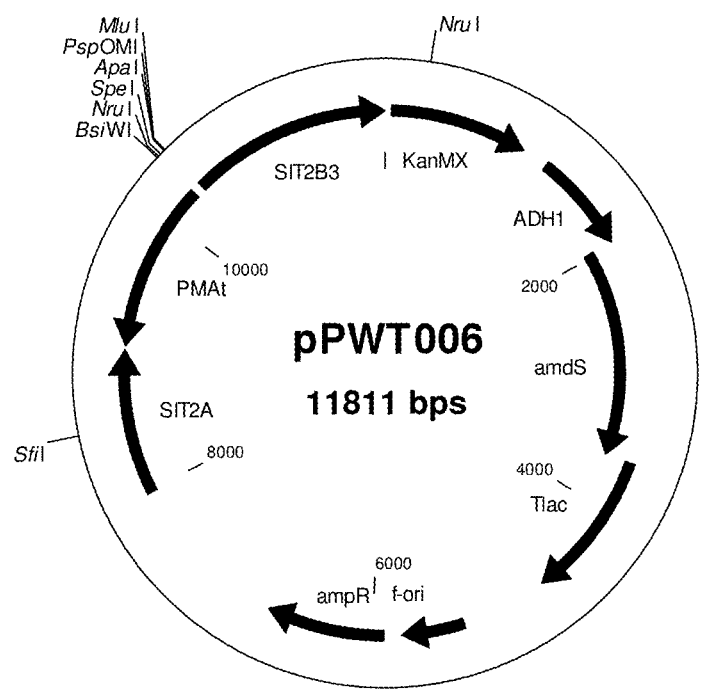
FIGS. 1-13 represent embodiments as described herein.

An average partial pressure of carbon dioxide as used herein is the average partial pressure of carbon dioxide measured over the total height of the fermentation vessel. Usually, the partial pressure of a gas such as carbon dioxide at a specific location in a fermentation vessel is a result of, a.o., the pressure in the headspace of a fermentation vessel and the pressure of liquid (fermentation medium) above that location.

The present invention relates to a process for producing a dicarboxylic acid comprising fermenting a yeast strain in a vessel comprising a suitable fermentation medium, comprising adding a gas comprising about 20 to about 35 v/v % of oxygen and less than about 0.1 v/v % carbon dioxide to the fermentation medium, and maintaining an average partial carbon dioxide pressure of at least about 0.35 bar in the fermentation medium, and producing the dicarboxylic acid.

The invention thus relates to a process for producing a dicarboxylic acid comprising fermenting a fungal cell in a vessel comprising a suitable fermentation medium, comprising adding a gas which comprises 20 to 35 v/v % of oxygen and less than 0.1 v/v % of carbon dioxide to the fermentation medium, and maintaining an average partial carbondioxide pressure of between 0.35 to 0.6 bar in the fermentation medium, and producing the dicarboxylic acid.

The average partial pressure of carbon dioxide may be between about 0.35 and about 1.0 bar, for example between about 0.35 and about 0.8 bar, for example between about 0.35 and 0.65 bar, such as between about 0.35 and about 0.6 bar.

An average partial pressure of carbon dioxide of at least about 0.35 bar in a process as disclosed herein can be obtained by any suitable means. For instance a vessel in a process as disclosed herein may comprise a headspace pressure of between about 1.05 to about 5 atmosphere, for instance between about 1.2 and about 4 atmosphere, for instance between about 1.5 and about 2.5 atmosphere.

A vessel in a process according to a process as disclosed herein may have any suitable height and diameter. The vessel may for instance have a height of from about 1 to about 50 m, such as from about 5 to about 40 m, or from about 10 to about 25 m.

Usually the headspace pressure is adjusted to the height of the fermentation vessel such that an average partial pressure of carbon dioxide of at least about 0.35 bar in the fermentation medium is maintained.

We found that the partial pressure of carbon dioxide of at least about 0.35 bar in a process as disclosed herein is, amongst others, the result of respiratory activity of a fungal cell, the oxygen content in the gas, flow rate of the gas and pressure at a specific location in the fermentation vessel. For instance, depending on the oxygen concentration in the gas added to the fermentation medium, the pressure applied in the headspace of a fermentation vessel can be adjusted such that a partial pressure of carbon dioxide of at least about 0.35 bar is obtained.

A process for producing a dicarboxylic acid as disclosed herein for example comprises adding a gas which comprises from about 21 to about 32 v/v % of oxygen, for example from about 22 to about 32 v/v %, for example from about 22 to about 30 v/v % of oxygen, or from about 25 to about 29 v/v % of oxygen and less than about 0.1% of carbon dioxide.

A suitable gas may be air, for instance oxygen enriched air. Oxygen enriched air is air with an increased concentration of oxygen as compared to air. An advantage of an increased concentration of oxygen compared to the normal concentration of oxygen in air in a process of the invention was that a higher average partial carbon dioxide pressure could be generated to produce a sufficiently high amount of succinic acid.

The gas in a process for producing a dicarboxylic acid according to the present invention may be added to the vessel at any suitable location, for instance at the lower half of the fermentation vessel. The gas may be added at one or more locations in the fermentation vessel.

In one embodiment a process of the present disclosure comprises adding a gas comprising oxygen at a flow rate of between about 0.02 to about 0.05 cubic metre/cubic metre/ min, for instance between about 0.025 to about 0.045 cubic metre/cubic metre/min. In the event a gas comprises oxygen enriched air, a lower flow rate may be applied than in the event gas comprises air.

In another embodiment, a process as disclosed herein comprises stirring the fermentation medium. Stirring a fermentation medium may be carried out in any suitable way known to a skilled person in the art. Stirring may be performed such that the fermentation vessel has a power input of between about 0.070 to about 0.26 kW/cubic metre, for instance between about 0.1 and about 0.2 kW/cubic metre, for instance between about 0.13 and about 0.2 kW/cubic metre.

A process for producing a dicarboxylic acid as disclosed herein may be carried out in any suitable fermentation mode, such as batch, fed-batch, a continuous process or any suitable combination of these fermentation modes.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted A continuous fermentation is a fermentation wherein nutrients are continuously added to the fermentation and wherein products are continuously removed from the fermentation The fermentation medium in a process for producing a dicarboxylic acid as disclosed herein may comprise any suitable nutrients, such as a carbon source and a nitrogen source, allowing yeast to produce a dicarboxylic acid. A skilled person in the art knows the suitable composition of fermentation media for a specific yeast strain.

A suitable fungal cell in a process as disclosed herein may belong to any suitable genera *Saccharomyces, Aspergillus, Penicillium, Pichia, Kluyveromyces, Yarrowia, Candida, Hansenula, Humicola, Issatchenkia, Torulaspora, Trichosporon, Brettanomyces, Rhizopus, Zygosaccharomyces, Pachysolen* or *Yamadazyma*. A fungal cell may for instance belong to a species of *Saccharomyces cerevisiae, Saccharomyces uvarum, Saccharomyces bayanus, Aspergillus niger, Penicillium chrysogenum, Pichia stipidis, Kluyveromyces marxianus, K. lactis, K. thermotolerans, Yarrowia lipolytica, Candida sonorensis, C. glabrata, Hansenula polymorpha, Issatchenkia orientalis, Torulaspora delbrueckii, Brettanomyces bruxellensis, Rhizopus oryzae* or *Zygosaccharomyces bailii*. In one embodiment a fungal cell in the process of the present invention is a yeast, for instance belonging to a *Saccharomyces* sp., such as a *S. cerevisiae*.

A fungal cell in a process as disclosed herein may be any suitable wild type or recombinant or genetically modified fungal cell. A genetically modified fungal cell may comprise a genetic modification of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter.

A recombinant fungal cell may comprise a genetic modification with a pyruvate carboxylase (PYC), that catalyses the reaction from pyruvate to oxaloacetate (EC 6.4.1.1). The pyruvate carboxylase may for instance be active in the cytosol upon expression of the gene. For instance the fungal cell overexpresses a pyruvate carboxylase, for instance an endogenous or homologous pyruvate carboxylase is overexpressed.

A recombinant fungal cell may further comprise a gene encoding a phosphoenol pyruvate (PEP) carboxykinase (4.1.1.49) A fungal cell may be genetically modified with a heterologous PEP carboxykinase, such as a PEP carboxykinase derived from *Escherichia coli, Mannheimia* sp., *Actinobacillus* sp., or *Anaerobiospirillum* sp., for instance *Mannheimia succiniciproducens, Actinobacillus succinogenes,* or *Anaerobiospirillum succiniciproducens*. A gene encoding a PEP carboxykinase may be overexpressed and may be expressed and active in the cytosol of a fungal cell.

In one embodiment a fungal cell is further genetically modified with a gene encoding a malate dehydrogenase (MDH) active in the cytosol upon expression of the gene. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae*.

In another embodiment a fungal cell of the present disclosure is further genetically modified with a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*, or a bacterium such a *Escherichia coli*. A fungal cell of the present disclosure may overexpress a nucleotide sequence encoding a fumarase. The fumarase may be active in the cytosol upon expression of the nucleotide sequence, for instance by deleting a peroxisomal targeting signal. It was found that cytosolic activity of a fumarase resulted in a high productivity of a dicarboxylic acid by the fungal cell.

In another embodiment the fungal cell is genetically modified with any suitable heterologous or homologous gene encoding a NAD(H)-dependent fumarate reductase, catalyzing the reaction from fumarate to succinate (EC 1.3.1.6). The NADH-dependent fumarate reductase may be a heterologous enzyme, which may be derived from any suitable origin, for instance bacteria, fungi, protozoa or plants. A fungal cell of the present disclosure comprises a heterologous NAD(H)-dependent fumarate reductase, preferably derived from a *Trypanosoma* sp, for instance a *Trypanosoma brucei*. In one embodiment the NAD(H)-dependent fumarate reductase is expressed and active in the cytosol, for instance by deleting a peroxisomal targeting signal. The fungal cell may overexpress a gene encoding a NAD(H)-dependent fumarate reductase.

In another embodiment the fungal cell may comprise a genetic modification with a gene encoding a dicarboxylic acid transporter protein, for instance a malic acid transporter protein. A dicarboxylic acid transporter protein may be a homologous or heterologous protein, for instance derived from from *Schizosaccharomyces pombe* or *Aspergillus niger*. A fungal cell as disclosed herein may overexpress a dicarboxylic acid transporter protein.

A genetically modified fungal cell may further comprise a genetic modification with a gene encoding an isocitrate lyase (EC 4.1.3.1), which may be any suitable heterologous or homologous enzyme. The isocitrate lyase may for instance be obtained from *Kluyveromyces lactis* or *Escherichia coli*.

A genetically modified fungal cell may further comprise as genetic modification with a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxy-terminal sequence.

Cytosolic expression of the enzymes described above may be obtained by deletion of a peroxisomal or mitochondrial targeting signal. The presence of a peroxisomal or mitochondrial targeting signal may for instance be determined by the method disclosed by Schlüter et al., Nucleid Acid Research 2007, 35, D815-D822.

In another embodiment, a recombinant fungal cell in the process for producing a dicarboxylic acid disclosed herein comprises a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a fungal cell in the process as disclosed herein comprises a disruption of one, two or more genes encoding an alcohol dehydrogenase. In the event the fungal cell is a yeast, e.g. S. cerevisiae, the yeast preferably comprises a disruption of an alcohol dehydrogenase gene adh1 and/or adh2.

A dicarboxylic acid that is produced in a process as disclosed herein may be succinic acid, fumaric acid, malic acid or adipic acid, for instance succinic acid.

In one embodiment, a dicarboxylic acid that is produced in a process as disclosed herein is recovered from the fermentation medium. Recovery of a dicarboxylic acid may be carried out by any suitable method known in the art, for instance by crystallization, ammonium precipitation, ion exchange technology, centrifugation or filtration or any suitable combination of these methods.

A process for producing a dicarboxylic acid may be carried out at any suitable pH and temperature. A suitable pH may be between about 2 and about 8, for instance between about 2.5 and about 6, for instance between about 3 and about 5. A suitable temperature may for instance be between about 10 and about 40 degrees Celsius, for instance between about 15 and about 30 degrees Celsius.

FIGURES

Figure 2:
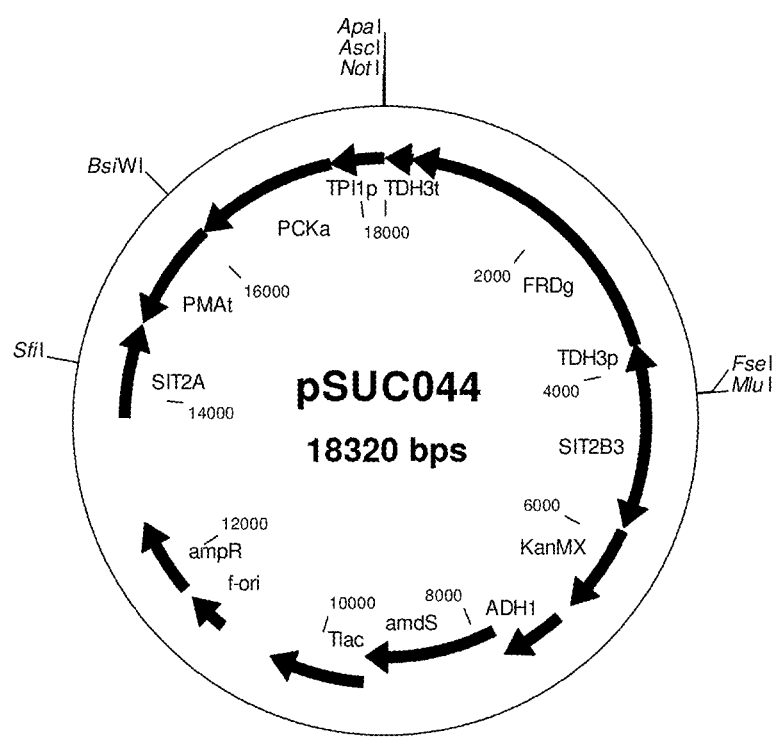
Figure 3:
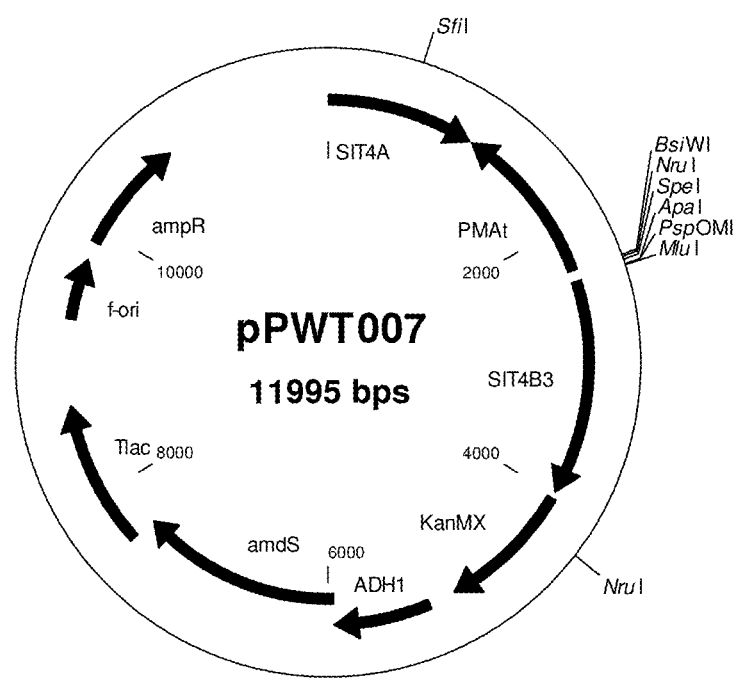
Figure 4:
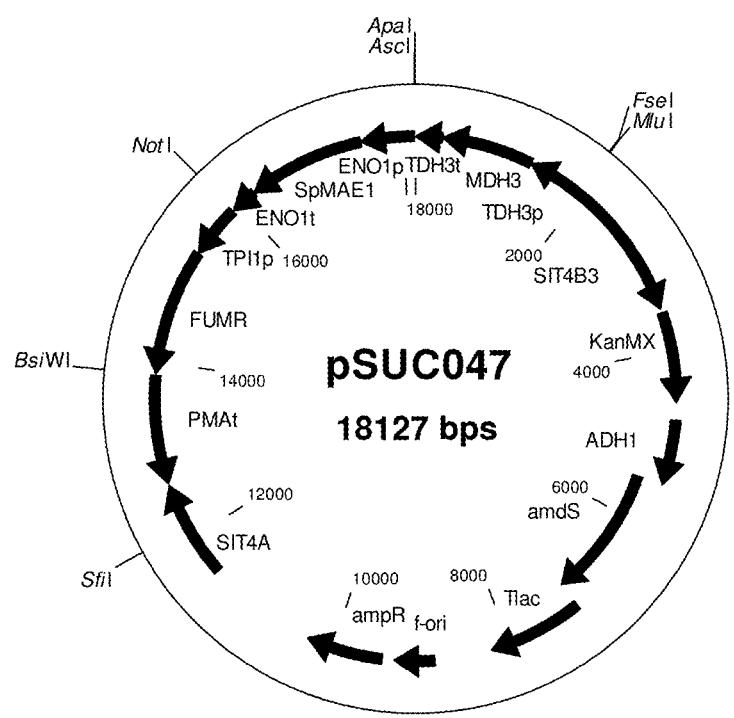
Figure 5:
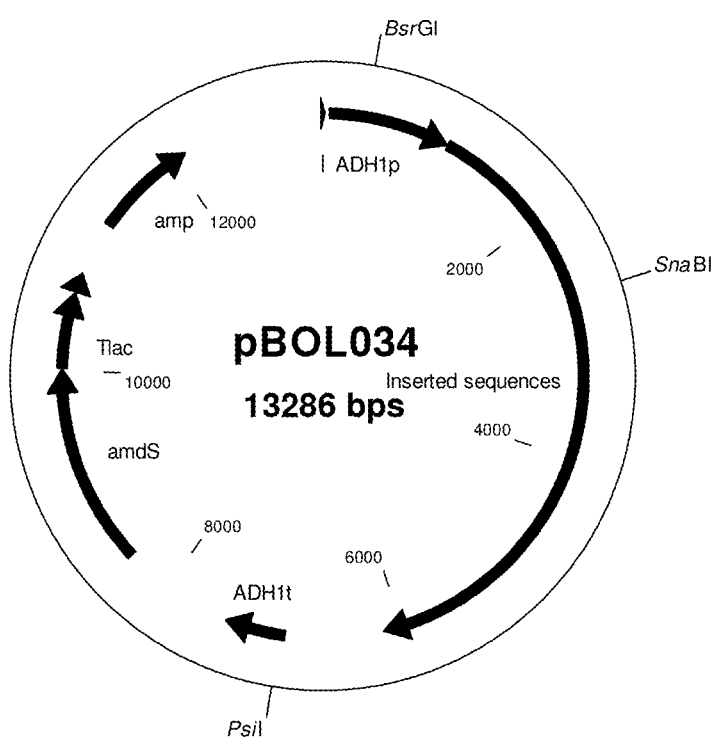
Figure 6:
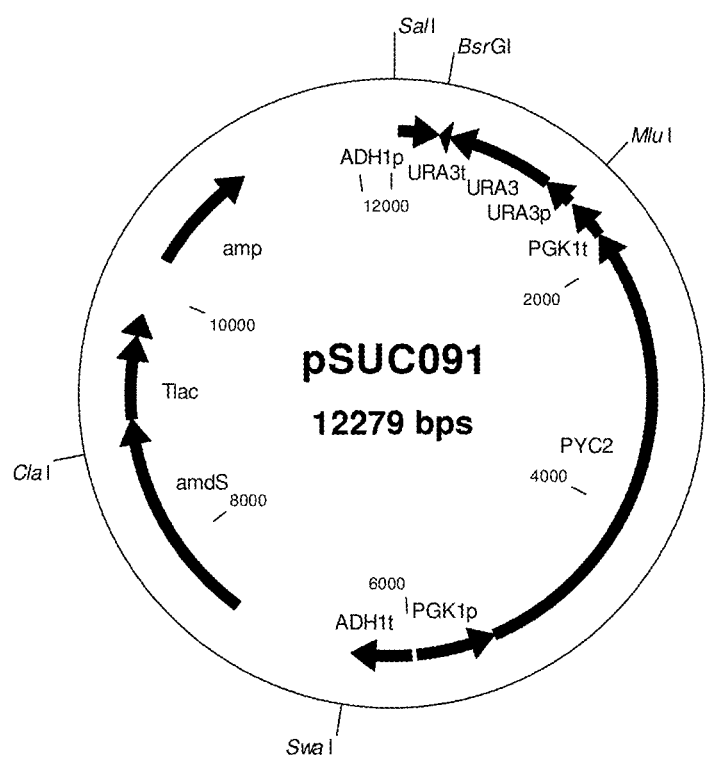
Figure 7:
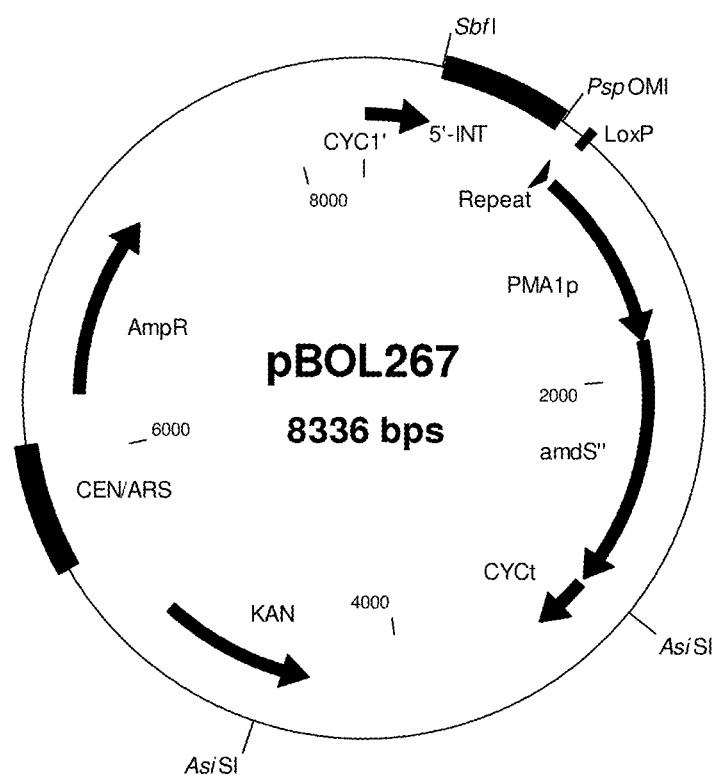
Figure 8:
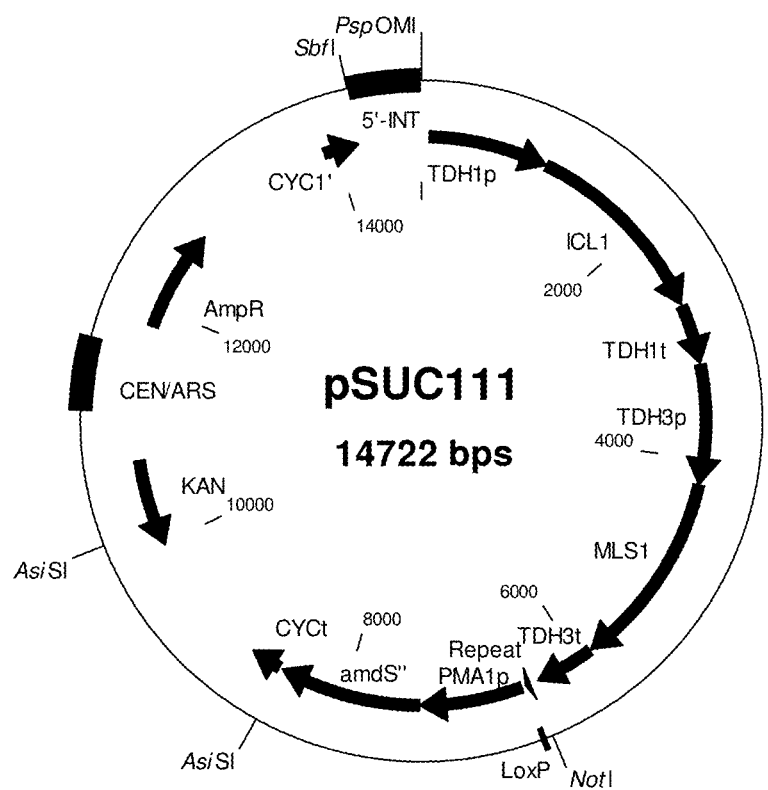
Figure 9:
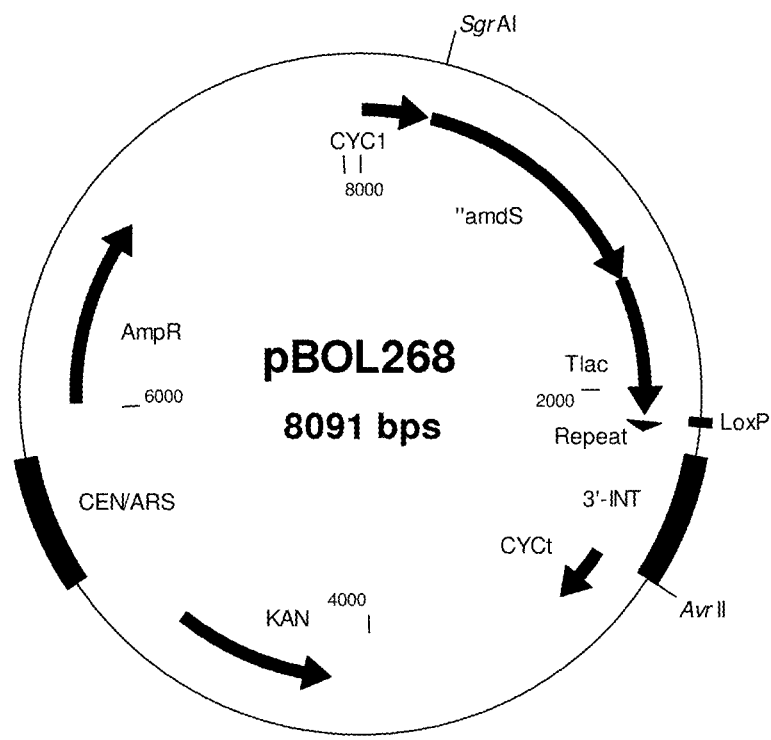
Figure 10:
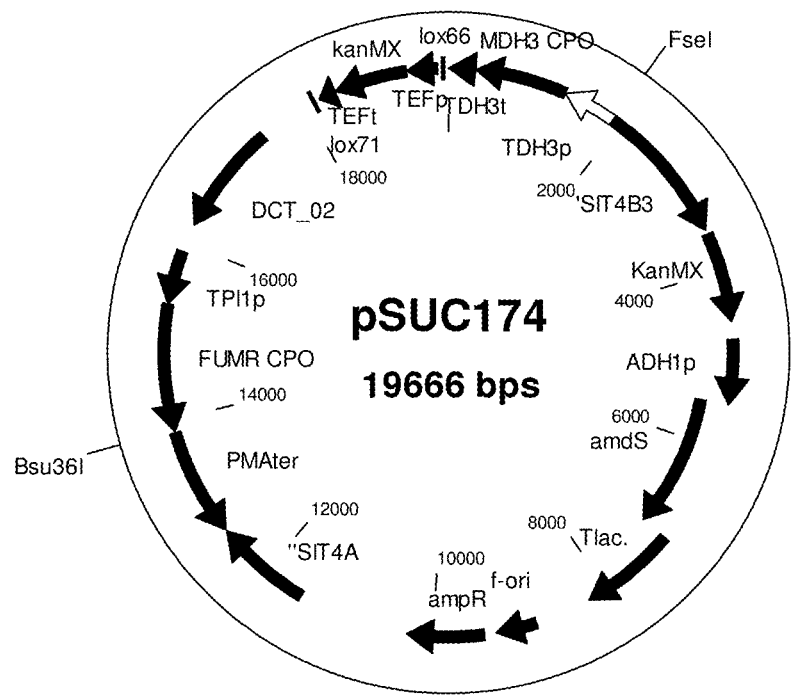
Figure 11:
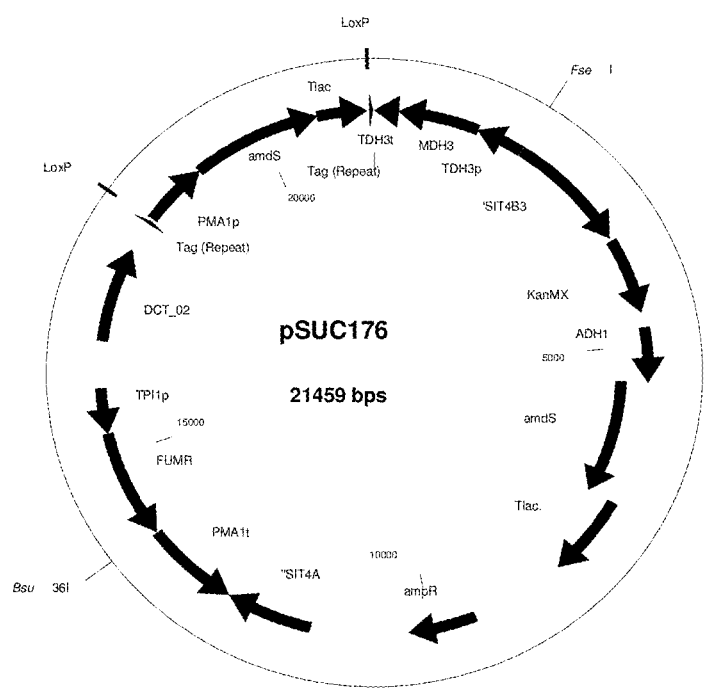
Figure 12:
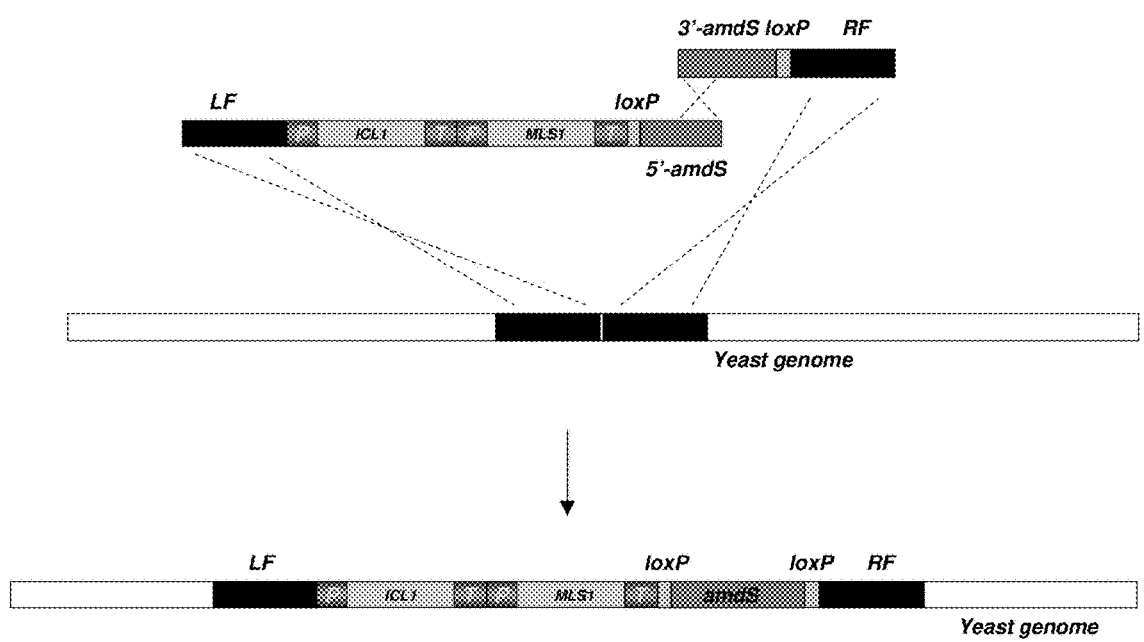

FIG. 1 Physical map of plasmid pPWT006.
FIG. 2 Physical map of plasmid pPSUC044.
FIG. 3 Physical map of plasmid pPWT007.
FIG. 4 Physical map of plasmid pSUC047.
FIG. 5 Physical map of pBOL034.
FIG. 6 Physical map of pSUC091.
FIG. 7 Physical map of pBOL267.
FIG. 8 Physical map of pSUC111.
FIG. 9 Physical map of pBOL268.
FIG. 10 Physical map of pSUC174.
FIG. 11 Physical map of pSUC176.
FIG. 12 Basic principle of the integration method used for integration of the KlICL1 and MLS1 synthetic genes. Two fragments are transformed to yeast. A 'LF' (for Left flank) fragment and a 'RE' fragment (for Right Flank). In the LF fragment, the LF is placed 5' from the KlICL1 and MLS1 synthetic genes. 3' of the gene is a loxP site, and a 3' truncated amdS gene. In the RF fragment, the RF is placed 3' from a multiple cloning site, in which more genes can be introduced. 5' of the multiple cloning site is a loxP site, and a 5' truncated amdS gene. The LF and RF fragments can be joined in vivo via homologous recombination on the amdS gene. The LF and RF flanks are homologous to adjoining sequences in the yeast genome, allowing double-crossover-integration of the joined LF and RF fragments. The truncated amdS fragments individually do not code for active proteins, but recombination of the two fragments leads to the ability to utilize Acetamide as N-source. Transformed cells that posses active amdS thus will have the KlICL1 and MLS1 synthetic genes integrated in the genome.

Figure 13:
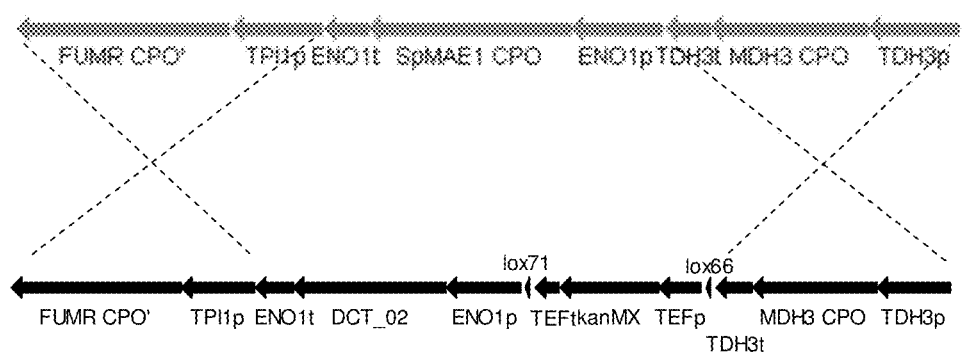

FIG. 13 Depiction of the 7.7 kB fragment from pSUC174 containing the synthetic MDH3, DCT_02 and FUMR synthetic genes and the KanMX selection marker, flanked by lox66 and lox71 sites. After replacement of the SpMAE1 synthetic gene by the DCT_02 synthetic gene, the KanMX marker was removed by Cre-recombinase (Güldener U, Heck S, Fielder T, Beinhauer J, Hegemann J H., Nucleic Acids Res. 1996 Jul. 1; 24(13):2519-2524).

EXAMPLE 1

Construction of strains SUC-662 and 632

1.1 Construction of integration vectors

Plasmid pSUC044, was constructed as follows: Plasmid pPWT006 (FIG. 1), consisting of a YGR059w (SPR3) or SIT2-locus (Gottlin-Ninfa and Kaback (1986) Molecular and Cell Biology vol. 6, no. 6, 2185-2197) and the markers allowing for selection of transformants on the antibiotic G418 and the ability to grow on acetamide, was digested with the restriction enzymes MluI and ApaI. The kanMX-marker, conferring resistance to G418, was isolated from p427TEF (Dualsystems Biotech) and a fragment containing the amdS-marker has been described in literature (Swinkels, B. W., Noordermeer, A. C. M. and Renniers, A. C. H. M (1995). Yeast Volume 11, Issue 1995A, page S579; and U.S. Pat. No. 6,051,431).

The genes encoding fumarate reductase (FRDg) from Trypanosoma brucei, as disclosed in patent application WO2009/065778, and phosphoenolpyruvate carboxykinase (PCKa) from Actinobacillus succinogenes, as disclosed in patent application WO2009/065780, were synthesized by Sloning (Puchheim, Germany). Specific promoter;gene;terminator sequences, including appropriate restriction sites, were synthesized. The gene sequences were codon pair optimized for expression in S. cerevisiae as disclosed in patent application WO2008/000632. The synthetic genes are under control of (or operable linked to) strong promoters from S. cerevisiae, i.e. the TDH3-promoter controlling the expression of the FRDg-gene, and the TPI1-promoter controlling the PCKa-gene. Proper termination is controlled by terminator sequences from S. cerevisiae, i.e. the TDH3-terminator controlling the FRDg-gene and the PMA1-terminator, present on plasmid pPWT006, controlling the PCKa-gene. The TDH3-promoter;FRDg-gene;TDH3-terminator sequence was surrounded by the unique restriction enzymes sites MluI and ApaI. The TPI1-promoter, PCKa-gene sequence was surrounded by the unique restriction enzymes sites ApaI and Bs/WI. Cloning of the FRDg synthetic construct into pPWT006 digested with MluI and ApaI resulted in the intermediate plasmid pPWT006-FRDg. Cloning of the PCKa synthetic construct into pPWT006-FRDg digested with ApaI and BsiWI resulted in plasmid pSUC044 (SEQ ID NO: 1, FIG. 2).

Plasmid pSUC047, was constructed as follows: Plasmid pPWT007 (FIG. 3), consisting of a YEL023c or S/T4-locus (Gottlin-Ninfa and Kaback (1986) Molecular and Cell Biology vol. 6, no. 6, 2185-2197) and the markers allowing for selection of transformants on the antibiotic G418 and the ability to grow on acetamide, was digested with the restriction enzymes MluI and ApaI.

The genes encoding malate dehydrogenase (MDH3) from S. cerevisiae, as disclosed in patent application WO2009/065778, fumarase (FUMR) from Rhizopus oryzae, as disclosed in patent application WO2009/065779, and malic acid transporter (SpMAE1) from Schizosaccharomyces pombe, as disclosed in patent application WO2009/065778, were synthesized by Sloning (Puchheim, Germany). Specific promoter;gene;terminator sequences, including appropriate restriction sites were synthesized. The gene sequences were codon pair optimized for expression in *Saccharomyces cerevisiae* as disclosed in patent application WO2008/000632. The synthetic genes were under control of (or operable linked to) strong promoters from *S. cerevisiae*, i.e. the TDH3-promoter controlling the expression of the MDH3-gene, the TPI1-promoter controlling the FUMR-gene and the ENO1-promoter controlling the SpMAE1 gene. Proper termination was controlled by terminator sequences from *S. cerevisiae*, i.e. the TDH3-terminator controlling the MDH3-gene, the PMA1-terminator, present on plasmid pPWT006, controlling the PCKa-gene, and the ENO1-terminator controlling the SpMAE1-gene. The TDH3-promoter;MDH3-gene;TDH3-terminator sequence was surrounded by the unique restriction enzymes sites MluI and ApaI. The TPI1-promoter, FUMR-gene sequence was surrounded by the unique restriction enzymes sites ApaI, AscI and NotI at the 5' end and Bs/WI at the 3' end. The ENO1-promoter;SpMAE1-gene;ENO1-terminator
sequence was surrounded by the unique restriction enzymes sites MluI and ApaI. Cloning of the MDH3 synthetic construct into pPWT007 digested with MluI and ApaI resulted in intermediate plasmid pPWT007-MDH3. Cloning of the FUMR synthetic construct into pPWT007-MDH3 digested with ApaI and BsiWI resulted in plasmid pSUC046. Cloning of the SpMAE1 synthetic construct into pSUC046 digested with AscI and NotI resulted in plasmid pSUC047 (SEQ ID NO: 2, FIG. 4).

Plasmid pBOL034 (FIG. 5), consisting of a 1000 bp YOL086C (ADH1) promoter sequence (1000 bp directly upstream of start codon of YOL086C), a 500 bp YOL086C (ADH1) terminator sequence (500 bp directly downstream of stop codon) and inserted gene sequences, was used as host vector to construct pSUC091 (FIG. 6). A URA3-promoter; URA3-gene;URA3-terminator PCR fragment was obtained using plasmid pRS416 as template (Sikorski R S, Hieter P. 1989 May; 122(1):19-27). The primers contained appropriate restriction enzymes sites, MluI for the forward and BsrGI for the reverse primer, for further subcloning of the PCR fragment. The gene sequence encoding pyruvate carboxylase (PYC2) from *S. cerevisiae*, as disclosed in patent application WO2009/065780, was synthesized by Geneart (Regensburg, Germany). A specific promoter;gene;terminator sequence, including appropriate restriction sites was synthesized. The gene sequence was codon pair optimized for expression in *S. cerevisiae* as disclosed in patent application WO2008/000632. The synthetic gene was under control of (or operably linked to) a strong promoter from *S. cerevisiae*, i.e. the PGK1-promoter controlling the expression of the PYC2-gene. Proper termination was controlled by a terminator sequence from *S. cerevisiae*, i.e. the PGK1-terminator controlling the PYC2-gene. The PGK1-promoter; PYC2-gene;PGK1-terminator sequence was surrounded by the unique restriction enzymes sites StuI and MluI. After restriction of pBOL034 with BsrGI, PsiI and SnaBI, restriction of the URA3 PCR fragment with MluI and BsrGI and the PGK1-promoter, PYC2-gene, PGK1-terminator sequence with StuI and MluI, the three DNA fragments were ligated by a 3-point ligation to yield plasmid pSUC091 (SEQ ID NO: 3, FIG. 6).

Plasmid pSUC111 used for integration of isocitrate lyase and malate synthase synthetic genes, was constructed as follows. Plasmid p417-CYC (yeast-*E. coli* shuttle vector containing a KanMX marker functional in yeast, Dualsystems Biotech AG, Schlieren, Switzerland) was restricted with XbaI/EcoRV, in which a INT5'-repeat-LoxP-Amds (partial) synthetic construct restricted with XbaI/SwaI was ligated, resulting in plasmid pBOL267 (FIG. 7). The synthetic construct was synthesized by GeneArt (Regensburg, Germany).

The genes encoding isocitrate lyase (KIICL1) from *Kluyveromyces lactis* and malate synthase (MLS1) from *S. cerevisiae* as disclosed in patent application WO2009/101180, were synthesized by Sloning (Puchheim, Germany). Specific promoter;gene;terminator sequences, including appropriate restriction sites were synthesized. The gene sequences were codon pair optimized for expression in *Saccharomyces cerevisiae* as disclosed in patent application WO2008/000632. The synthetic genes were under control of (or operable linked to) strong promoters from *S. cerevisiae*, i.e. the TDH1-promoter controlling the expression of the KIICL1-gene, and the TDH3-promoter controlling expression of the MLS1-gene. Proper termination was controlled by a terminator sequence from *S. cerevisiae*, i.e. the TDH1-terminator controlling the KIICL1-gene and the TDH3-terminator controlling expression of the MLS1-gene.

The KIICL1 and MLS1 synthetic gene constructs were ligated into the plasmid pBOL267 resulting in plasmid pSUC111 (SEQ ID NO: 4, FIG. 8).

Plasmid pBOL268 (SEQ ID NO: 5, FIG. 9) is also required to integrate the KIICL1 and MLS1 synthetic gene constructs at the INT locus. Plasmids pSUC111 and pBOL268 contain a partial amdS sequence that will become functional after transformation with the remainder part of a partial amdS sequence, as explained in section 1.2 and in FIG. 11. To obtain a functional amdS gene, and to allow selection for growth on acetamide as sole nitrogen source, the restricted plasmid pSUC111 has to be transformed with restricted plasmid pBOL268. Plasmid pBOL268 was constructed as follows. Plasmid p417-CYC (yeast-*E. coli* shuttle vector containing a KanMX marker functional in yeast, Dualsystems Biotech AG, Schlieren, Switzerland) was restricted with SaII/SmaI, in which an Amds (partial)-LoxP-repeat-INT3' synthetic construct restricted with SaII/SwaI was ligated, resulting in plasmid pBOL268 (FIG. 9). The synthetic construct was synthesized by GeneArt (Regensburg, Germany).

To replace the SpMAE1 synthetic gene integrated in genomic DNA by the DCT_02 sequence, plasmid pSUC174 was created. Sequence DCT_02 encodes a putative dicarboxylic acid transporter (SEQ ID NO: 6) with 30.2% identity as compared to the SpMAE1 sequence as determined using the Needle program (Needleman and Wunsch algorithm, Needleman, S. B. and Wunsch, C. D. (1970) J. Mol. Biol. 48, 443-453). The gene sequence was codon pair optimized for expression in *S. cerevisiae* as disclosed in patent application WO2008/000632. In the synthetic DCT_02 gene sequence the stop codon was modified to TAAG. The synthetic DCT_02 gene was under control of (or operable linked to) a strong promoter from *S. cerevisiae*, i.e. the ENO1-promoter (600 bp upstream of the start codon of the ENO1 gene). In the ENO1 promoter, T at position 596 (−5) was changed to A in order to obtain a better Kozak sequence. Proper termination was controlled by a terminator sequence from *S. cerevisiae*, i.e. the ENO1-terminator (300 bp downstream of the stop codon of the ENO1 gene). The ENO1-promoter;DCT-02;ENO1-terminator sequences was surrounded by unique restriction enzymes sites. The resulting sequence SEQ ID NO: 7 was synthesized by Geneart (Regensburg, Germany).

Plasmid pSUC174 was created as follows: The ENO1-promoter;SpMAE1;ENO1-terminator was removed from plasmid pSUC047. A KanMX cassette flanked by lox66 and lox71 sites (Lambert J M, Bongers R S, Kleerebezem M., Appl. Environ Microbiol. 2007 Feb.; 73(4):1126-35.) was introduced into the intermediate plasmid. Subsequently, the DCT_02 synthetic gene (SEQ ID NO: 7) was ligated into this intermediate plasmid, resulting in plasmid pSUC174 (SEQ ID NO: 8, FIG. 10) Plasmid pSUC176 was created as follows: The ENO1-promoter;SpMAE1;ENO1-terminator was removed from plasmid pSUC047. Subsequently, a Tag (repeat)-loxP-amdS-loxP-Tag (repeat) cassette was ligated into the vector backbone, resulting in intermediate vector pSUC175. The Tag sequence consists of the nucleotides CGTATATGTCATGCTCGTGACAAAGAGCG-TAAGATGGCGAAC, which would encode a protein with the sequence RICHARDKERKMAN. The DCT_02 synthetic gene sequence was ligated into vector pSUC175, resulting in replacement plasmid pSUC176 (FIG. 11).

1.2 Yeast transformation

*Saccharomyces cerevisiae* strain CEN.PK113-5D (MATa ura3,52 HIS3 LEU2 TRP1 MAL2-8 SUC2) was transformed with plasmid pSUC047 (FIG. 4), which was previously linearized with SfiI (New England Biolabs), according to the instructions of the supplier. A synthetic SfiI-site was designed in the sequence of the SIT4-gene present on plasmid pPWT007 (designated SIT4A, see FIG. 3). Transformation mixtures were plated on YPD-agar (per liter: 10 g of yeast extract, 20 g peptone, 20 g dextrose, 20 g of agar) containing 100 µg G418 (Sigma Aldrich) per ml. After two to four days, colonies appeared on the plates, whereas the negative control (i.e. no addition of DNA in the transformation experiment) resulted in blank YPD/G418-plates. Alternatively, positive transformants were selected on agar plates containing acetamide, which can be used as a sole nitrogen source due to the presence of the acetamidase (amdS) marker after integration of the DNA construct. For this purpose, transformation mixtures were plated on agar acetamide agar plates (per liter: 20 g of agar, 20 g potassium dihydrogen phosphate, 0.5 g of magnesiumsulfat-heptahydrat, 70 ml of 32% galactose, 1 ml of 50% dextrose, 12.5 ml of 400 mM acetamide (Sigma), 1 ml vitamins and 1 ml trace elements (compositions of vitamins and trace elements are described in literature (Verduyn C, Postma E, Scheffers W A, Van Dijken J P. Yeast, 1992 July; 8(7):501-517). After two to four days, colonies appeared on the plates, whereas the negative control (i.e. no addition of DNA in the transformation experiment) resulted in blank acetamide agar-plates. The integration of plasmid pSUC047 was directed to the SIT4-locus. Correct transformants with integration of the a single copy of the MDH3, FUMR and SpMAE1 genes at the SIT4-locus were characterized using PCR techniques. A strain in which a single copy of the to be inserted synthetic genes was integrated in the SIT4-locus, designated CEN.PK113-5D-pSUC047 was used for marker rescue (see below). The resulting marker-free strain was designated SUC-270 (MATa ura3,52 HIS3 LEU2 TRP1 sit4::TDH3p-MDH3-TDH3t;ENO1p-SpMAE1-ENO1t;TPI1p-FUMR-PMA1t MAL2-8 SUC2).

Strain SUC-270 was transformed with plasmid pSUC044 (FIG. 2), which was previously linearized with SfiI (New England Biolabs), according to the instructions of the supplier. A synthetic SfiI-site was designed in the sequence of the SIT2-gene on plasmid pPWT006 (designated SIT2A, see FIG. 1). Transformation mixtures were plated as described above. After two to four days, colonies appeared on the plates, whereas the negative control (i.e. no addition of DNA in the transformation experiment) resulted in blank YPD/G418-plates. The integration of plasmid pSUC044 was directed to the SIT2-locus. Correct transformants with single copy integration of the PCKa and FRDg genes at the SIT2 locus were characterized using PCR techniques. The resulting single copy integration strain was designated SUC-304, which was subsequently used for marker-rescue (see below), resulting in marker-free strain SUC-347 (MATa ura3,52 HIS3 LEU2 TRP 1 sit2::TPI1p-PCKa-PMA1t;TDH3p-FRDg-TDH3t sit4::TDH3p-MDH3-TDH3t;ENO1p-SpMAE1-ENO1t;TPI1p-FUMR-PMA1t MAL2-8 SUC2). Strain SUC-347 was further analyzed by Southern blot analysis, which confirmed correct integration of the introduced synthetic genes and out-recombination of the marker genes.

In order to be able to transform the yeast strains CEN.PK113-5D-pSUC047 and SUC-304 with other constructs, using the same selection markers, it was necessary to remove the selectable markers. The design of plasmid pSUC044 and pSUC047 was such, that upon integration of pSUC044 and pSUC047 in the chromosome, homologous sequences were in close proximity of each other. This design allowed the selectable markers to be lost by spontaneous intramolecular recombination of these homologous regions.

Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strains CEN.PK113-5D-pSUC047 and SUC-304 were cultured in YPD-medium (per liter: 10 g of yeast extract, 20 g peptone, 20 g dextrose), starting from a single colony isolate. 25 µl of an overnight culture was used to inoculate fresh YPD medium. After at least five of such serial transfers, the optical density of the culture was determined and cells were diluted to a concentration of approximately 5000 per ml. 100 µl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Cells identical to cells of strains CEN.PK113-5D-pSUC047 and SUC-304, i.e. without intracellular recombination, still contained the amdS-gene. To those cells, fluoro-acetamide is toxic. These cells will not be able to grow and will not form colonies on a medium containing fluoro-acetamide. However, if intramolecular recombination has occurred, CEN.PK113-5D-pSUC047 and SUC-304 variants that have lost the selectable markers will be able to grow on the fluoro-acetamide medium, since they are unable to convert fluoro-acetamide into growth inhibiting compounds. Those cells will form colonies on this agar medium. The obtained fluoro-acetamide resistant colonies of CEN.PK113-5D-pSUC047 and SUC-304 were subjected to PCR analysis to confirm that out-recombination of the selectable markers had taken place as intended. As a result, the cassette with the genes MDH3, FUMR, SpMAE1, PCKa and FRDg under control of the strong yeast promoters had been integrated in the SIT4-locus of the genome of the host strain.

Strain SUC-347 was transformed with a 6.4 kB fragment of plasmid pSUC091, which was previously linearized with the restriction enzymes SwaI, SalI and ClaI (FIG. 6). Transformation mixtures were plated on Yeast Nitrogen Base (YNB) w/o AA (Difco)+2% glucose. Correct transformants were initially selected for uracil prototrophy, because the parent strain had an auxotrophy for uracil (ura3,52), which was complemented by a functional copy of the URA3 gene. The transformants were further analyzed by PCR to confirm correct targeting of the URA3 PCR product and PYC2 synthetic construct into the adh1 locus. The resulting strain was designated SUC-401 (MATa ura3,52 H1S3 LEU2 TRP 1 sit2::TPI1p-PCKa-PMA1t;TDH3p-FRDg-TDH3t sit4:: TDH3p-MDH3-TDH3t;ENO1p-SpMAE1-ENO1 t;TPI1p-FUMR-PMA1 t adh1::PGK1p-PYC2-PGK1t;URA3p-URA3-URA3t MAL2-8 SUC2).

KlICL1 and MLS1 were transformed into strain SUC-401 as follows: Plasmid pSUC111 (FIG. 8) was restricted using the enzymes AsiSI and SbfI. A 9.06 kB fragment containing the KlICL1 and MLS1 synthetic genes, the 5' INT flank (see below), a loxP site and a partial amdS sequence was excised from an agarose gel.

Plasmid pBOL268 (FIG. 9) was restricted using the enzymes SgrAI and AvrII. A 2.4 kB fragment containing the 3' INT1 flank (see below), a loxP site and a partial amdS sequence was excised from an agarose gel. Both fragments were transformed into strain SUC-401. Transformants were selected on selective plates containing acetamide as the sole nitrogen source (Yeast Carbon Base (Difco) containing galactose as C-source.

The integration of the KlICL1 and MLS1 synthetic genes was accomplished by transforming two constructs that are combined in vivo by recombination. Plasmid pSUC111 contains a partial amdS sequence that will become functional after transformation with the remainder part of a partial amdS sequence, as explained below and in FIG. 11. To obtain a functional amdS gene, and to allow selection for growth on acetamide as sole nitrogen source, the restricted plasmid pSUC111 has to be transformed with restricted plasmid pBOL268. In vivo recombination of the 5' and 3' parts of amdS will fuse the two fragments and results in a functional amdS gene. The functional amdS gene will consist of the PMA 1-promoter from *S. cerevisiae*, the amdS gene from *Aspergillus nidulans* and the transcription terminator of the LAC4 gene of *K. lactis*. This cassette confers the transformed yeast cell the ability to utilize acetamide as a sole nitrogen source. Recombination of the LF (Left Flank) and RF (Right Flank) flanking regions with the genomic homologous sequences leads to integration of the construct in the genome. Positive transformants were re-streaked and checked by PCR for the presence of the KlICL1 and MLS1 synthetic genes. The resulting strain was designated SUC-443 (MATa ura3,52 HIS3 LEU2 TRP1 sit2::TPI1p-PCKa-PMA 1 t;TDH3p-FRDg-TDH3t sit4::TDH3p-MDH3-TDH3t;ENO1p-SpMAE1-ENO1t;TPI1p-FUMR-PMA1t adh1::PGK1p-PYC2-PGK1t;URA3p-URA3-URA3t MAL2-8 SUC2 int::TDH1p-ICL1-TDH1t; TDH3p-MLS1-TDH3t; loxP-Amds-loxP). The isocitrate lyase and malate synthase synthetic genes were integrated into yeast genomic DNA between the open reading frames NTR1 (YOR071c) and GYP1 (YOR070c) located at 659 bp downstream of the stop codon of NTR1 and 997 bp upstream of the start codon of GYP1 on chromosome XV. This integration is named INT.

The amdS marker flanked by loxP sites was removed from strain SUC-443 by transformation of Cre-recombinase (Güldener U, Heck S, Fielder T, Beinhauer J, Hegemann J H., Nucleic Acids Res. 1996 Jul. 1; 24(13):2519-2524) using plasmid pSH65 containing a phleomycin resistance marker. Removal of the amdS marker was confirmed by plate testing. Fluoro-acetamide is toxic to cells containing the amdS gene, which converts fluoro-acetamide into a toxic compound. Transformants that have lost the amdS marker will be able to grow on the fluoro-acetamide agar plates, since they are unable to convert fluoro-acetamide into growth inhibiting compounds. Those cells will form colonies on this agar plates. Subsequently plasmid pSH65 was cured from the cells by growth on non-selective medium (YEP 2% galactose), resulting in strain SUC-489. One loxP site has remained in genomic DNA of strain SUC-489.

In order to replace the SpMAE1 dicarboxylic acid transporter gene by the DCT_02 dicarboxylic acid transporter gene, plasmid pSUC174 (FIG. 10) was constructed as described under Example 1.1. pSUC174 contains at the 5' end the FUMR synthetic gene, the DCT_02 transporter and a KanMX selection marker flanked by lox66/lox71 sites (Lambert J M, Bongers R S, Kleerebezem M., Appl Environ Microbiol. 2007 Feb.; 73(4):1126-35), and at the 3' end the MDH3 synthetic gene. Plasmid pSUC174 was restricted with Bsu36I and FseI and the resulting 7.7 kB fragment was purified and transformed into strain SUC-489. By homologous recombination over the FUMR synthetic gene and the MDH3 synthetic gene present in the genomic DNA of strain SUC-489, the linearized pSUC174 construct replaced the SpMAE1 transporter by DCT_02 (FIG. 13). Correct transformants were initially selected for their resistance against G418, due to integration of the KanMX resistance marker. Next, a diagnostic PCR on intermediate strain SUC-661 was performed to confirm replacement of the SpMAE1 synthetic gene by the DCT_02 synthetic gene. The KanMX marker flanked by lox66 and lox71 sites was removed from strain SUC-661 by transformation of Cre-recombinase (Güldener U, Heck S, Fielder T, Beinhauer J, Hegemann J H., Nucleic Acids Res. 1996 Jul. 1; 24(13):2519-2524) using plasmid pSH65 containing a phleomycin resistance marker. Subsequently plasmid pSH65 was cured from the cells by growth on non-selective medium (YEP 2% galactose), remaining one lox72 in the genomic DNA. The resulting strain was designated SUC-662 (MATa ura3,52 HIS3 LEU2 TRP1 sit2::TPI1p-PCKa-PMA1t;TDH3p-FRDg-TDH3t sit4:: TDH3p-MDH3-TDH3t;ENO1p-DCT_02-ENO1 t;TPI1p-FUMR-PMA1 t;lox72 adh1::PGK1p-PYC2-PGK1t; URA3p-URA3-URA3t MAL2-8 SUC2 int::TDH1p-ICL1-TDH1t; TDH3p-MLS1-TDH3t).

Next, the second copy of the SpMAE1 gene present in the genomic DNA of SUC-489 was replaced by transformation of a 9.5 kB fragment from pSUC176 (FIG. 11—constructed as described under Example 1.1). This plasmid contains at the 5' end the FUMR synthetic gene, the DCT_02 transporter and a amdS selection marker flanked by loxP sites, and at the 3' end the MDH3 synthetic gene. Plasmid pSUC176 was restricted with Bsu36I and FseI and the resulting 9.5 kB fragment was purified and transformed into strain SUC-662. The fragment from pSUC176 can either replace the remaining SpMAE1 gene or the introduced DCT_02 gene. Positive transformants were selected for the ability to grow on acetamide as sole nitrogen source (replacement of the $2^{nd}$ copy of SpMAE1) and the ability to grow on plates containing G418 as selection marker (replacement of the $1^{st}$ SpMAE1 copy). Only those colonies that are able to grow on these two plates have a replacement of the two copies of SpMAE1. In case the $2^{nd}$ replacement construct (amdS marker) replaces the $1^{st}$ replacement construct (KanMX marker), transformants are able to grow on plates containing acetamide as sole nitrogen source, but are not able to grow on plates containing G418. Transformants that contained only DCT_02 genes and no SpMAE1 genes were confirmed by PCR. This resulted in strain SUC-571 which still contains a KanMX and amdS selection marker. To remove the KanMX marker flanked by lox66 and lox71 sites and the amdS marker, flanked by loxP sites, strain SUC-571 was transformed with pSH65 for expression of Cre-recombinase (pSH65 contains a phleomycin resistance marker, Güldener, 1996). Removal of the KanMX and amdS markers was confirmed by plate testing, resulting in strain SUC-592. After removal of the markers, one lox72 site and one loxP site remain present in chromosome (likely in chromosome V, on which the SIT4 integration site is located). Subsequently plasmid pSH65 was cured from genomic DNA of strain SUC-592 by growing on non-selective medium, resulting in strain SUC-632.

EXAMPLE 2

Succinic Acid Production by Yeast in the Presence of Gas Flow of Different Compositions and Different Pressures Yeast strain SUC-401 constructed as described above, was cultivated in shake-flask (150 ml) for 3 days at 30° C. and 110 rpm. The medium was based on Verduyn medium (Verduyn C, Postma E, Scheffers W A, Van Dijken J P. Yeast, 1992 July; 8(7):501-517), but modifications in carbon and nitrogen source were made as described herein below.

TABLE 1

Preculture medium composition

| Raw material | | Concentration (g/l) |
|---|---|---|
| Galactose | $C_6H_{12}O_6 \cdot H_2O$ | 20.0 |
| Urea | $(NH_2)_2CO$ | 2.3 |
| Potassium dihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |

| Component | Formula | Concentration (g/kg) |
|---|---|---|
| EDTA | $C_{10}H_{14}N_2Na_2O_8 \cdot 2H_2O$ | 15.00 |
| Zincsulphate•7H$_2$O | $ZnSO_4 \cdot 7H_2O$ | 4.50 |
| Manganesechloride•2H$_2$O | $MnCl_2 \cdot 2H_2O$ | 0.84 |
| Cobalt (II) chloride•6H$_2$O | $CoCl_2 \cdot 6H_2O$ | 0.30 |
| Cupper (II) sulphate•5H$_2$O | $CuSO_4 \cdot 5H_2O$ | 0.30 |
| Sodium molybdenum•2H$_2$O | $Na_2MoO_4 \cdot 2H_2O$ | 0.40 |
| Calciumchloride•2H$_2$O | $CaCl_2 \cdot 2H_2O$ | 4.50 |
| Ironsulphate•7H$_2$O | $FeSO_4 \cdot 7H_2O$ | 3.00 |
| Boric acid | $H_3BO_3$ | 1.00 |
| Potassium iodide | KI | 0.10 |
| Biotin (D-) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

[a]Trace elements solution
[b]Vitamin solution

Subsequently, the content of the shake-flask was transferred to a seed fermenter (startvolume 10 L), which contained the following medium:

TABLE 2

Medium composition seed fermenter

| Raw material | | Concentration (g/l) |
|---|---|---|
| Ammonium sulphate | $(NH_4)_2SO_4$ | 1.0 |
| Potassium dihydrogen phosphate | $KH_2PO_4$ | 10 |
| Magnesium sulphate | $MgSO_4 \cdot 7H_2O$ | 5.0 |

TABLE 2-continued

Medium composition seed fermenter

| Raw material | Concentration (g/l) |
|---|---|
| Trace element solution | 8.0 |
| Vitamin solution | 8.0 |

The pH was controlled at 5.0 by addition of 28% ammonia. Temperature was controlled at 30° C. pO$_2$ was controlled at 20% by adjusting the stirrer speed. Glucose concentration was kept limited by controlled feed to the fermenter (exponent of 0.1 was applied).

After 70 hours of fermentation 1.5 L of seed fermenter was transferred to a production fermenter (startvolume 15 L), which contained the following medium:

TABLE 3

Medium composition production fermenter

| Raw material | | Concentration (g/l) |
|---|---|---|
| Urea | $(NH_2)_2CO$ | 1.0 |
| Potassium dihydrogen phosphate | $KH_2PO_4$ | 3.0 |
| Magnesium sulphate | $MgSO_4 \cdot 7H_2O$ | 0.5 |
| Trace element solution | | 1 |
| Chalk | $CaCO_3$ | 4 |
| Biotin | | 0.001 |

No pH control was applied during the whole fermentation. The added CaCO$_3$ caused initial buffering of the pH at around 5-5.5. Subsequently, the pH dropped by natural acidification towards a pH of 3 at the end of fermentation. Temperature was controlled at 30° C. Glucose concentration was kept limited by controlled feed to the fermenter (0-24 h: 3.2 g/L/h; >24 h: 2.1 g/L/h or adapt if needed).

Two different production fermentations as described above were carried out in the presence of different gas flows and compositions:

During fermentation 1) 0.33 vvm of 100% air was sparged to the fermenter (startvolume 15 L);

During fermentation 2) 0.33 vvm of total gas (50% CO$_2$, 50% air) was sparged to the fermenter (startvolume 15 L).

In addition, two other different fermentations 3) and 4) with strain SUC-662 are carried out at a 200 cubic metre scale (startvolume) in a similar medium as described in Table 3, using a seed fermentation of 20 cubic metre, which is prepared in a medium with the composition of Table 2. To obtain seed for the fermentation of 20 cubic metre, one 2 cubic metre fermentation from a shake flask fermentation is carried out.

During fermentation 3), 0.039 vvm of air is sparged to the fermenter (startvolume 200 m$^3$);

During fermentation 4) 0.027 vvm of oxygen enriched air (10% O$_2$, 90% air) is sparged to the fermenter (startvolume 200 m$^3$).

During fermentation 3) a headspace pressure 1.5 bar absolute is assumed; during fermentation 4) a headspace pressure of 2.5 bar absolute is assumed.

During all four fermentations, the pO$_2$ was/is controlled at 5% by adjusting the stirrer speed.

Results

It was calculated that the succinic acid yield ($Y_{ps}$) under an air atmosphere (inlet gas is air) with increased pressure (3.0 bar absolute average pressure in fermenter) and under an increased oxygen atmosphere (oxygen enriched air) combined with increased pressure (2.0 bar absolute average pressure in fermenter) is almost twice as high as compared to the yield under 100% air, and similar to the yield under 50 v/v % $CO_2$ conditions (Fermentation 2, Table 4).

Fermentation 1) and 2) are based on experimental results, fermentation 3) and 4) are based on theoretical calculations.

The results show that a sufficient partial carbon dioxide pressure ($pCO_2$) is needed for a proper yield of succinic acid ($Y_{ps}$). The $pCO_2$ is calculated based on the converted oxygen fraction (taken up by the cells and converted to $CO_2$ in equimolar amounts) in the in-going gas multiplied by the local pressure present. The oxygen uptake by the cells is assumed to be in the same range as the oxygen transfer to the fermentation broth. The oxygen transfer is calculated based on the geometry of the fermenter (height over diameter ratio) and the stirrer, the gas composition and flow of the in-going gas, and the power input of the stirrer.

TABLE 4

Effect of gas inflow composition on succinic acid production performance ($Y_{ps}$), measured after 42 h of fermentation.

| Fermentation Condition | % $O_2$ in in-gas | Average pressure in fermenter (bar absolute) | $pCO_2$ (bar) | $Y_{ps}$ (g/g) |
|---|---|---|---|---|
| Experimental | | | | |
| 1 | 100% air | 21 | 1 | 0.04 | 0.24 |
| 2 | 50% air, 50% $CO_2$ | 10.5 | 1 | 0.50 | 0.41 |
| Theoretically calculated | | | | |
| 3 | 100% air | 21 | 3.0 | 0.47 | 0.4 |
| 4 | 90% air, 10% $O_2$ | 28 | 2.0 | 0.46 | 0.4 |

EXAMPLE 3

Succinic Acid Production by Yeast in the Presence of Gas Flow of Different Compositions and Different Pressures Yeast strain SUC-632 constructed as described above, was cultivated in a stainless steel vessel (6 kg) for 4 days at 30° C. (placed in waterbath). For aeration and proper mixing 18 NL/min of air was supplied to the vessel. The medium was based on Verduyn medium (Verduyn C, Postma E, Scheffers W A, Van Dijken J P. Yeast, 1992 July; 8(7):501-517), but modifications in carbon and nitrogen source were made as described herein below.

TABLE 5

Preculture medium composition

| Raw material | | Concentration (g/l) |
|---|---|---|
| Galactose | $C_6H_{12}O_6 \cdot H_2O$ | 20.0 |
| Urea | $(NH_2)_2CO$ | 2.3 |
| Potassium dihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |

TABLE 5-continued

Preculture medium composition

| Component | Formula | Concentration (g/kg) |
|---|---|---|
| EDTA | $C_{10}H_{14}N_2Na_2O_8 \cdot 2H_2O$ | 15.00 |
| Zincsulphate•$7H_2O$ | $ZnSO_4 \cdot 7H_2O$ | 4.50 |
| Manganesechloride•$2H_2O$ | $MnCl_2 \cdot 2H_2O$ | 0.84 |
| Cobalt (II) chloride•$6H_2O$ | $CoCl_2 \cdot 6H_2O$ | 0.30 |
| Cupper (II) sulphate•$5H_2O$ | $CuSO_4 \cdot 5H_2O$ | 0.30 |
| Sodium molybdenum•$2H_2O$ | $Na_2MoO_4 \cdot 2H_2O$ | 0.40 |
| Calciumchloride•$2H_2O$ | $CaCl_2 \cdot 2H_2O$ | 4.50 |
| Ironsulphate•$7H_2O$ | $FeSO_4 \cdot 7H_2O$ | 3.00 |
| Boric acid | $H_3BO_3$ | 1.00 |
| Potassium iodide | KI | 0.10 |
| Biotin (D-) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_2N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

[a]Trace elements solution
[b]Vitamin solution

Subsequently, the content of the stainless steel vessel was transferred to a seed fermenter (startvolume 4,0 $m^3$), which contained the following medium:

TABLE 6

Medium composition seed fermenter

| Raw material | | Concentration (g/l) |
|---|---|---|
| Ammonium sulphate | $(NH_4)_2SO_4$ | 1.0 |
| Potassium dihydrogen phosphate | $KH_2PO_4$ | 10 |
| Magnesium sulphate | $MgSO_4 \cdot 7H_2O$ | 5.0 |
| Trace element solution | | 8.0 |
| Vitamin solution | | 8.0 |

The pH was controlled at 5.0 by addition of 20% ammonia. Temperature was controlled at 30° C. $pO_2$ was controlled at 20% by adjusting the stirrer speed. Glucose concentration was kept limited by controlled feed to the fermenter (exponent of 0.1 was applied).

After 70 hours of fermentation 4,7 $m^3$ of seed fermenter was transferred to a production fermenter (startvolume 55 $m^3$), which contained the following medium:

TABLE 7

Medium composition production fermenter

| Raw material | | Concentration (g/l) |
|---|---|---|
| Urea | $(NH_2)_2CO$ | 1.0 |
| Potassium dihydrogen phosphate | $KH_2PO_4$ | 3.0 |
| Magnesium sulphate | $MgSO_4 \cdot 7H_2O$ | 0.5 |
| Trace element solution | | 1 |
| Chalk | $CaCO_3$ | 4 |
| Biotin | | 0.001 |
| Iron-sulphate | $FeSO_4 \cdot 7H_2O$ | 0.006 |

No pH control was applied during the whole fermentation. The added $CaCO_3$ caused initial buffering of the pH at around 5-5.5. Subsequently, the pH dropped by natural acidification towards a pH of 3 at the end of fermentation. Temperature was controlled at 30° C. Glucose concentration was kept limited by controlled feed to the fermenter (0-24 h: 3.0 g/L/h; >24 h: 2.1 g/L/h or adapt if needed).

Three different production fermentations as described above were carried out in the presence of different gas flows and compositions:

During fermentation 1) 0.035 vvm of total gas (30% $O_2$ concentration) was sparged to the fermenter, 0.4 bar extra overpressure (1.4 bar absolute) was applied on the headspace;

During fermentation 2) 0.018 vvm of total gas (41% $O_2$ concentration) was sparged to the fermenter, 0.4 bar extra overpressure (1.4 bar absolute) was applied on the headspace;

During fermentation 3) 0.031 vvm of total gas (29% $O_2$ concentration) was sparged to the fermenter, 0.9 bar extra overpressure (1.9 bar absolute) was applied on the headspace.

During all four fermentations, the $pO_2$ was/is controlled at 5% by adjusting the stirrer speed.

Results

The results show that a sufficient partial carbon dioxide pressure ($pCO_2$) is needed for a proper yield of succinic acid ($Y_{ps}$). The $pCO_2$ is calculated based on the converted oxygen fraction (taken up by the cells and converted to $CO_2$ in equimolar amounts) in the in-going gas multiplied by the local pressure present.

A sufficient partial carbon dioxide pressure can be realized by increasing the oxygen concentration in the inflowing gas and/or by increasing the pressure.

TABLE 8

Effect of gas inflow composition on succinic acid production performance ($Y_{ps}$), measured after 70 h of fermentation.

| Fermentation | Total gasflow (vvm) | % $O_2$ in in-gas | Average pressure in fermenter (bar absolute) | $pCO_2$ (bar) | $Y_{ps}$ (g/g) |
|---|---|---|---|---|---|
| 1 | 0.035 | 30 | 1.7 | 0.4 | 0.43 |
| 2 | 0.018 | 41 | 1.7 | 0.63 | 0.52 |
| 3 | 0.031 | 29 | 2.2 | 0.52 | 0.52 |

The invention claimed is:

1. A process for producing succinic acid comprising
fermenting a yeast cell in a vessel comprising a suitable fermentation medium,
adding a gas which comprises 21% to about 35 v/v % of oxygen and less than about 0.1 v/v % of carbon dioxide to the fermentation medium,
maintaining an average partial carbon dioxide pressure of at least about 0.35 bar in the fermentation medium, and producing the succinic acid,
wherein the gas is oxygen enriched air.

2. The process according to claim 1, wherein the average partial carbon dioxide pressure is from about 0.35 to about 1.0 bar.

3. The process according to claim 2, wherein the average partial carbon dioxide pressure is from about 0.35 to about 0.8 bar.

4. The process according to claim 1, wherein the vessel comprises a headspace pressure of from about 1.05 to about 5 bar absolute.

5. The process according to claim 4, wherein the headspace pressure is from about 1.5 to about 2.5 bar absolute.

6. The process according to claim 1, comprising adding the gas at a flow rate of from about 0.02 to about 0.05 cubic meter/cubic meter/min.

7. The process according to claim 1, wherein the fermentation medium is stirred.

8. The process according to claim 7, wherein the fermentation medium is stirred at a power input of from about 0.070 to about 0.26 kW/cubic meter.

9. The process according to claim 1, wherein the yeast is a *Saccharomyces* sp.

10. The process according to claim 1, wherein the yeast cell is a genetically modified yeast cell, which comprises a genetic modification of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter.

11. The process according to claim 1, wherein the succinic acid is recovered from the fermentation medium.

12. The process according to claim 1, wherein the yeast cell is a genetically modified yeast cell, which comprises a genetic modification of a gene selected from the group consisting of a gene encoding a pyruvate carboxylase, a phosphoenolpyruvate carboxykinase, a malate dehydrogenase, a fumarase, a fumarate reductase, an isocitrate lyase, a malate synthase and a dicarboxylic acid transporter, wherein the gene is homologous to the yeast cell, or is derived from a heterologous fungus, bacteria, or protozoa.

13. The process according to claim 10, wherein said genetic modification results in overexpression of said gene.

14. The process according to claim 10, wherein the gene is derived from bacteria selected from the group consisting of *Escherichia coli, Mannheimia* sp., *Actinobacillus* sp. and *Anaerobiospirillum* sp.

15. The process according to claim 12, wherein the gene is derived from a fungus selected from the group consisting of *Saccharomyces cerevisiae, Rhizopus oryzae, Schizosaccharomyces pombe, Aspergillus niger*, and *Kluyveromyces lactis*.

16. The process according to claim 12, wherein the gene is derived from a protozoa, and the protozoa is *Trypanosoma* sp.

17. The process according to claim 9, wherein the yeast is *Saccharomyces cerevisiae*.

18. The process according to claim 1, wherein the gas comprises from 21 to about 32 v/v % of oxygen.

19. The process according to claim 1, wherein the gas comprises from about 22 to about 30 v/v % of oxygen.

* * * * *